United States Patent
Kang et al.

(10) Patent No.: US 11,490,603 B2
(45) Date of Patent: Nov. 8, 2022

(54) ANIMAL MODEL OF BRAIN TUMOR AND MANUFACTURING METHOD OF ANIMAL MODEL

(71) Applicants: KOREA ADVANCED INSTITUTE OF SCIENCE AND TECHNOLOGY, Daejeon (KR); YONSEI UNIVERSITY, UNIVERSITY—INDUSTRY FOUNDATION (UIF), Seoul (KR)

(72) Inventors: Seok Gu Kang, Suwon-si (KR); Jeong Ho Lee, Daejeon (KR); Joo Ho Lee, Daejeon (KR); Jeong Eun Lee, Daejeon (KR)

(73) Assignees: KOREA ADVANCED INSTITUTE OF SCIENCE AND TECHNOLOGY, Daejeon (KR); YONSEI UNIVERSITY, UNIVERSITY—INDUSTRY FOUNDATION (UIF), Seoul (KR)

( * ) Notice: Subject to any disclaimer, the term of this patent is extended or adjusted under 35 U.S.C. 154(b) by 154 days.

(21) Appl. No.: 16/050,006

(22) Filed: Jul. 31, 2018

(65) Prior Publication Data
US 2019/0239494 A1 Aug. 8, 2019

(30) Foreign Application Priority Data
Feb. 6, 2018 (KR) .......................... 10-2018-0014741

(51) Int. Cl.
*A01K 67/027* (2006.01)
*A61K 49/00* (2006.01)

(52) U.S. Cl.
CPC ...... *A01K 67/0276* (2013.01); *A61K 49/0008* (2013.01); *A01K 2217/075* (2013.01); *A01K 2267/0331* (2013.01)

(58) Field of Classification Search
CPC .......... A01K 67/0276; A01K 2217/075; A01K 2267/0331; A01K 2227/105; A01K 2217/15; A01K 67/0275; A61K 49/0008; C12N 9/16; C12N 2800/30; C07K 14/4746; C07K 16/22; C07K 16/30; C07K 16/40; C12Q 1/6881; C12Q 1/6886; C12Q 2537/16; C12Q 2600/156; C12Q 2600/158
See application file for complete search history.

(56) References Cited

U.S. PATENT DOCUMENTS

2010/0100974 A1 4/2010 Charest

FOREIGN PATENT DOCUMENTS

| JP | 2009-523709 | 6/2009 |
|---|---|---|
| KR | 10-1492436 | 2/2015 |
| KR | 10-2018-0024262 | 3/2018 |

OTHER PUBLICATIONS

Yin et al. "Generation of an MC3R knock-out pig by CRSPR/Cas9 combined with somatic cell nuclear transfer (SCNT) technology." Lipids in Health and Disease vol. 18, 122 (2019) (Year: 2019).*
You et al. "Effects of Melanocortin 3 and 4 Receptor Deficiency on Energy Homeostasis in Rats."Scientific Reports vol. 6: 34938 (2016) (Year: 2016).*
Goldstein et al. "Variation in zygotic CRISPR/Cas9 gene editing outcomes generates novel reporter and deletion alleles at the Gdf11 locus."Scientific Reports vol. 9: 18613 (2019) (Year: 2019).*
Vesikansa, A. "Unraveling of Central Nervous System Disease Mechanisms Using CRISPR Genome Manipulation."J Cent Nerv Syst Dis. 2018; 10: (Year: 2018).*
He et al. "Use of CRISPR/Cas9 technology efficiently targetted goat myostatin through zygotes microinjection resulting in double-muscled phenotype in goats."Biosci Rep (2018) 38 (6) (Year: 2018).*
McCarty et al. "Multiplexed CRISPR technologies for gene editing and transcriptional regulation."Nature Communications vol. 11, : 1281 (2020) (Year: 2020).*
An et al. "Epidermal growth factor receptor and EGFRvIII in glioblastoma: signaling pathways and targeted therapies. "Oncogene. Mar. 2018;37(12):1561-1575. (Year: 2018).*
NCBI, "Mus musculus targeted KO-first, conditional ready, lacZ-tagged mutant allele Trp53:tm1a (EUCOMM)Hmgu; transgenic", Genbank accession No. JN964617.1.
NCBI, "Mus musculus PTENbeta (PTEN) mRNA, complete cds", Genbank accession No. KX421108.1, 2017.
Joo Ho LEE, "Human Glioblastoma Arises from The Distant Subventricular Zone Normal-appearing but Harboring Tumor-initiating Mutations", The 13th KOGO Winter Symposium 2017, Poster Presentation, Feb. 8, 2017.
Joo Ho Lee, MD, MS, Korea Advanced Institute of Science and Technology, Daejeon, Republic of Korea., Abstract 2455, "Human glioblastoma arises from the distant subventricular zone normal appearing but harboring tumor-initiating mutations.", Travel Awards, Awardee list of Mar. 9, 2016, AACR Annual Meeting 2017, Washington DC, Apr. 1, 2017.

(Continued)

*Primary Examiner* — Titilayo Moloye
(74) *Attorney, Agent, or Firm* — Lex IP Meister, PLLC

(57) ABSTRACT

The present invention relates to a brain tumor animal model that directly reflects the phenomenon in a human patient and a method of preparing the same, and more specifically, a brain tumor animal model that mutations are introduced into p53, Pten, and EGFR genes, a screening method of a therapeutic agent for a brain tumor using the animal model, and a preparing method thereof.

4 Claims, 34 Drawing Sheets
(27 of 34 Drawing Sheet(s) Filed in Color)
Specification includes a Sequence Listing.

(56) References Cited

OTHER PUBLICATIONS

Seok Gu KANG, "Human glioblastoma arises from normal subventricuiar zone harboring tumor-initiating mutations", 5th Quadrennial Meeting of the World Federation of Neuro-Oncology Societies (WFNOS), May 5, 2017.
Joo Ho Lee, "Human glioblastoma arises from the distant subventricuiar zone normal-appearing but harboring tumor-initiating mutations", SY6-02, Symposium 6, APCC 2017 Seoul, Jun. 22, 2017.
Seok Gu Kang, "Starting point of human glioblastoma, IDH-wildtype: subventricuiar zone", ASNO 2017 The 14th Meeting of the Asian Society for Neuro-Oncology, Oct. 30, 2017.
Seok Gu Kang, "The origin of human glioblastoma, Firework pattern glioblastoma from subventricular zone", SNO 22nd Annual Meeting and Education Day of the Society for Neuro-Oncology, Nov. 17, 2017.

\* cited by examiner

[FIG. 1]
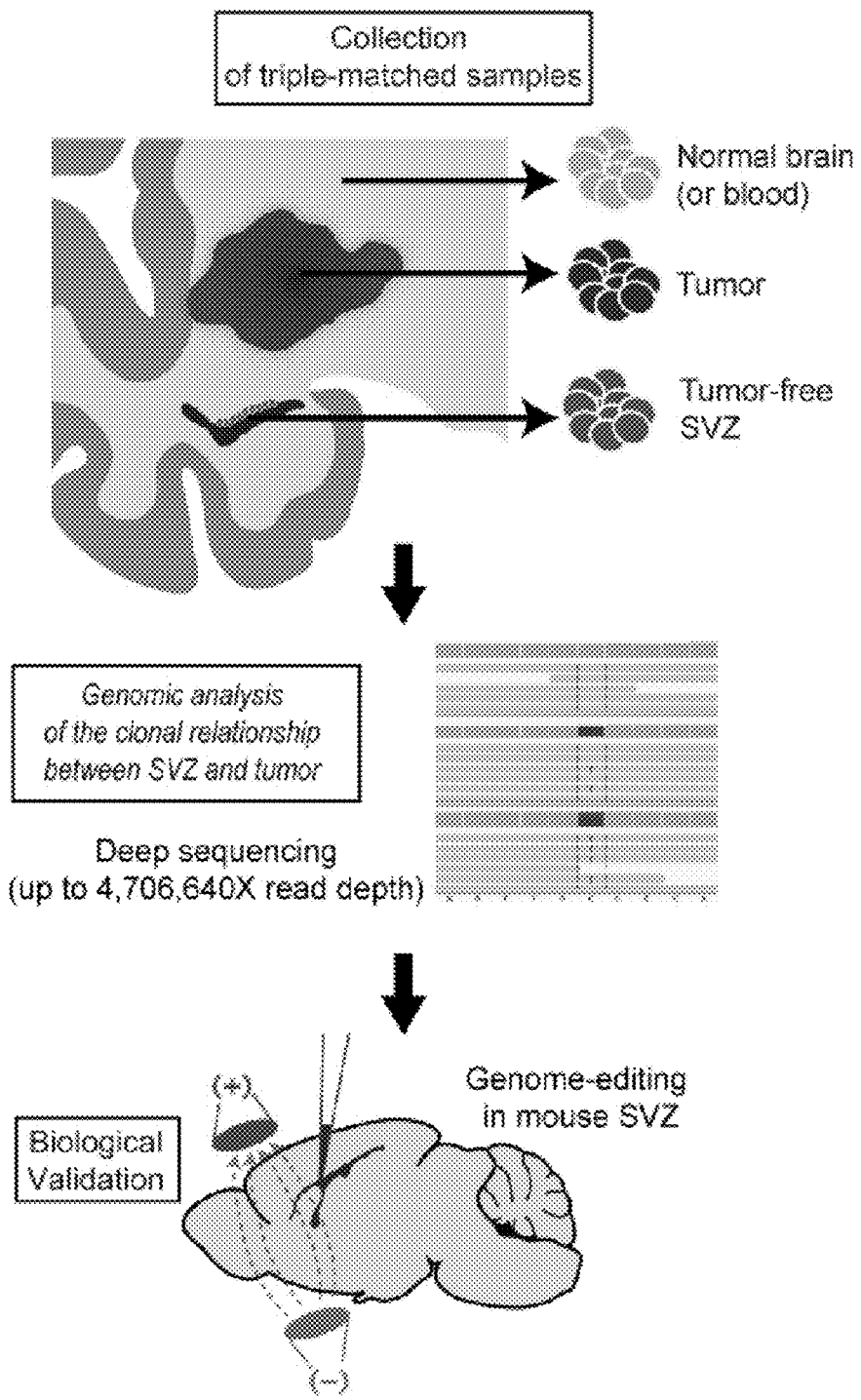

[FIG. 2]
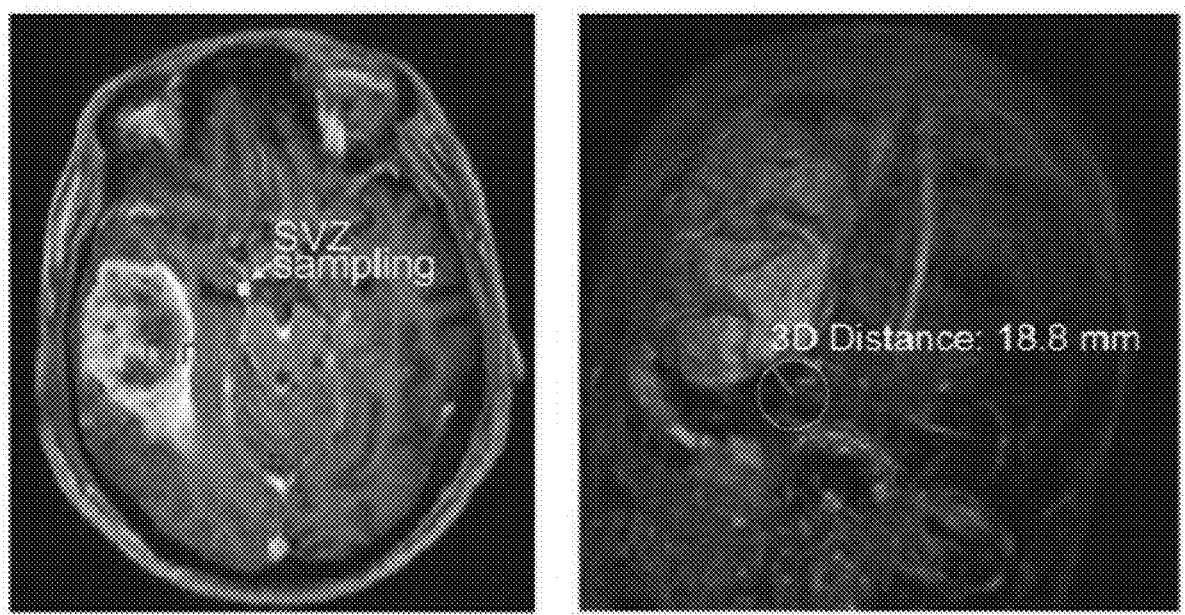

【FIG. 3】
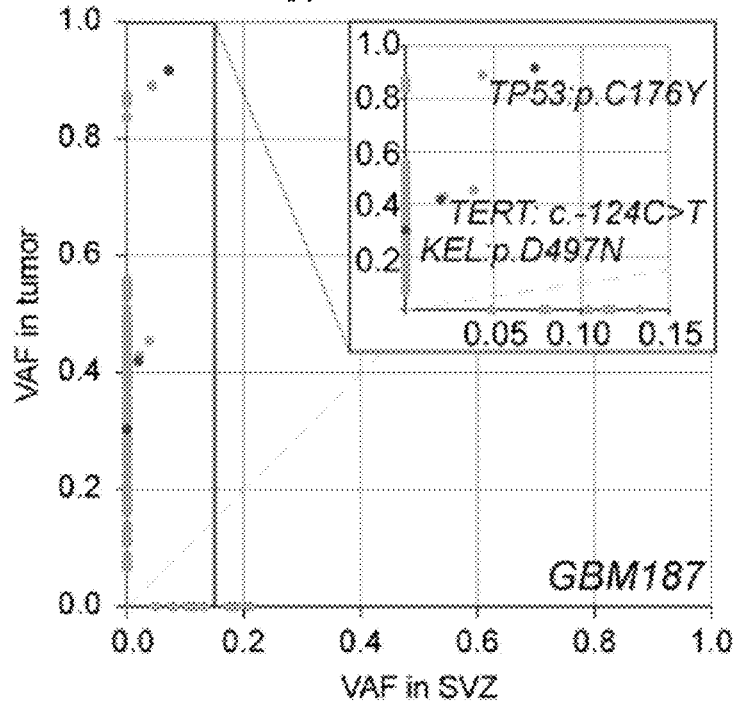
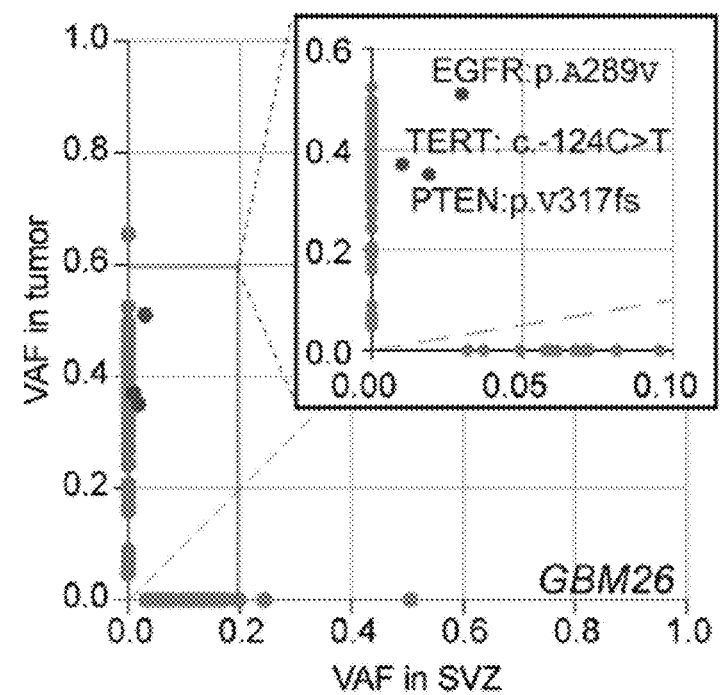

[FIG. 4]
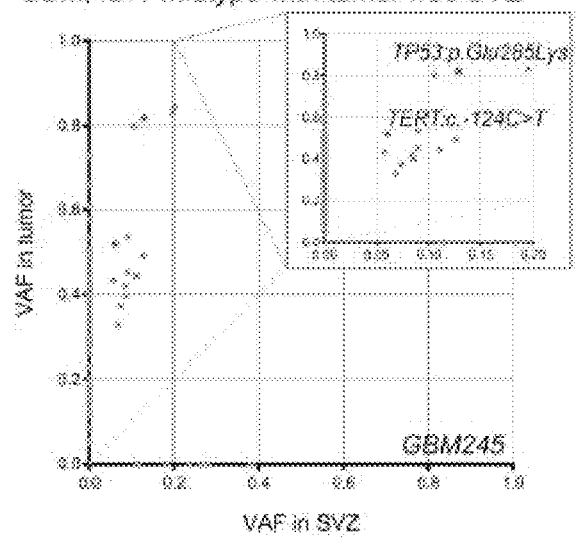
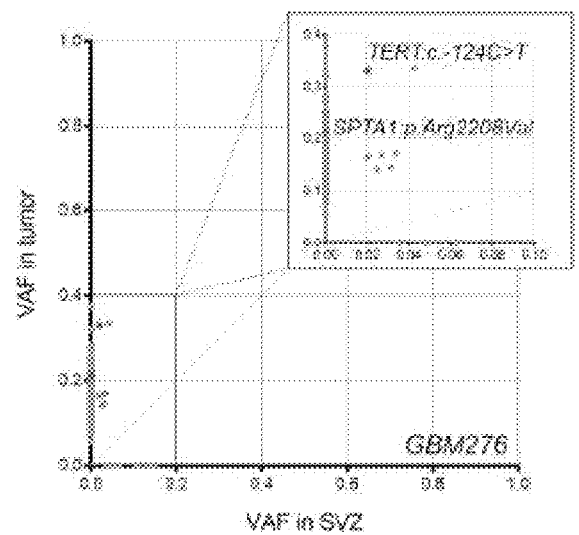
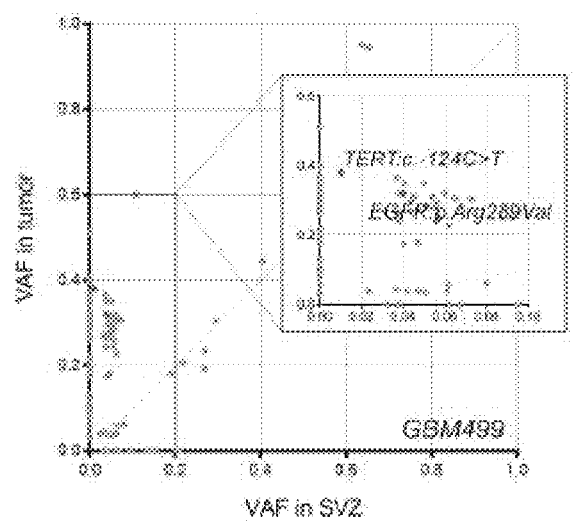
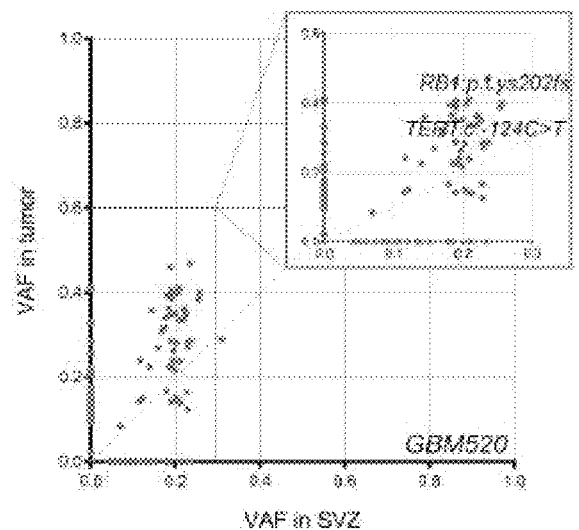

[FIG. 5]
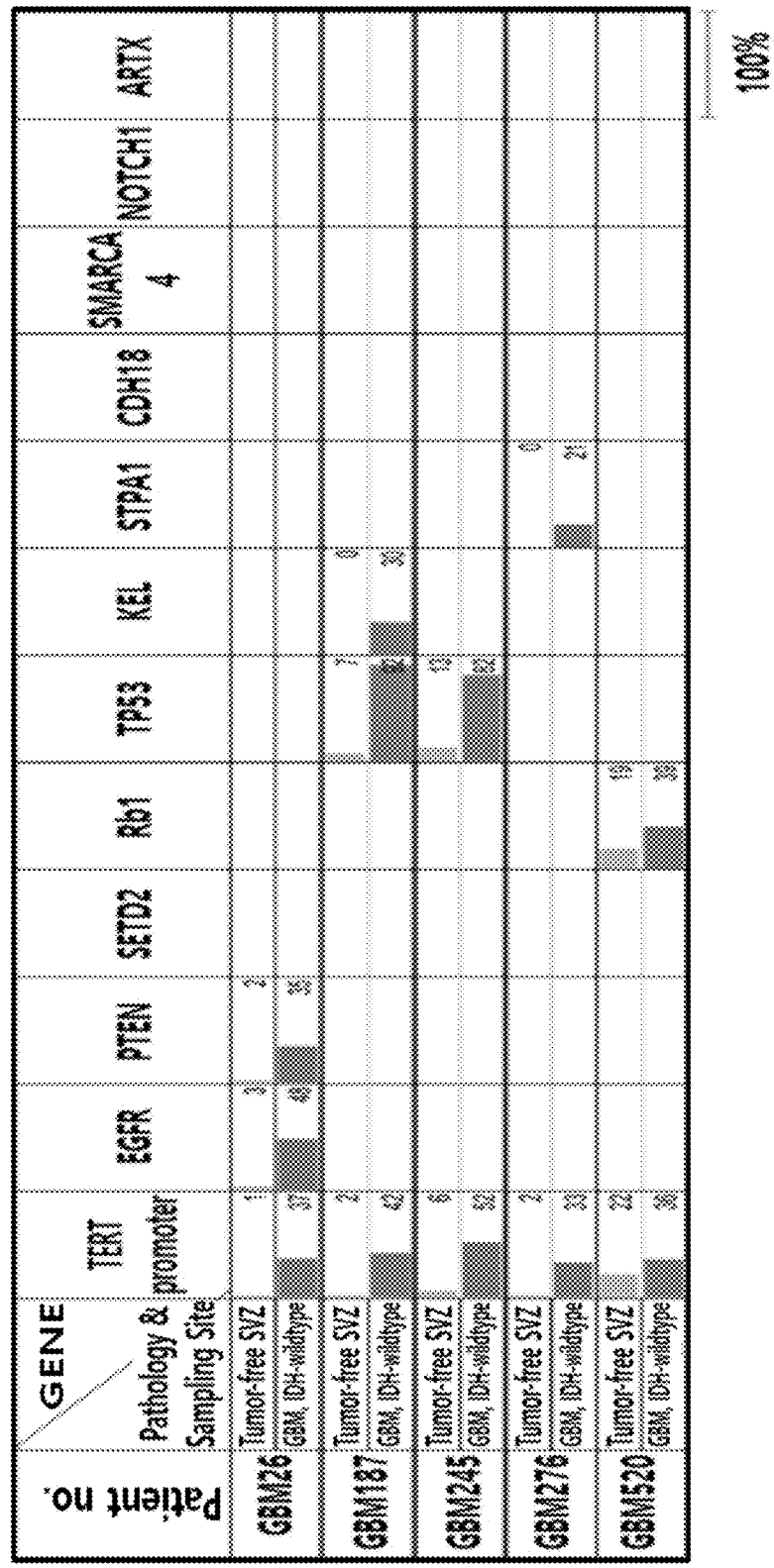

[FIG. 6]
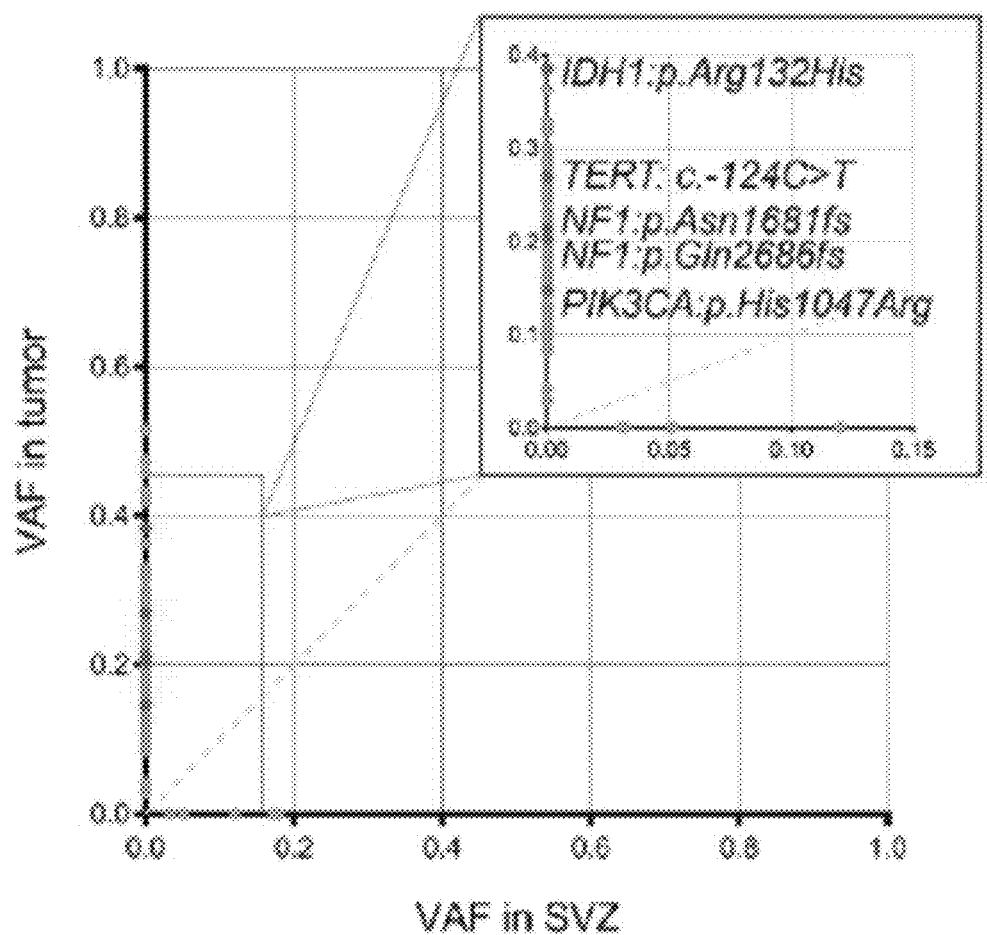

[FIG. 7]
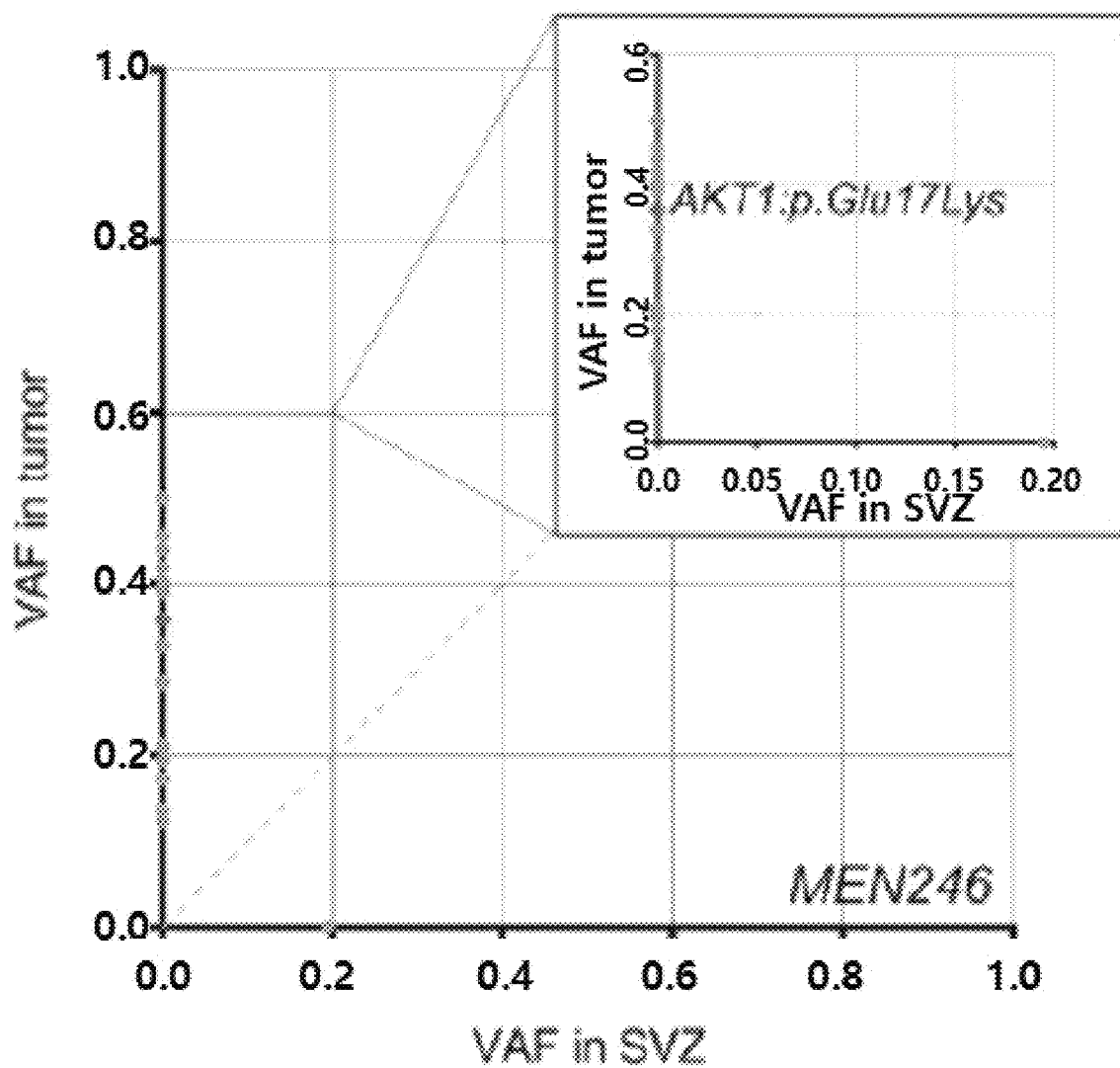

[FIG. 8]
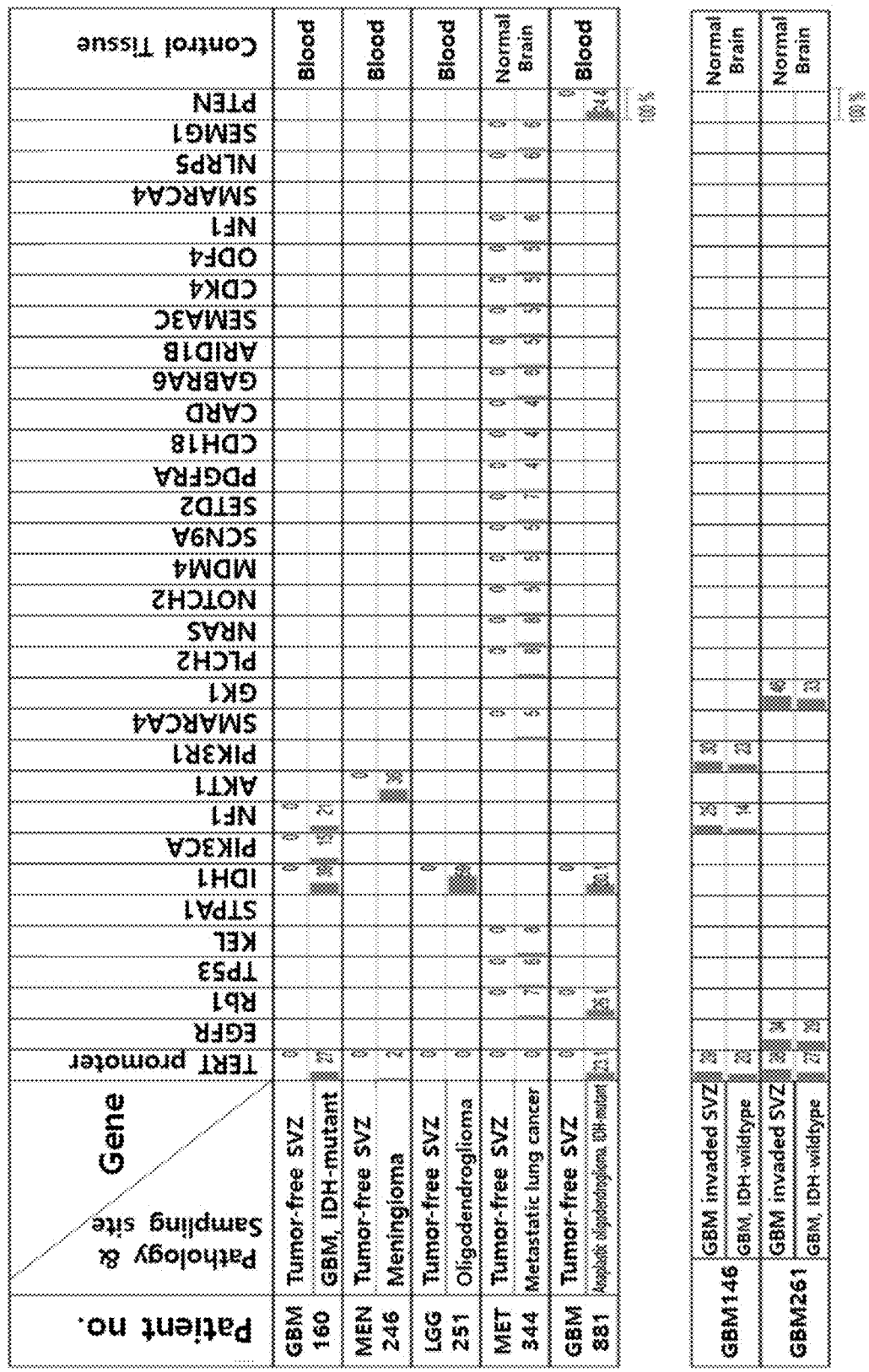

[FIG. 9]
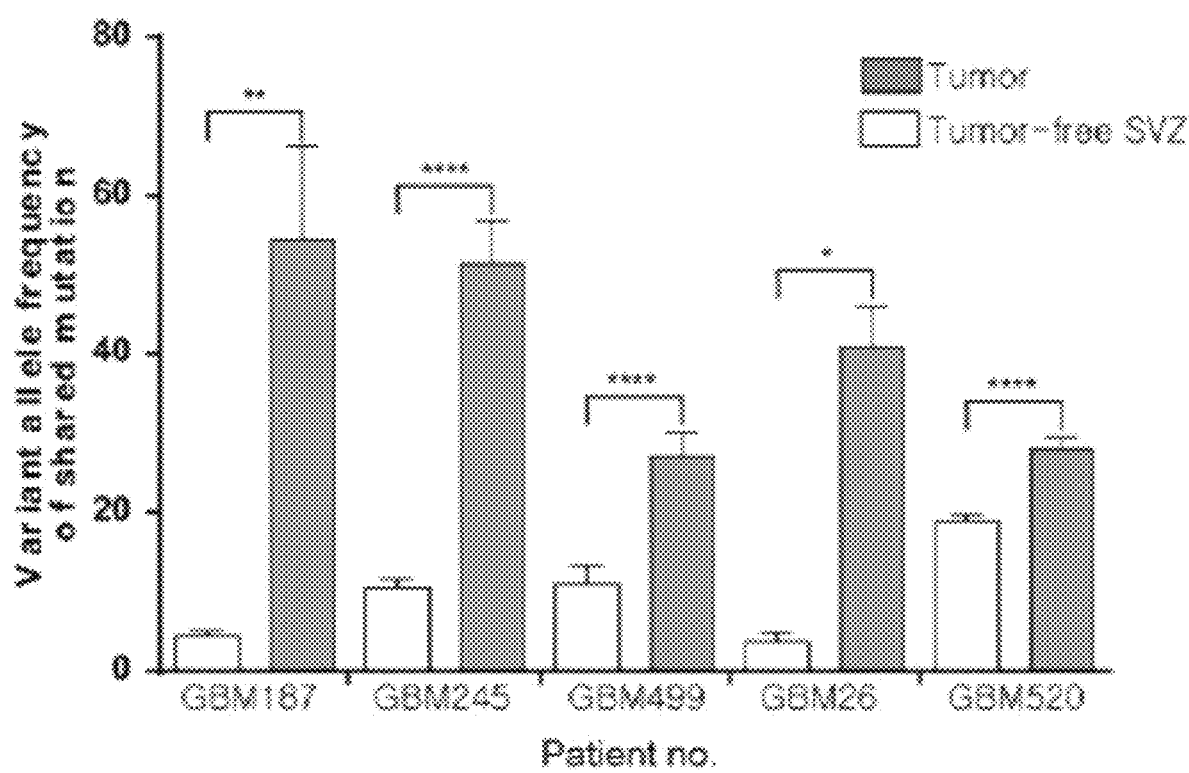

[FIG. 10]
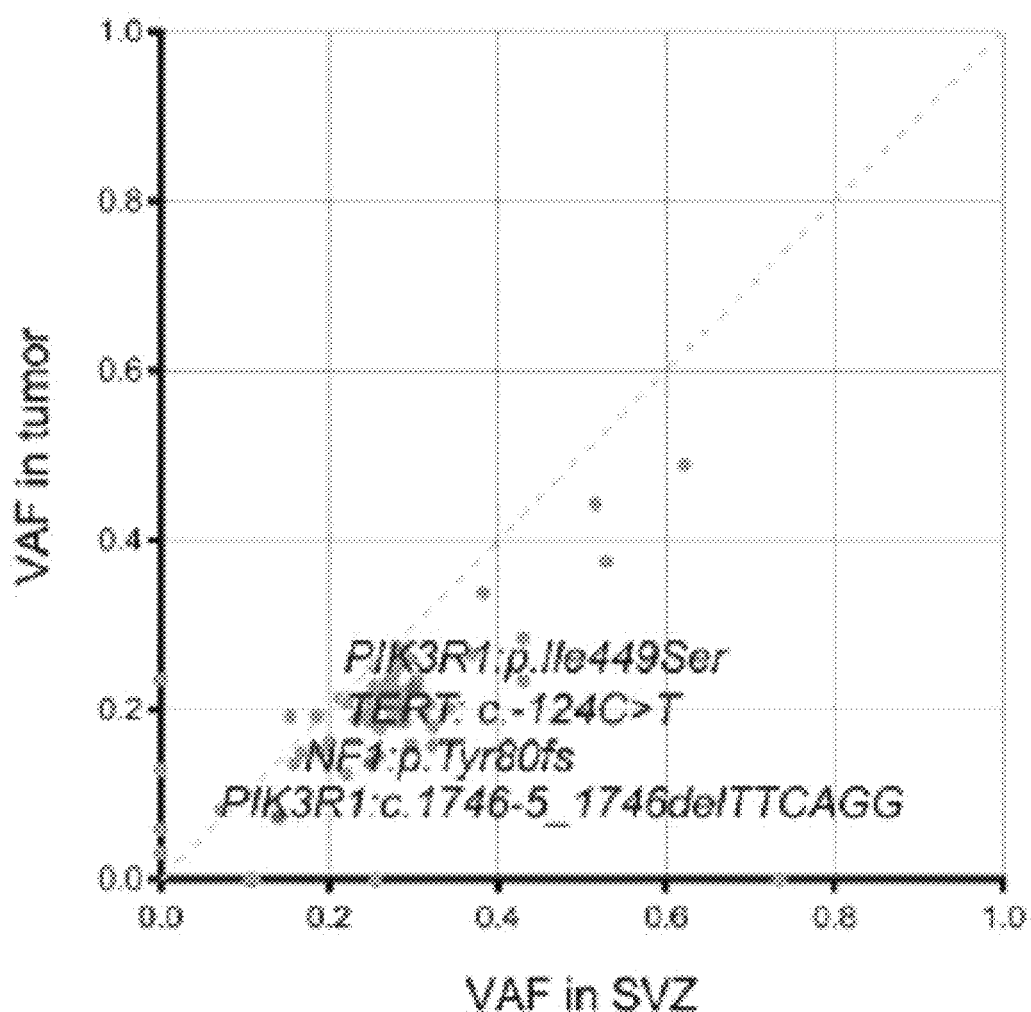

[FIG. 11]
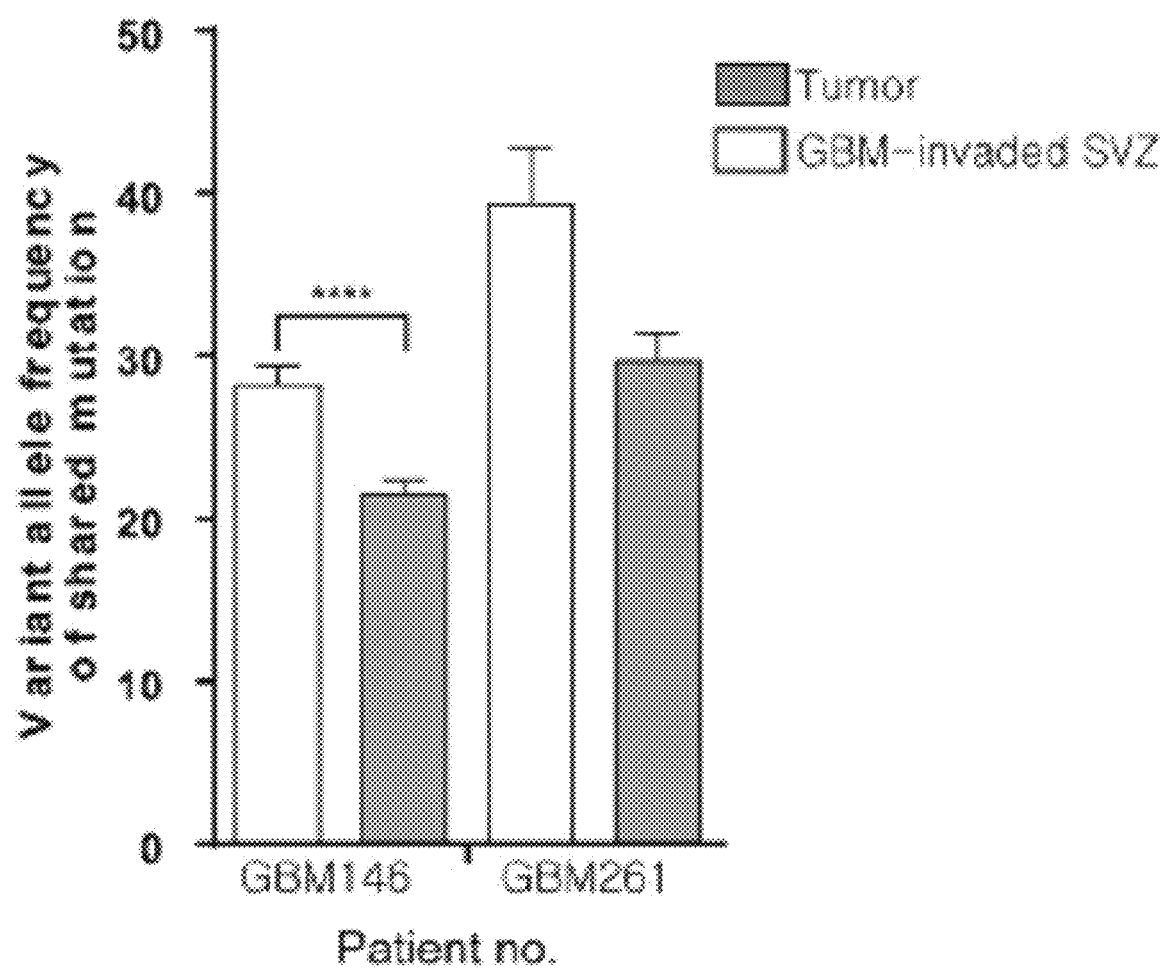

[FIG. 12]
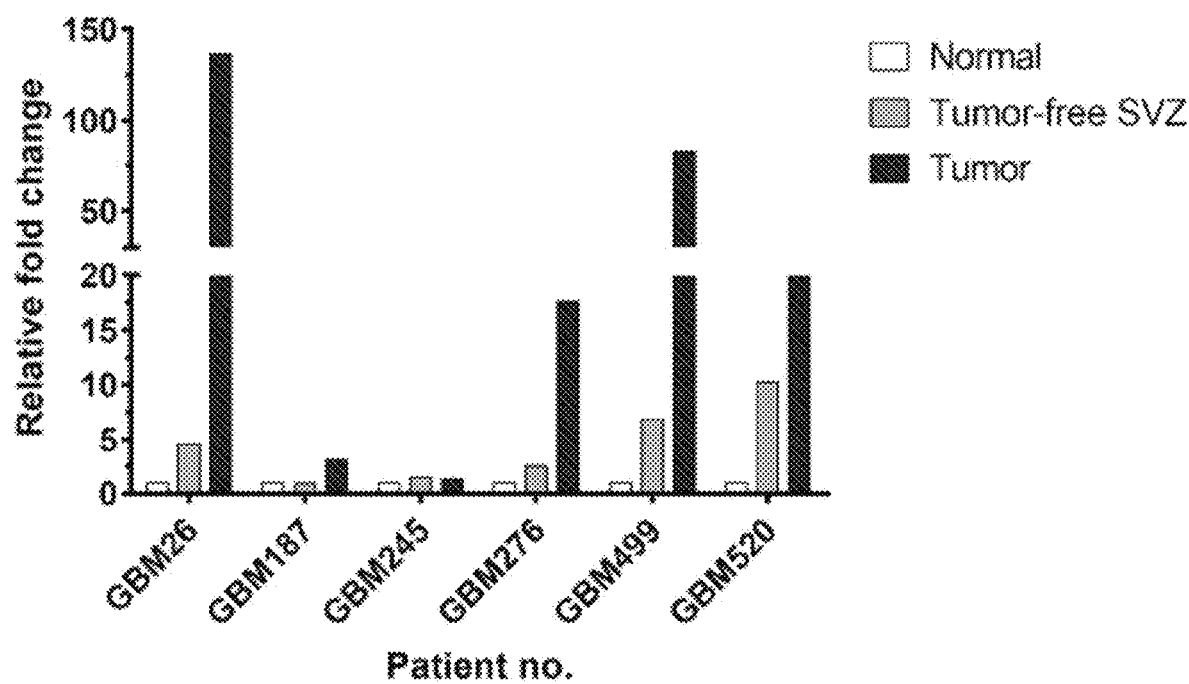

[FIG. 13]
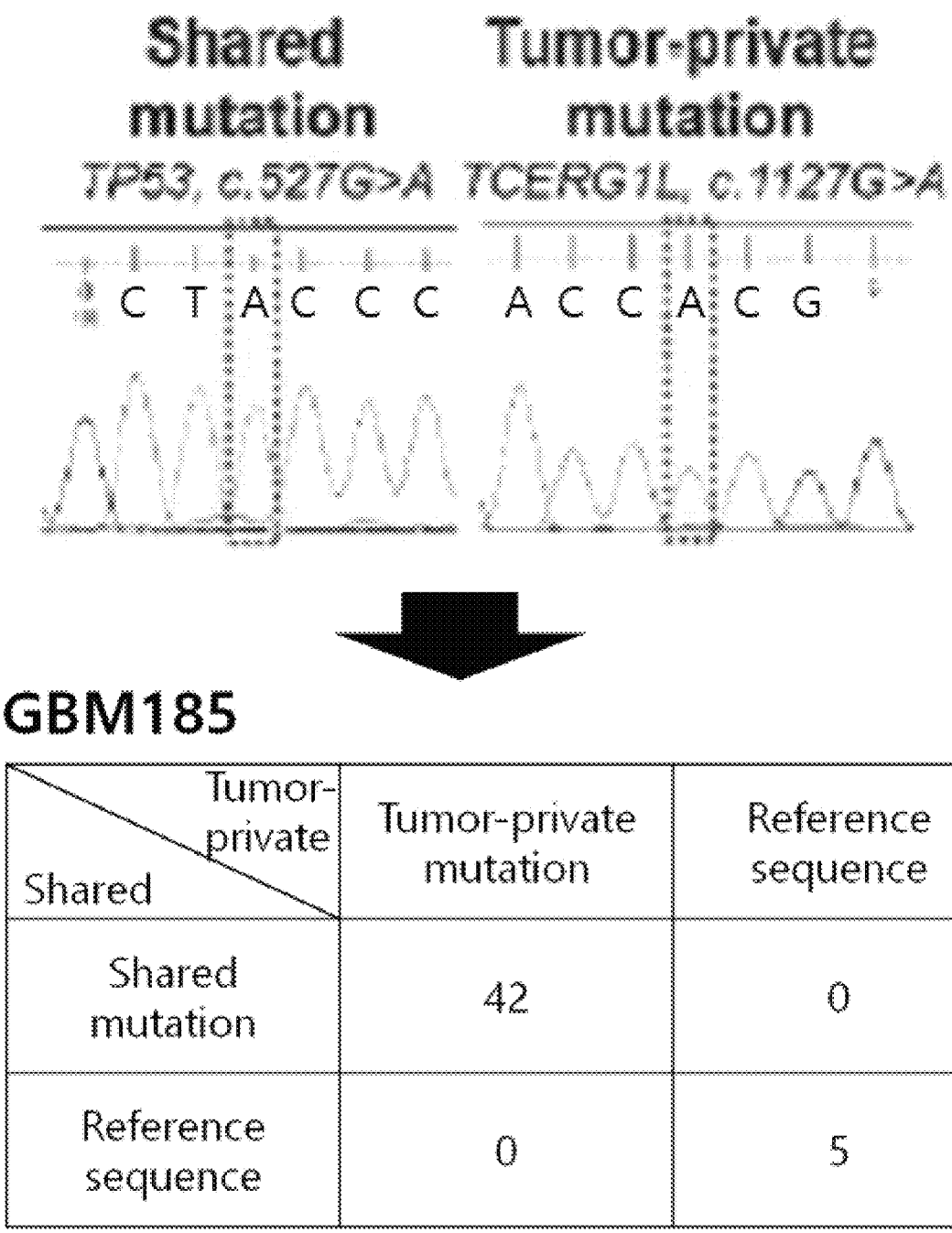

[FIG. 14]
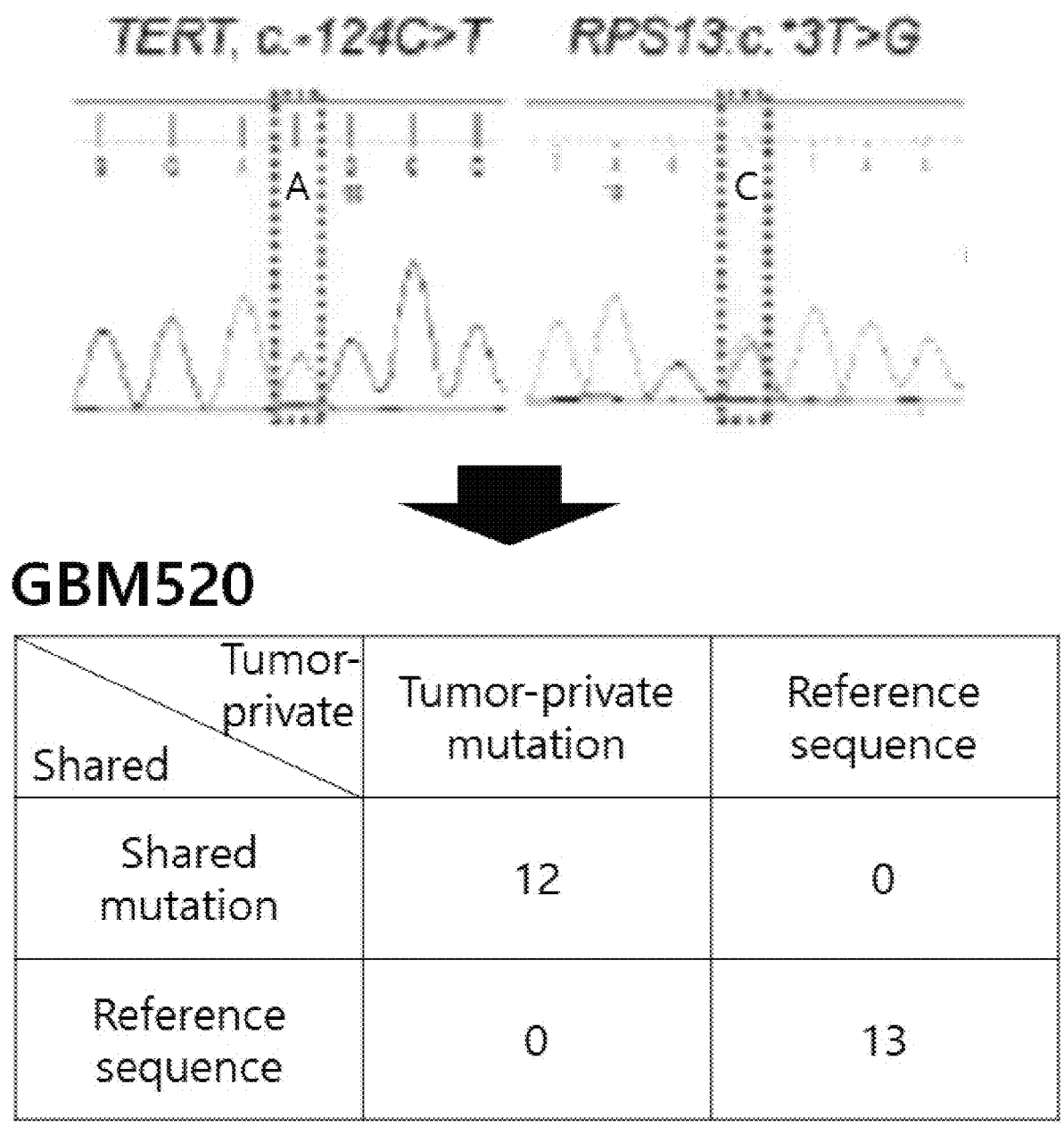

[FIG. 15]
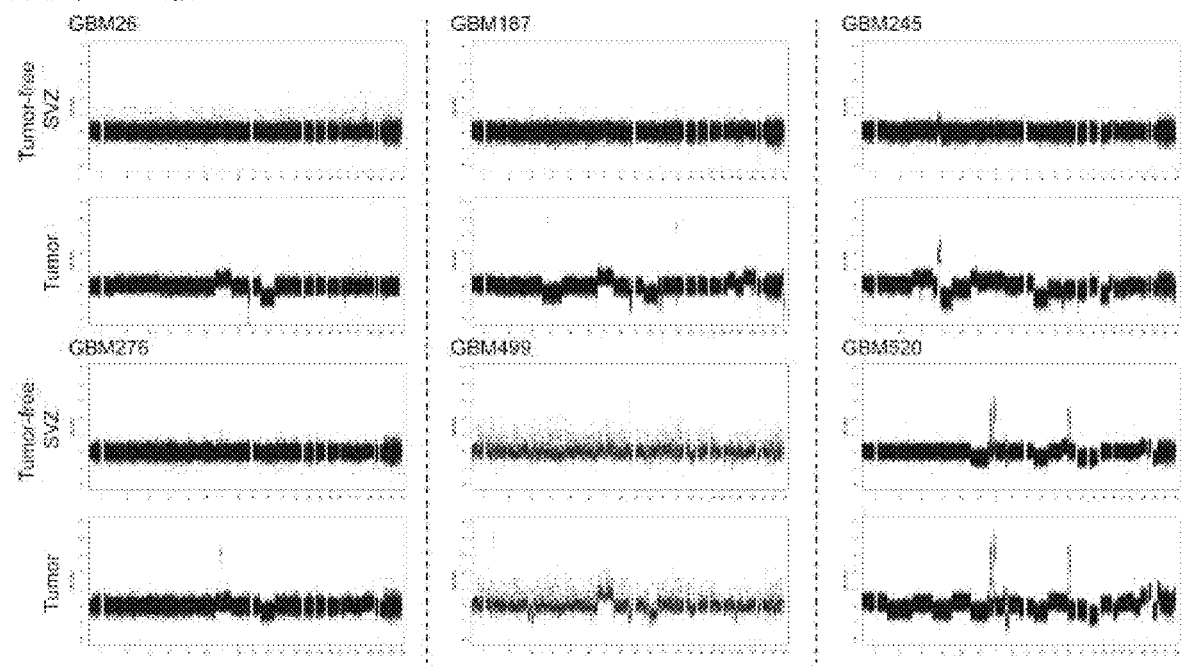
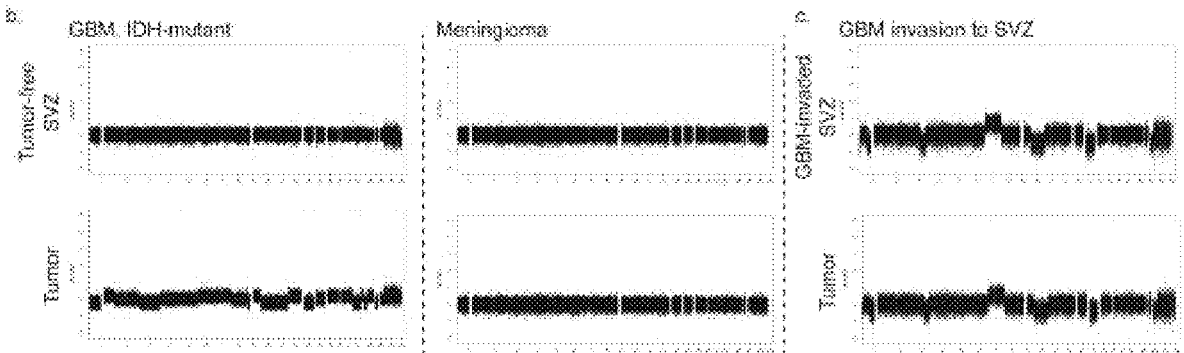

[FIG. 16]
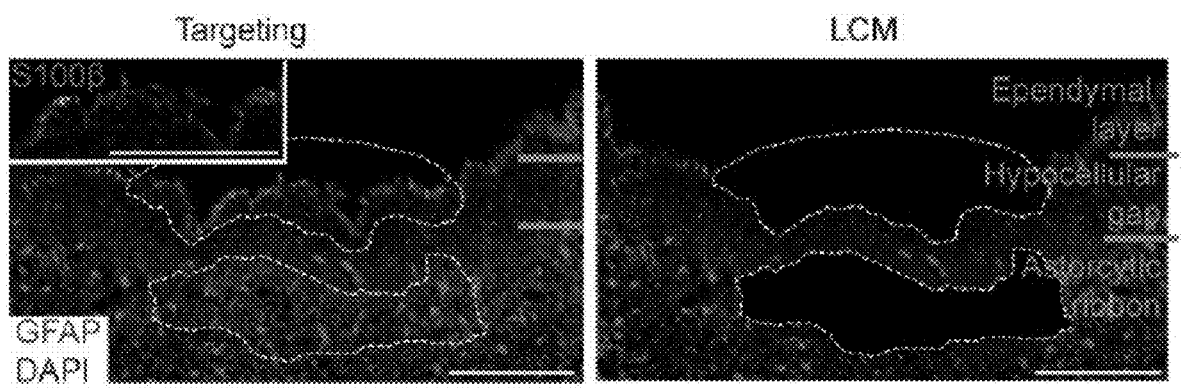

[FIG. 17]
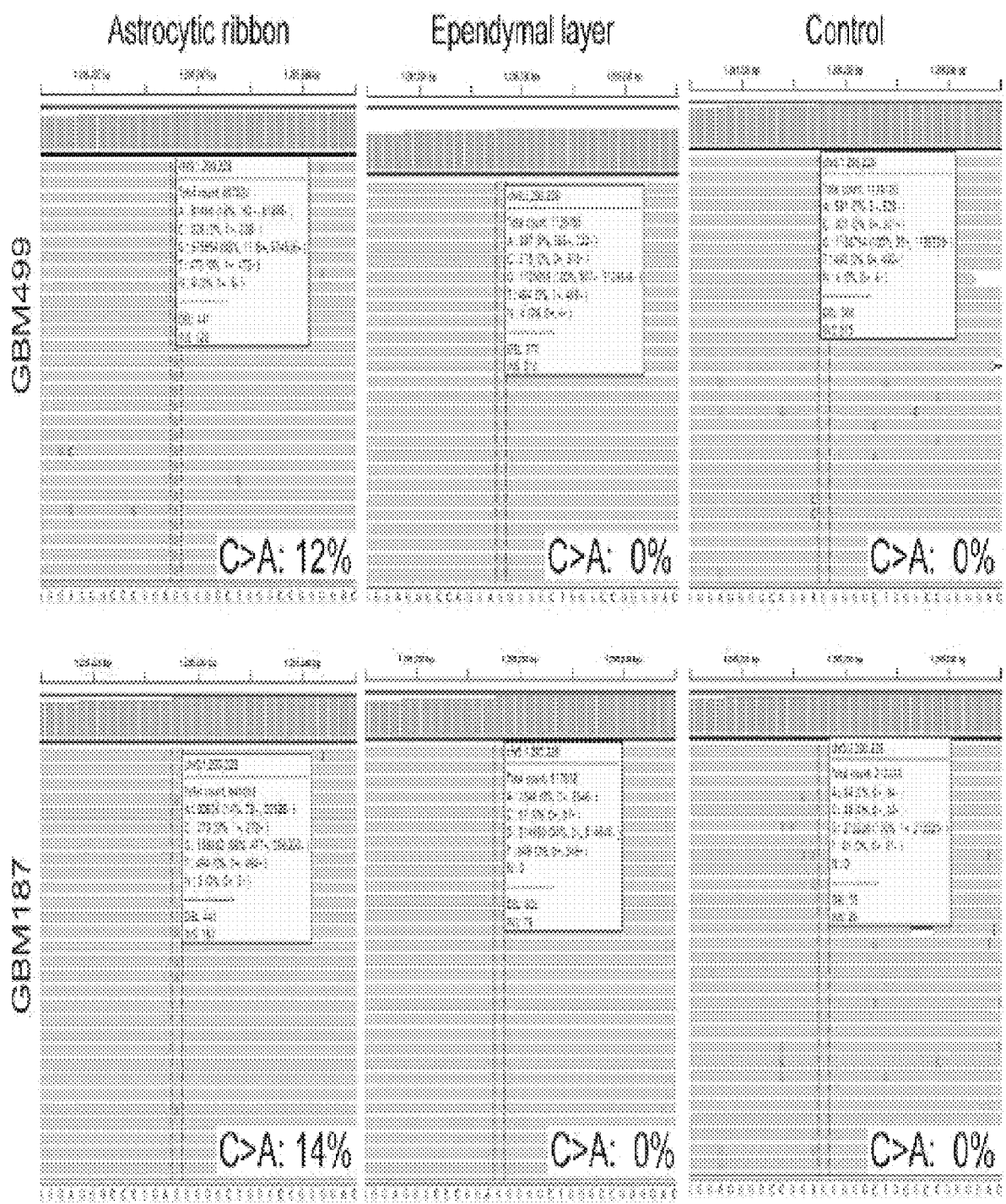

[FIG. 18]
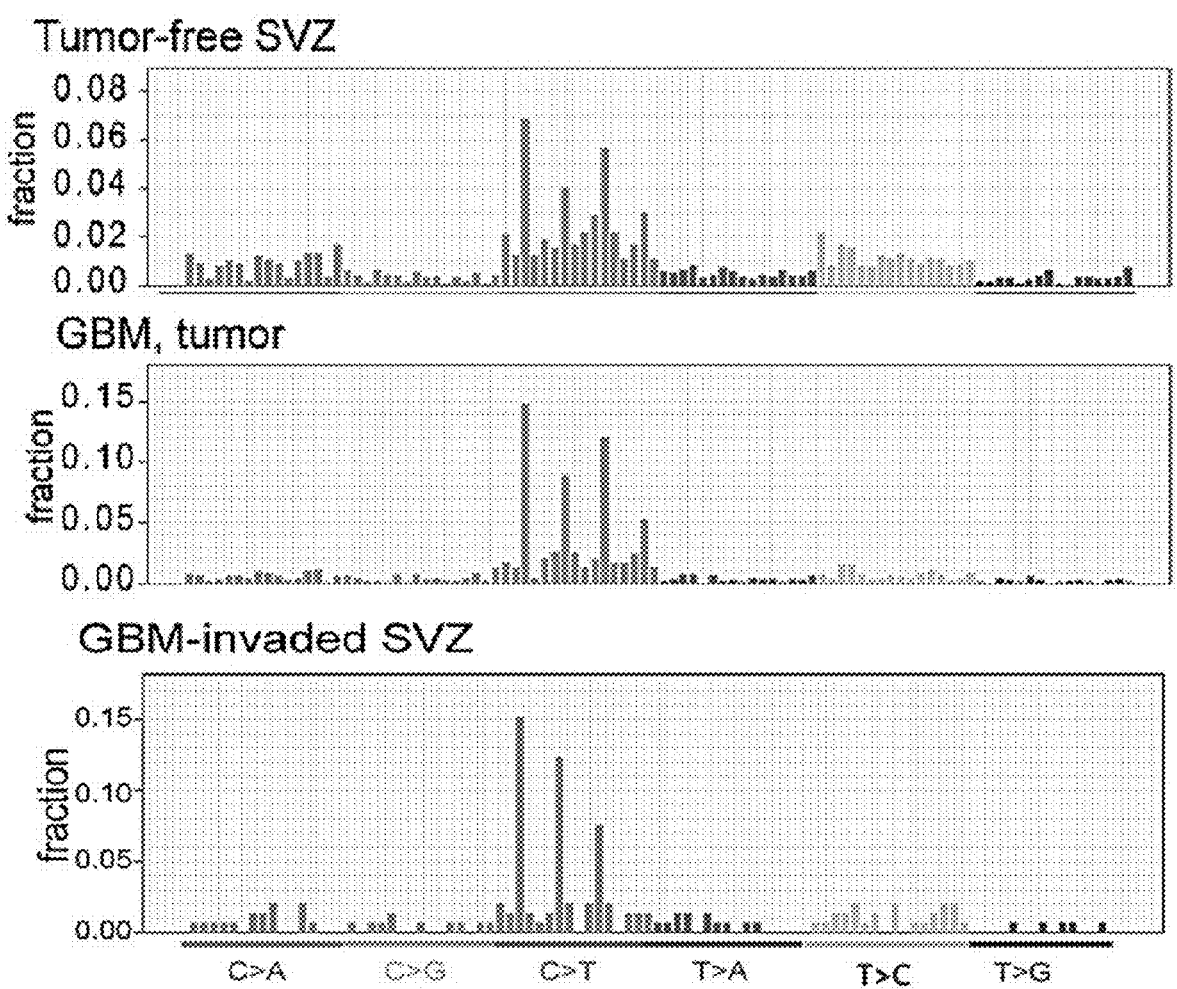

[FIG. 19]
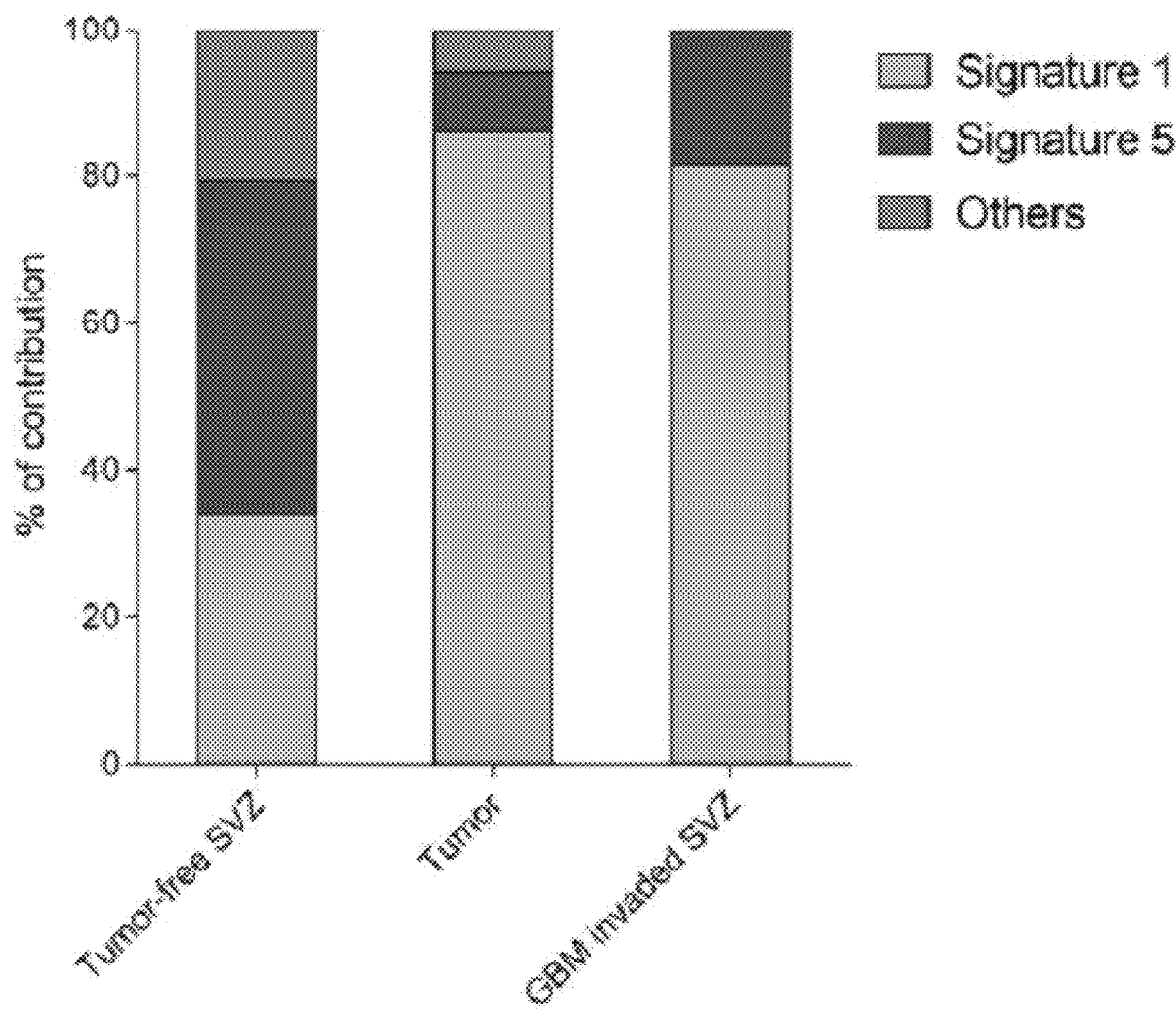

[FIG. 20]
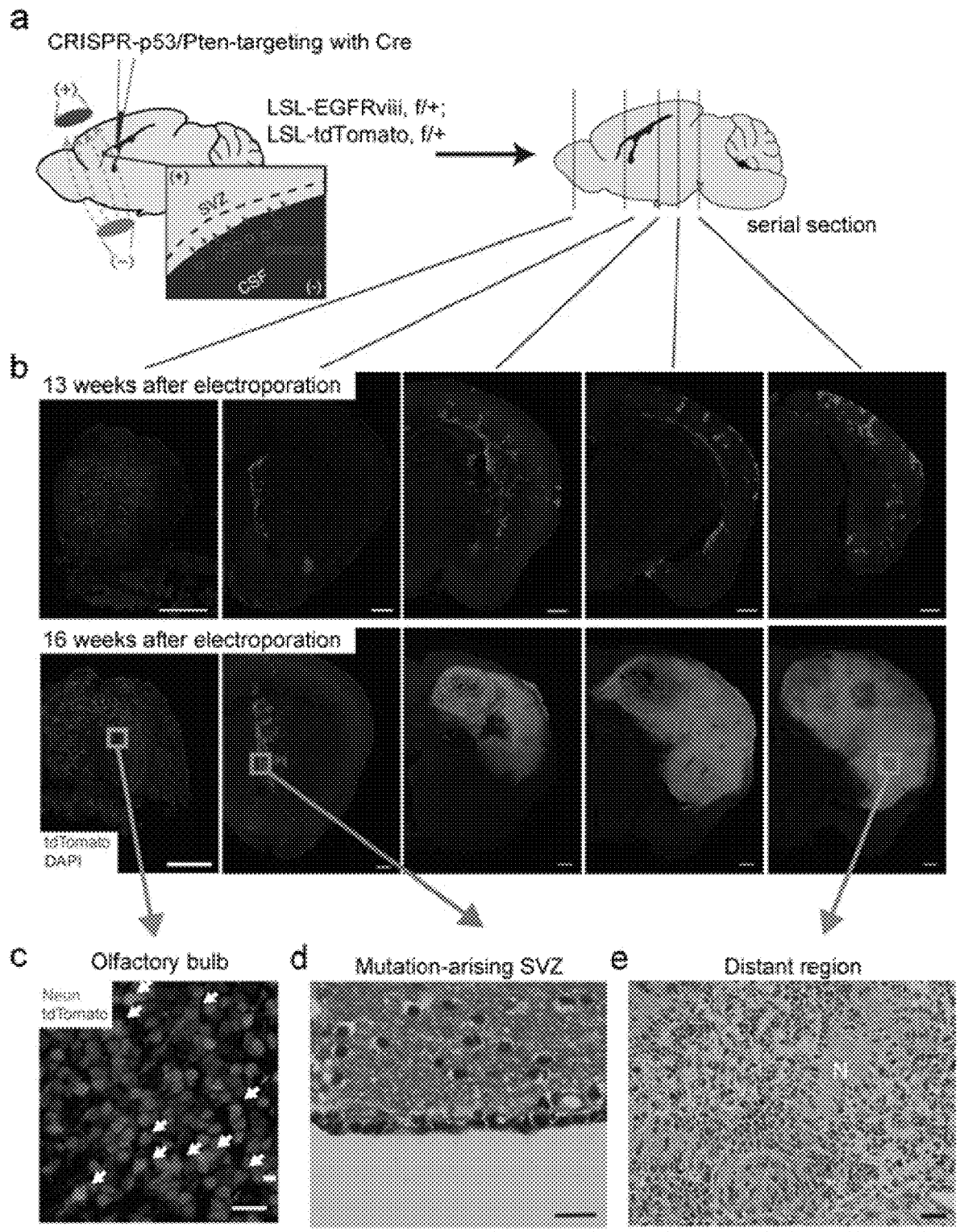

[FIG. 21]
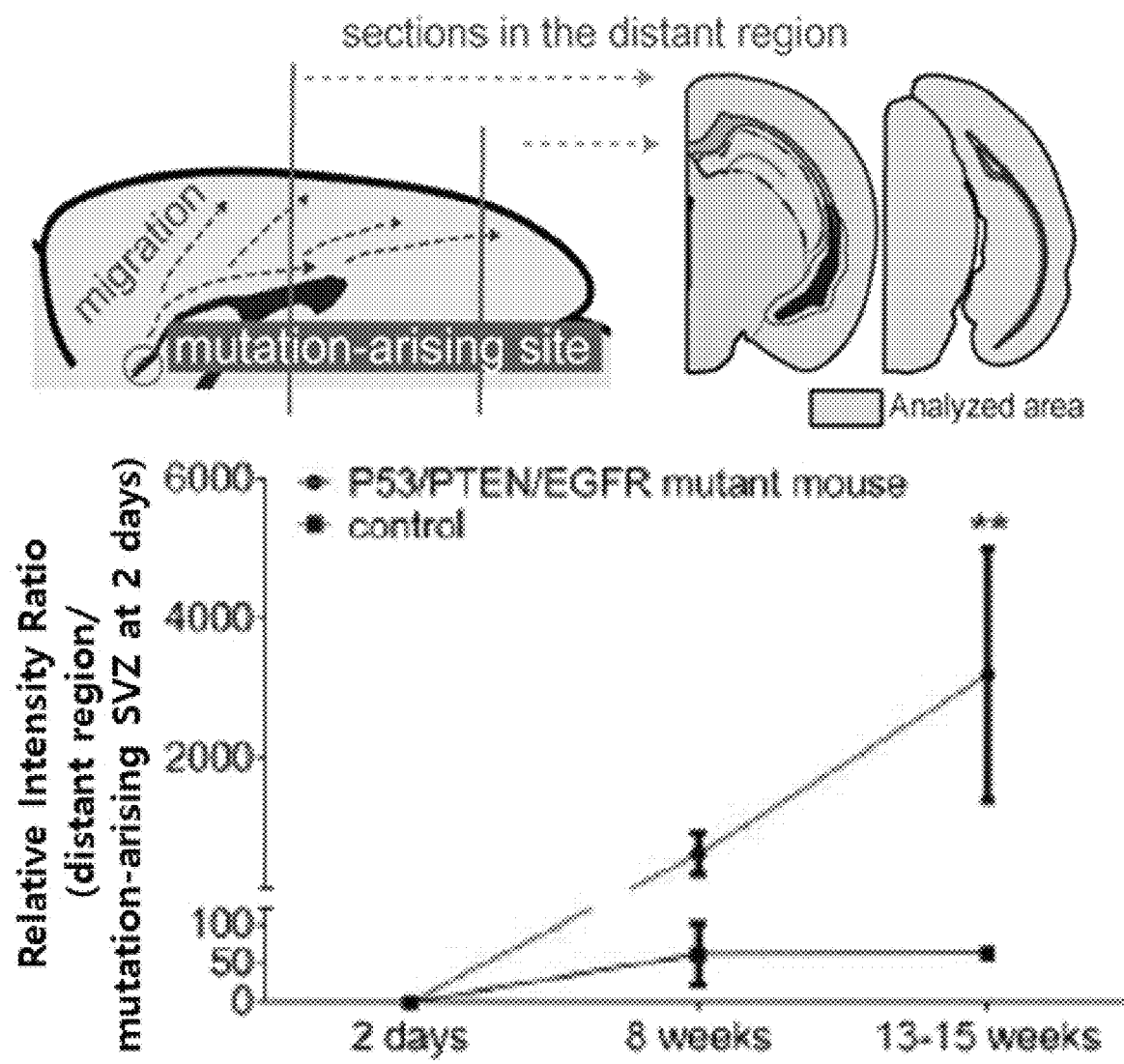

【FIG. 22】
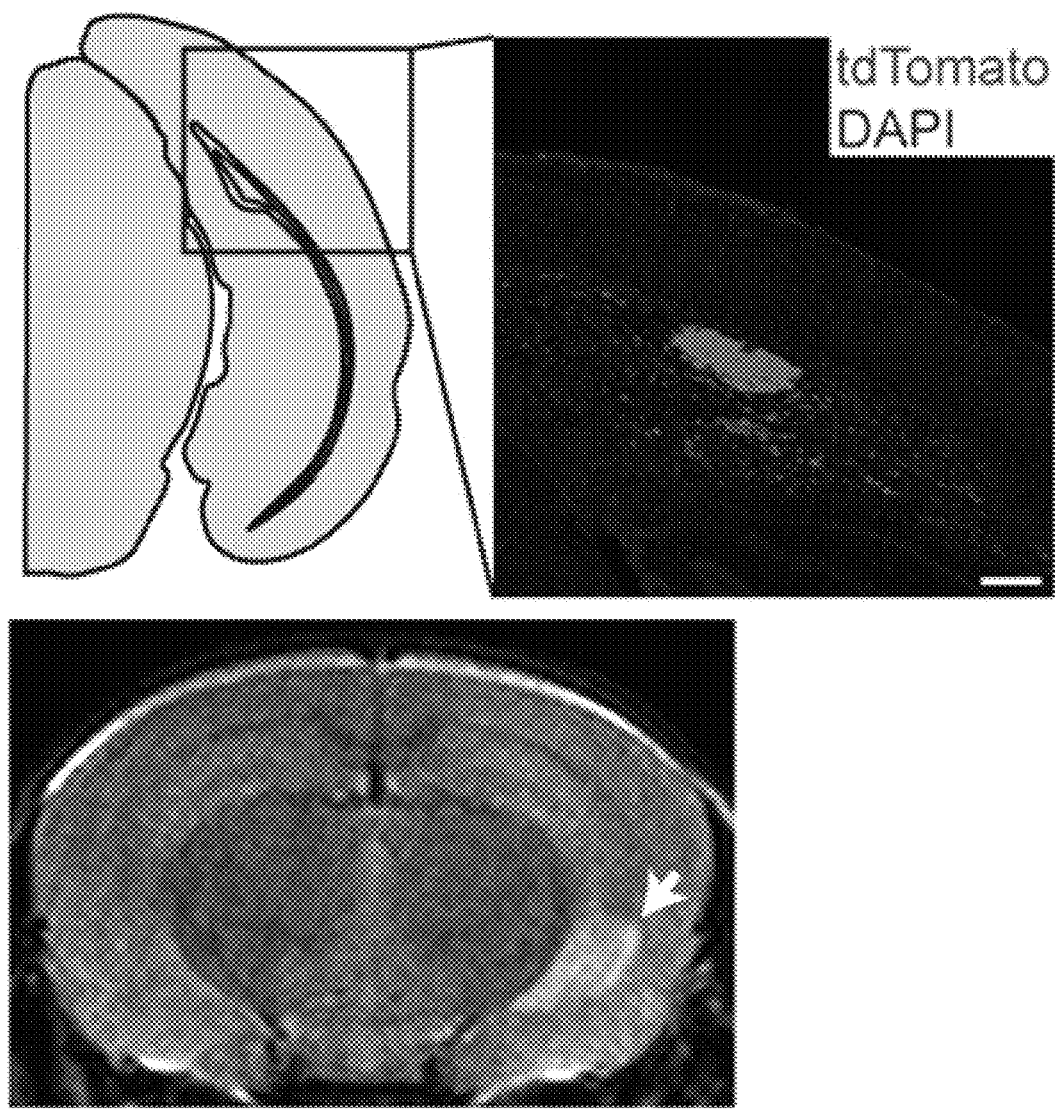
| | Rostral part | Distal part |
|---|---|---|
| n (%) | 6 (33%) | 12 (67%) |

[FIG. 23]
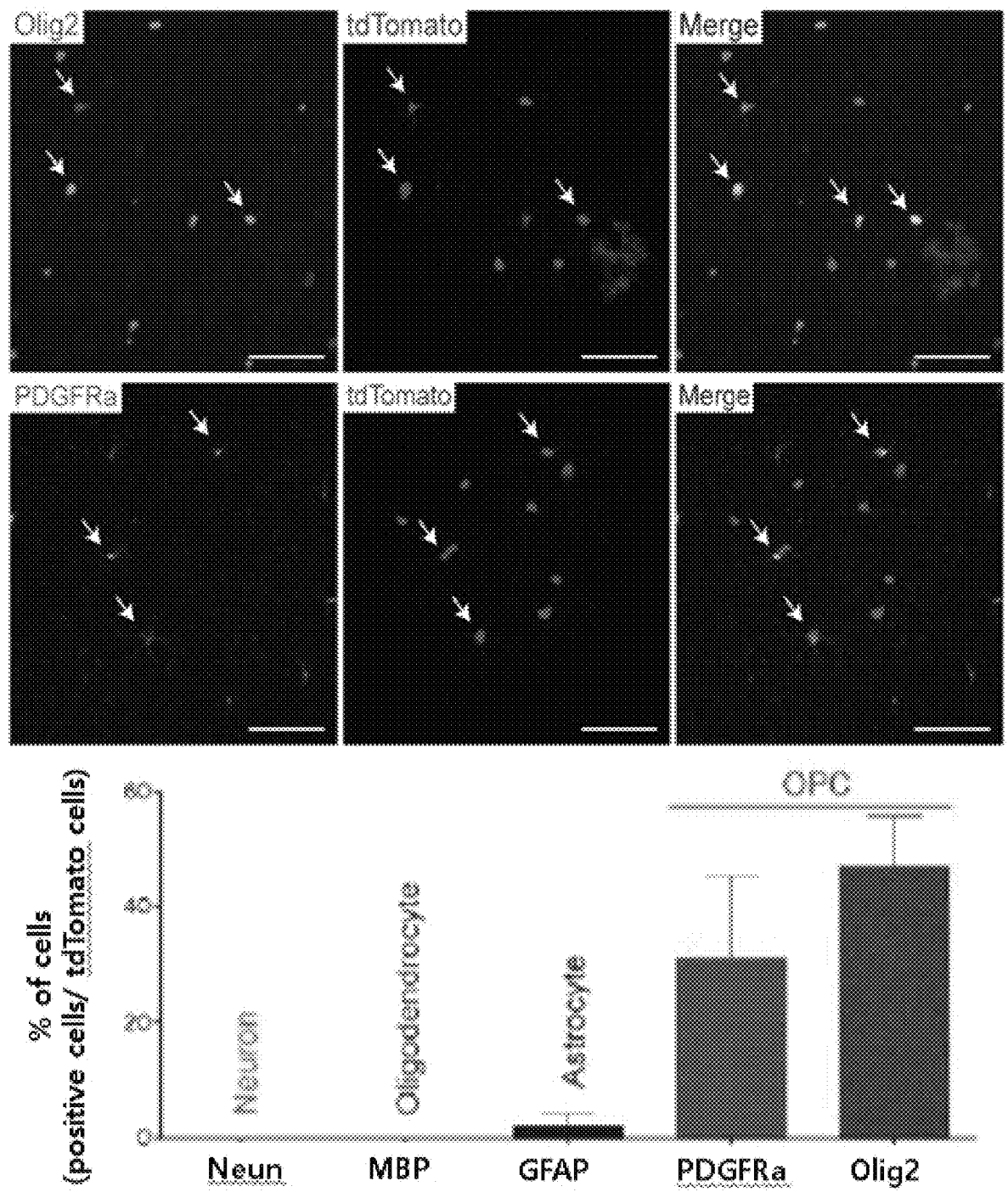

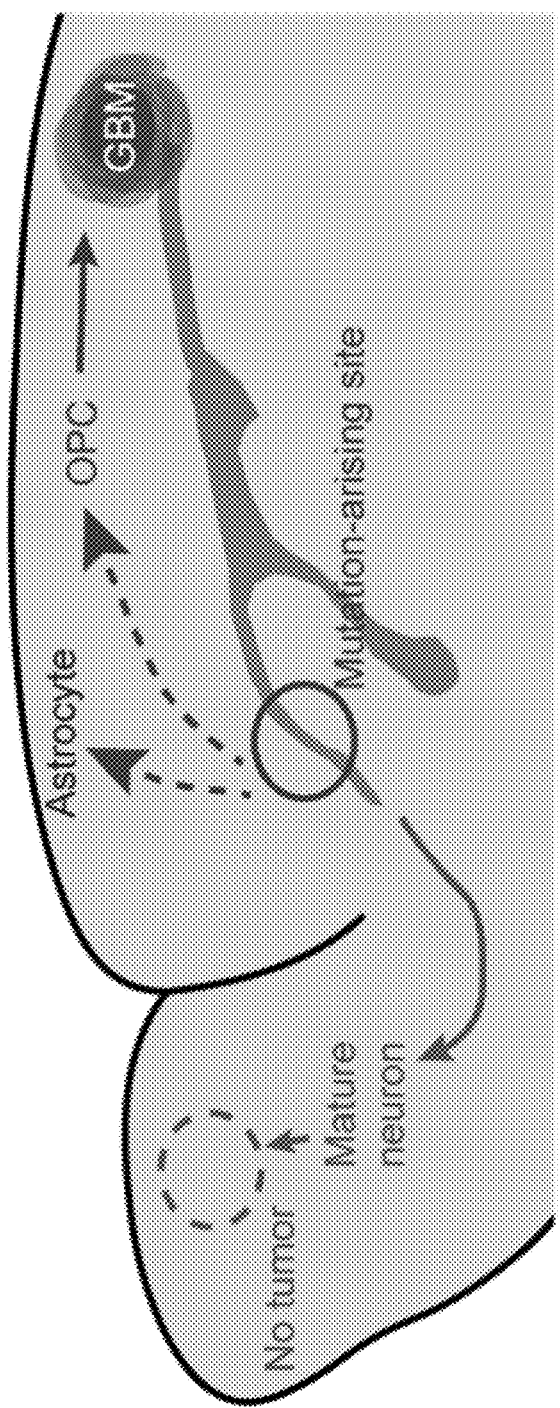
[FIG. 24]

[FIG. 25a]

[FIG. 25b]
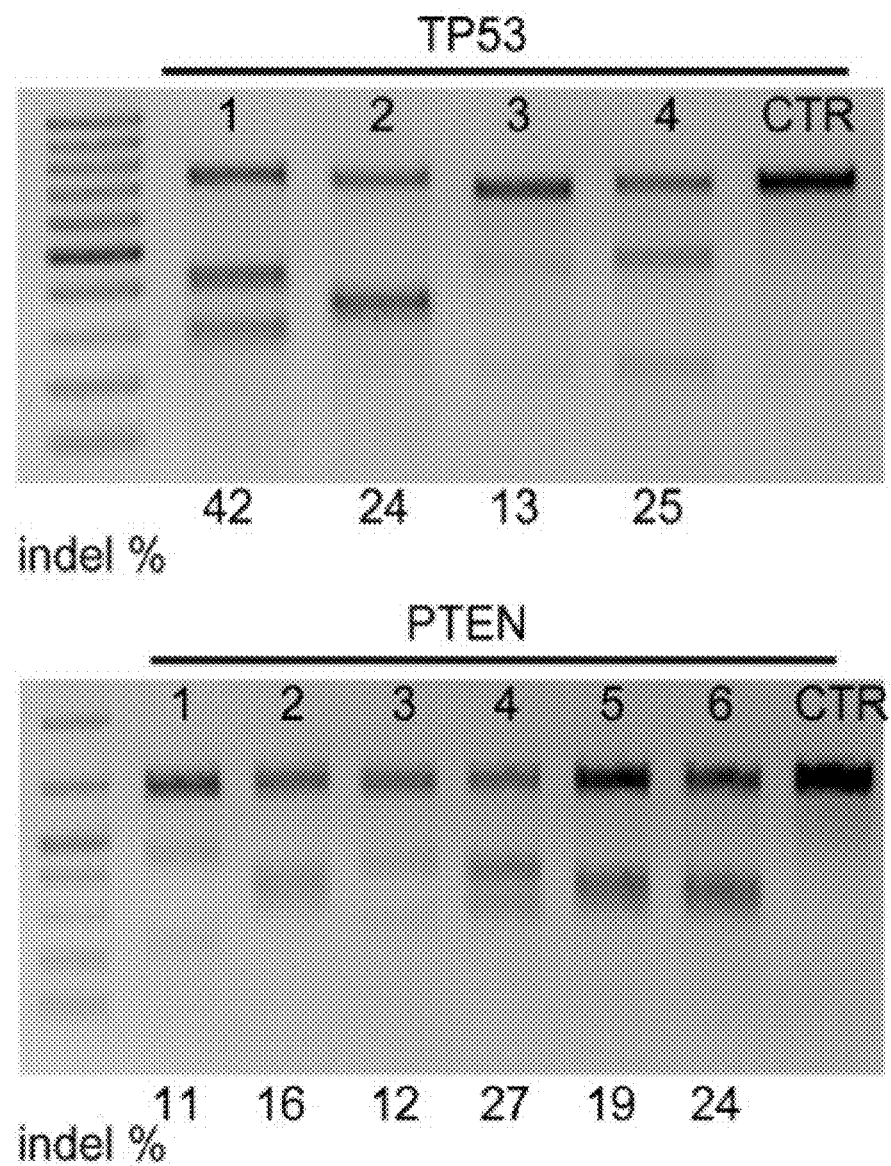

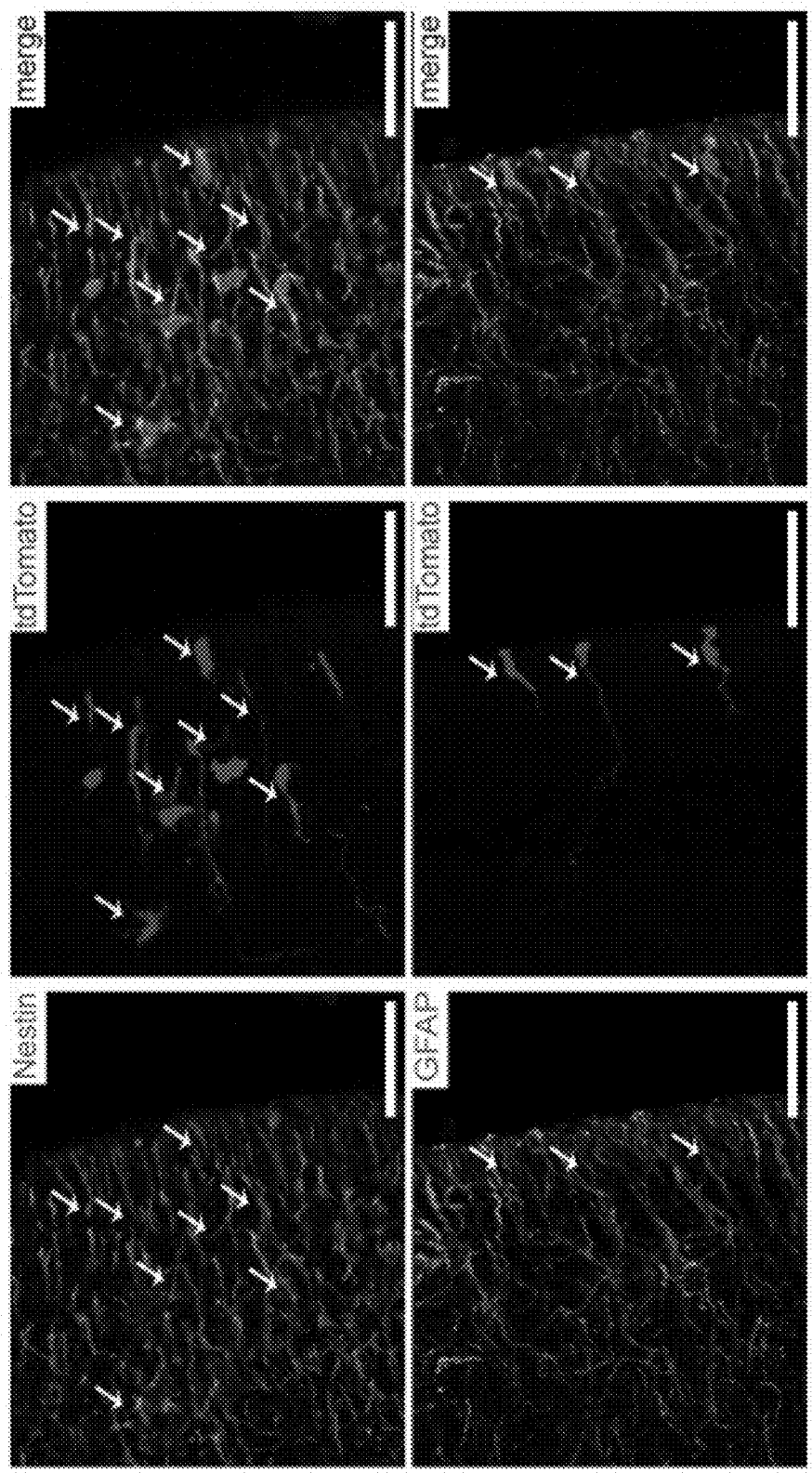
[ FIG. 25c ]

[FIG. 25d]
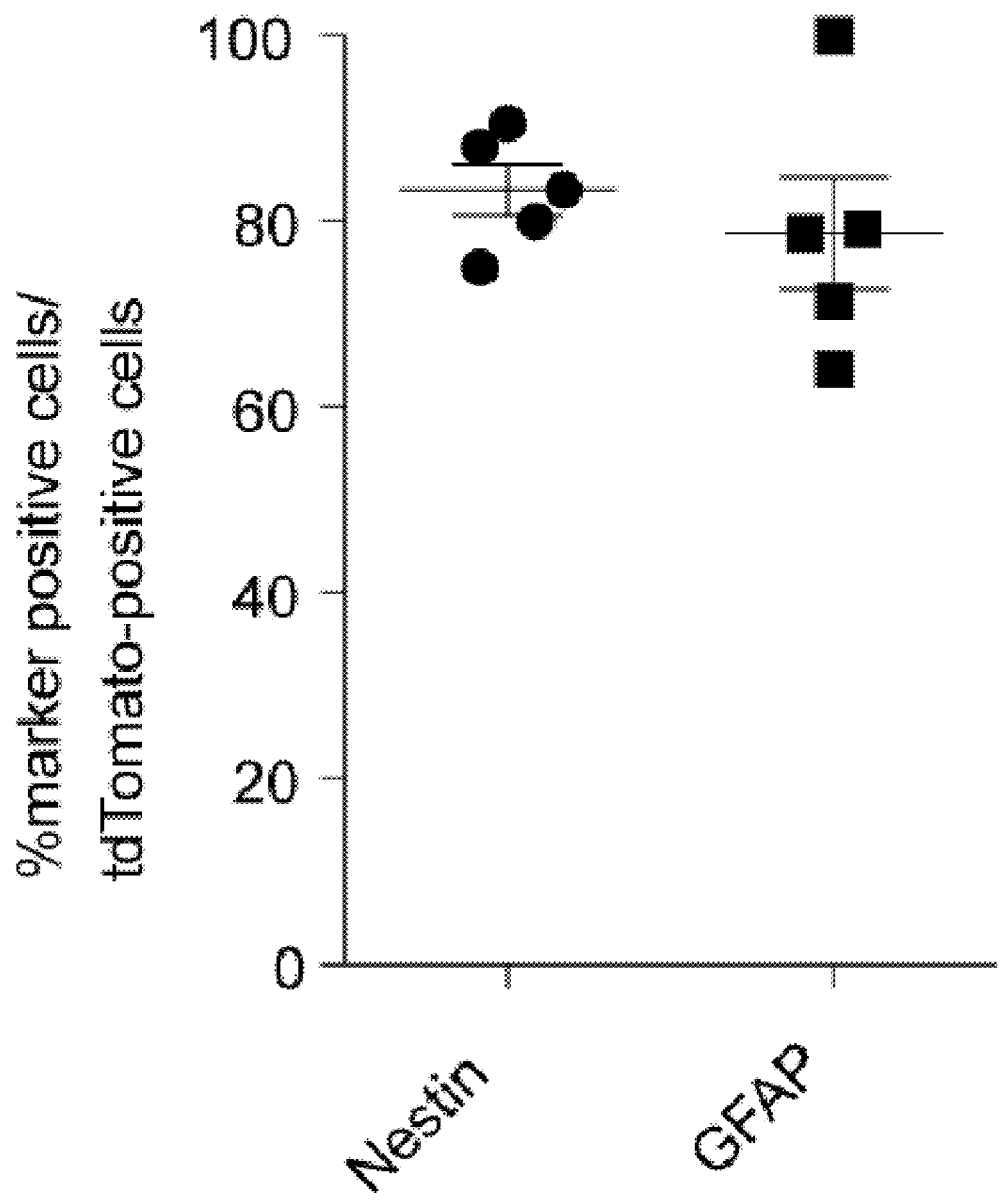

[FIG. 25e]
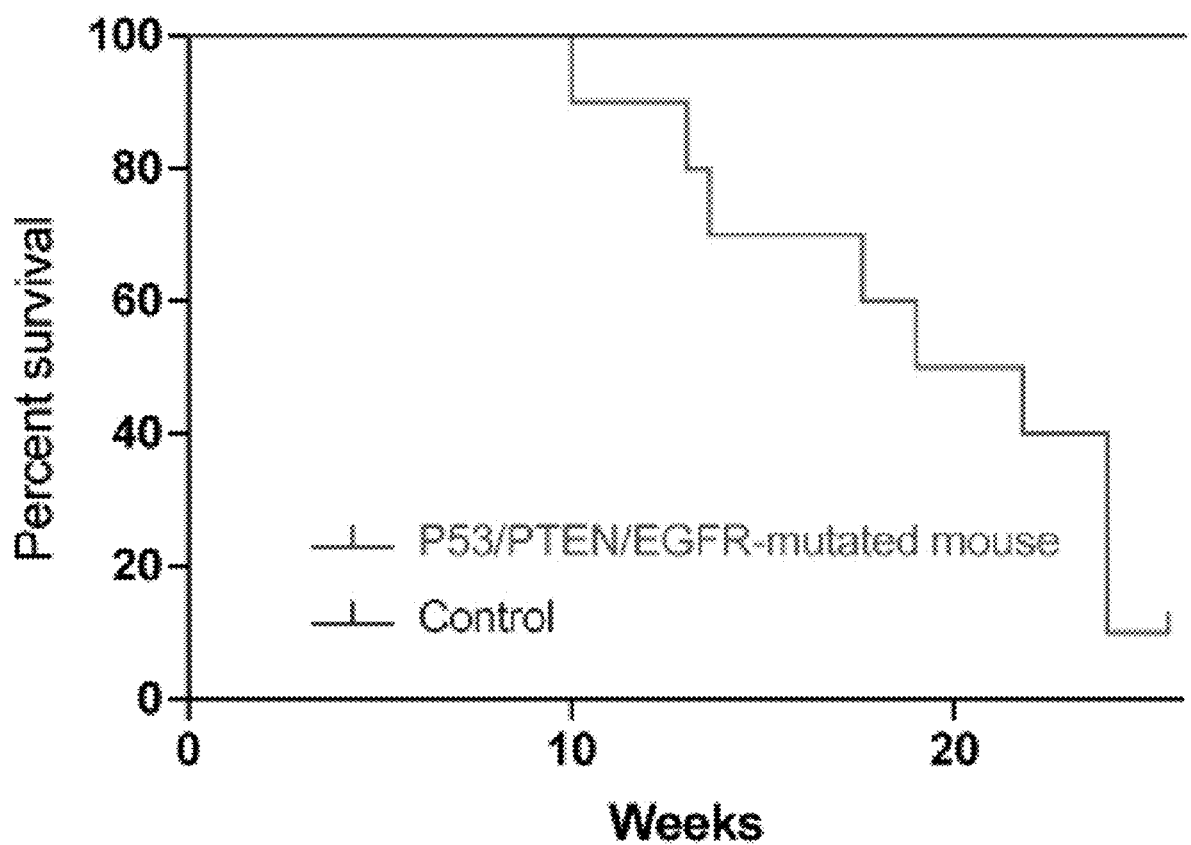

[FIG. 25f]
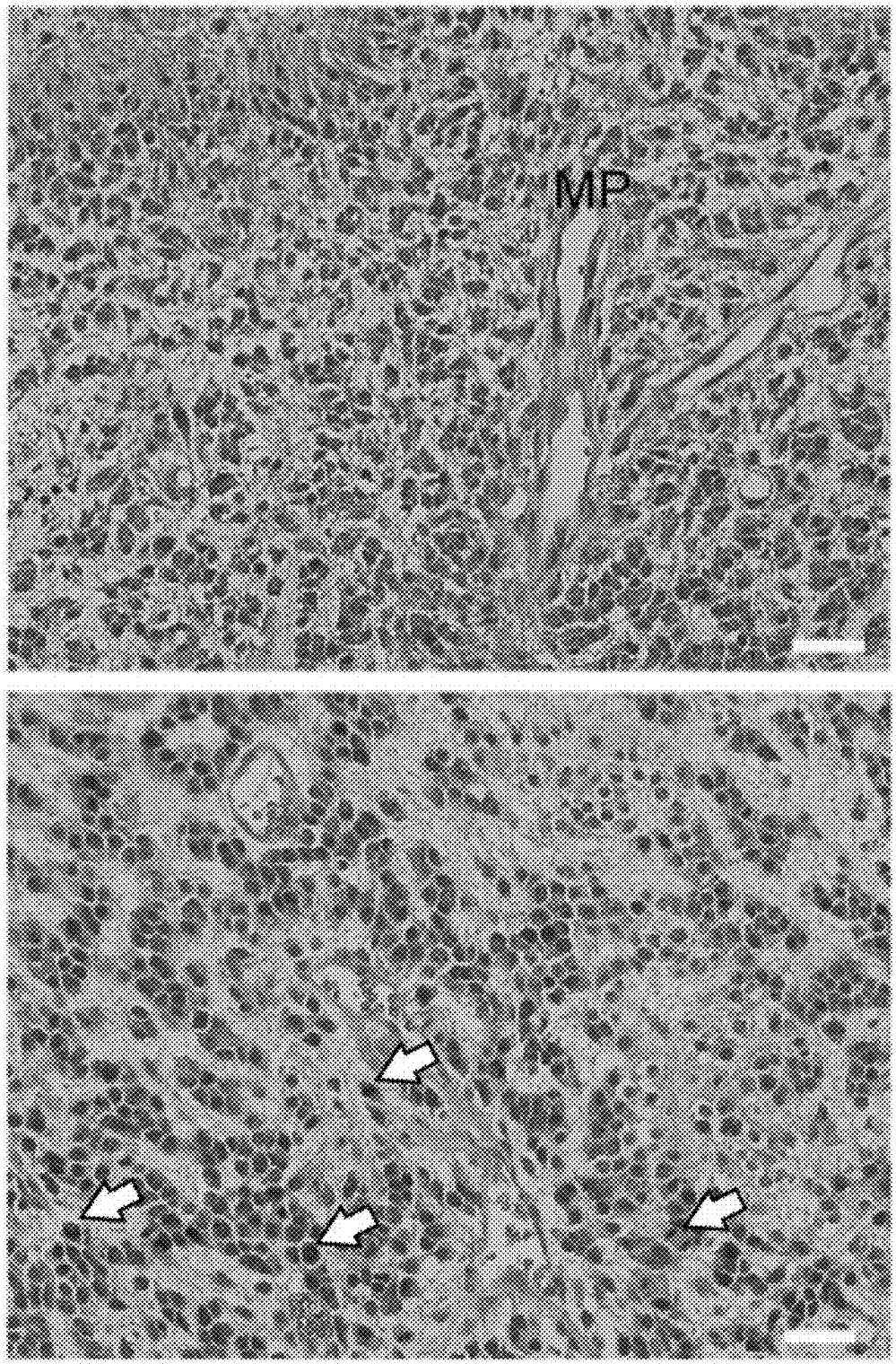

[FIG. 25g]

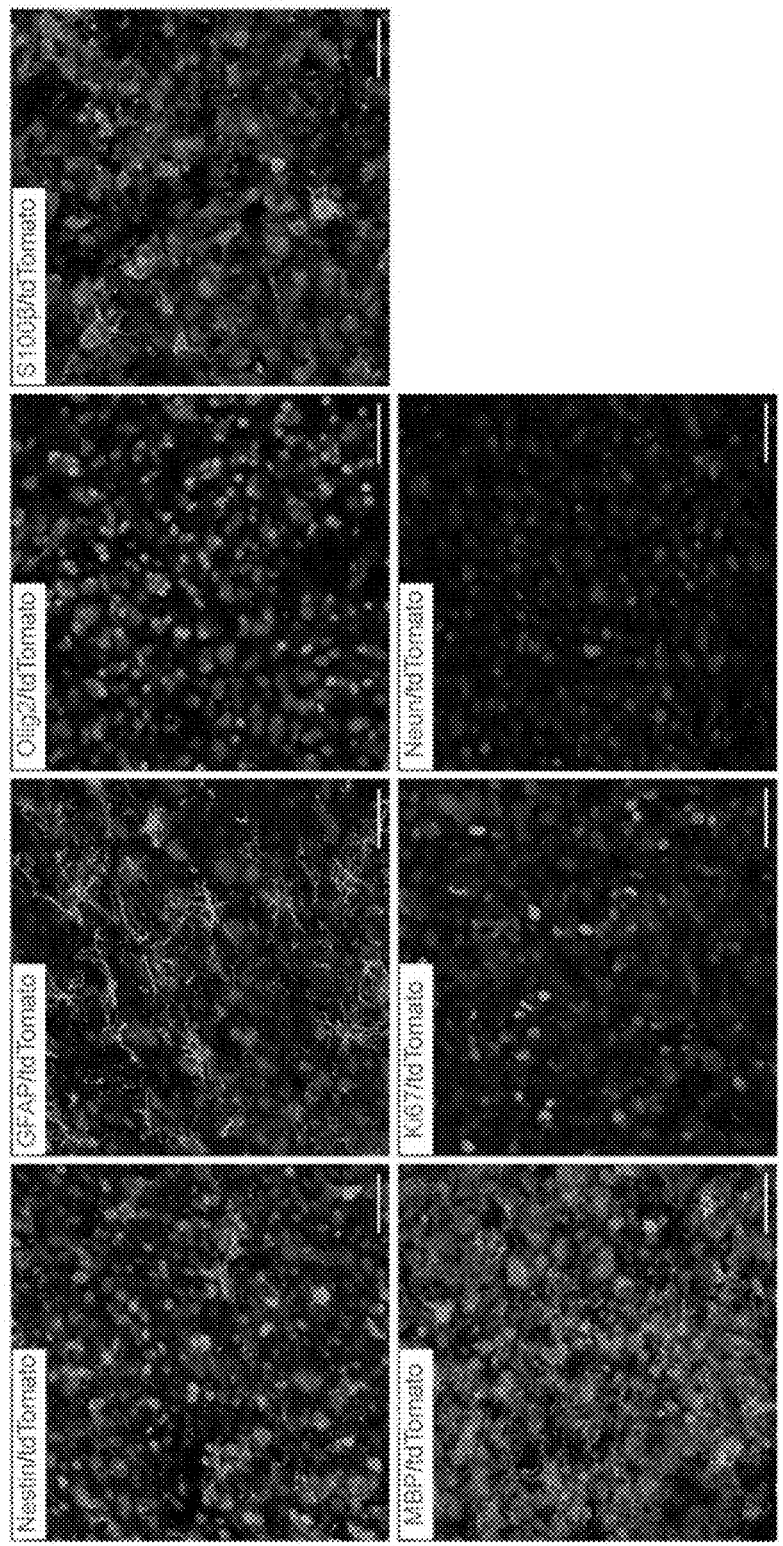
[FIG. 25h]

[FIG. 25i]
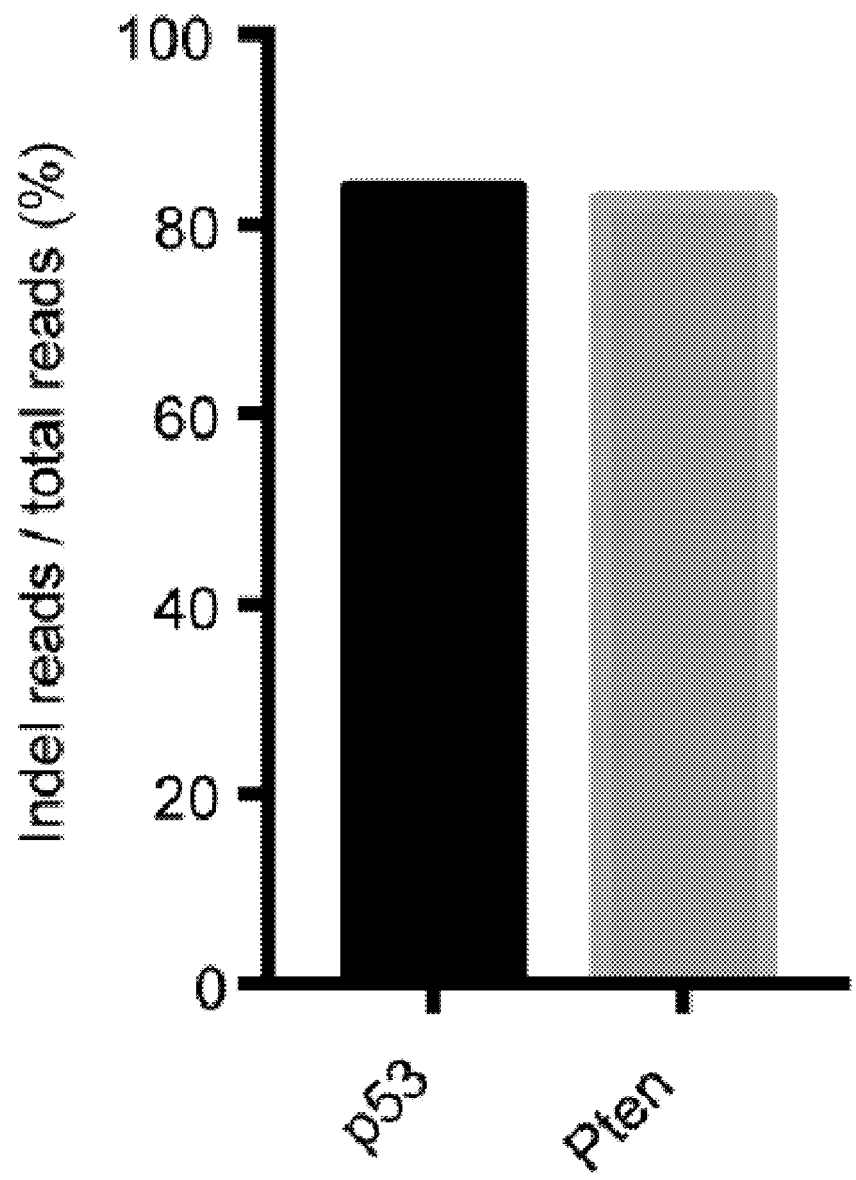

[FIG. 25j]
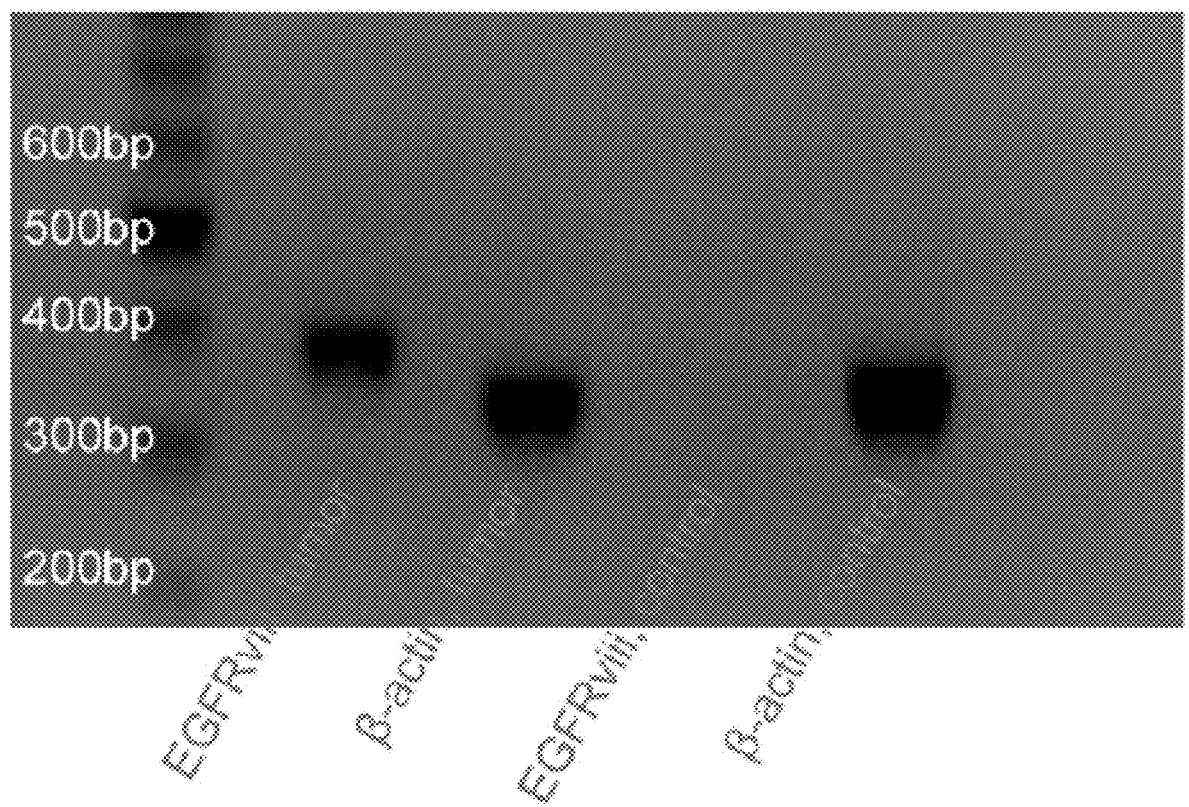

ANIMAL MODEL OF BRAIN TUMOR AND MANUFACTURING METHOD OF ANIMAL MODEL

TECHNICAL FIELD

The present invention relates to a transgenic animal having glioma and a method of preparing the same.

BACKGROUND ART OF THE INVENTION

A glioma is a tumor which accounts for 60% of primary brain tumors. The glioma is a malignant tumor which is highly likely to occur and difficult to be treated, and still does not have any special treatment besides radiotherapy. A glioblastoma (GBM), classed as the most malignant type in glioma, has very high resistance to radiotherapy and chemotherapy compared to other cancers, and patients can survive only 1 year after diagnosis. Therefore, the proper diagnosis and understanding for the origin and process of each patient with GBM are important.

In addition, in case of the brain tumor, a therapeutic drug is difficult to be delivered to target region of brain due to the brain blood barrier, and the neurobiology of the brain is a relative lack of understanding, thereby preventing the active development of a therapeutic agent. Furthermore, glioblastomas present an aggressive variant when compared to other brain tumors, which can result in catastrophic results within weeks if not treated within a short time.

Accordingly, radiotherapy and chemotherapy are performed to treat glioblastoma along with surgical treatment. However, there is no perfect treatment due to resistant variants, and re-occurrence caused by tumor stem cells. Therefore, it is necessary to develop an early diagnosis and understanding of origins and new therapeutic methods based on them.

In order to develop such a therapeutic method, it is urgent to develop an animal model that can reflect the phenomenon in a human patient. Studies of these animal models are expected to pinpoint the mechanisms of brain tumors and play an important role in verifying the effectiveness of various new therapeutic targets and new therapies.

DISCLOSURE

Technical Problem

An object of the present invention is a method for predicting a tissue origin of brain tumors by comparing the expression level of oncogene mutation in the subventricular zone (SVZ) and the expression level of oncogene mutation in brain tumor tissue.

Another purpose of the present invention is related to a method to providing information to decide target site to treat brain tumor effectively by estimating tissue origin of brain tumor.

It is another object of the present invention to provide information for determining a target site capable of effectively treating a brain tumor by predicting the tissue origin of a brain tumor.

It is another object of the present invention to provide a transgenic animal having glioma, more specifically, a brain tumor model animal having p53, Pten, and EGFR mutations specifically for neural stem cells in the subventricular zone, and a method for producing the same.

A further object of the present invention is a use of a brain tumor animal model for screening a therapeutic agent by testing the efficacy of a candidate agent using a brain tumor model animal.

Technical Solution

The present invention is related to a method to predict tissue origin of a brain tumor of unknown primary site by identifying mutations of oncogenes. More particularly, the present invention is related to a method to predict tissue origin of brain tumor comprising a step that measuring allele frequency of mutations at least one of the TERT C228T and TERT C250T in subventricular zone tissue and brain tumor tissue of target individuals following a step that determining the tissue origin of brain tumor is originated from SVZ when the mutations are shared by SVZ tissue and brain tumor tissue, and when the allele frequency of mutations in the SVZ are lower than the levels in brain tumor tissue.

The present invention is related to a brain tumor animal model that directly reflects the phenomenon in human patients and a preparation method the same, more specifically, a brain tumor animal model that mutations are introduced into p53, Pten, and EGFR genes, and a screening method of a therapeutic agent for brain tumor using the animal model, and a preparing method thereof.

The present invention allows to establish an appropriate therapeutic strategy by determining treating target site that maximize treating effect for the brain tumor according to the predicted tissue origin by comparing the expression level of mutant oncogenes between the subventricular zone and the brain tumor tissue.

Glioblastoma (GBM) is a type of incurable brain tumors and patients diagnosed with GBM can live only 15 months on average. It is able to step further in understanding of GBM disease and developing novel methods for treatment by identifying the origin cell having mutation causing GBM. Accumulation of somatic mutations can cause gliomagenesis, and neural stem cells (NSCs) which have capacities of self-renewal and proliferation in the adult human SVZ can be the cells which GBM originates from. However, there has been no explanation based on direct genetic evidences so far about that.

Accordingly, the present inventors reached the present invention by discovering that the astrocyte-like NSCs in the SVZ are the origin cells of human IDH-wildtype GBM by using human brain tissues and genome-edited mouse models.

In one embodiment of the present invention is related to a method to predict tissue origin of brain tumor comprising following steps:

(a) Measuring the allele frequency of at least one of the telomerase reverse transcriptase (TERT) 1,295,228 C>T (TERT C228T) and TERT 1,295,250 C>T(TERT C250T) mutant genes in the SVZ tissue of target individuals;

(b) Measuring the allele frequency of at least one of the TERT C228T and TERT C250T mutant genes in the brain tumor tissue of target individuals; and (c) Predicting the brain tumor is originated from the SVZ when the SVZ and brain tumor tissues are sharing the mutant genes at least one of TERT C228T and TERT C250T, and at least one of the TERT C228T and TERT C250T mutant genes according to the present invention are showing lower allele frequency in SVZ tissue than in brain tumor tissue.

In another embodiment of the present invention is related to a method of providing information to determine a target site for treating the brain tumor comprising following steps:

(a) Measuring the allele frequency of at least one of telomerase reverse transcriptase (TERT) 1,295,228 C>T (TERT C228T) and TERT 1,295,250 C>T(TERT C250T) mutant genes in the SVZ tissue of target individuals;

(b) Measuring the allele frequency of at least one of the TERT C228T and TERT C250T mutant genes in the brain tumor tissue of target individuals;

(c) Predicting the brain tumor is originated from the SVZ when the SVZ and the brain tumor tissues are sharing at least one of TERT C228T and TERT C250T mutant genes, and at least one of the TERT C228T and TERT C250T mutant genes according to the present invention are showing lower allele frequency in SVZ tissue than in brain tumor tissue; and (d) Determining the SVZ as the treating target site.

The term "treating target site" as used herein refers to a region or cells that anti-cancer treatments such as radiotherapy, chemotherapy, or immunotherapy are intensively applied to treat brain tumor effectively.

In the present invention, the expression levels of at least one mutant gene selected from the group consisting of EGFR (Epidermal growth factor receptor) mutant, TP53 (Tumor protein p53) mutant, PTEN (Phosphatase and tensin homolog) mutant, and Rb1 (Retinoblastoma 1) mutant can be measured additionally not only TERT C228T and TERT C250T.

In the present invention, measuring the expression levels of the EGFR mutants, TP53 mutants, PTEN mutant, and Rb1 mutant can be a process to identify whether the mutants are exist and their expression levels, preferably, variant allele frequency (VAF) or copy number variation (CNV) can be measured. In the present invention, VAF of at least one mutant selected from the group consisting of EGFR mutant, TP53 mutant, PTEN mutant, and Rb1 mutant can be measured and the CNV of the EGFR mutants can be measured.

The term "target individual" as used herein can refer to, but not limited to, a patient having or suspecting to brain tumor who need or be expected an appropriate treatment for brain tumor.

In the present invention, the "brain tumor", the object of the origin prediction, can be glioma, more preferably, glioblastoma, most preferably, isocitrate dehydrogenase (IDH)-wild-type (WT) primary glioblastoma.

In the present invention, the term "glioblastoma (GBM)" as used herein refers to a primary tumor arose from brain spinal cord tissue or its surrounding membrane area, and it is the tumor originated from a neuroglia cell which is abundantly present in normal brain tissue. In the present invention, the majority of the glioblastoma (>90%) are primary tumors arising without precursor disease before, on the other hand, the secondary glioblastoma are rare diseases and can be arisen and progress from low-grade astrocytoma. Most of secondary glioblastoma have IDH mutants, but the IDH mutants hardly ever exist in primary glioblastoma.

In the present invention, the term "subventricular zone (SVZ)" refers to a region situated throughout the lateral walls of lateral ventricles where nearly contact with ventricular layer. SVZ has characteristics that not only the proliferating cells are gathered in but also it is consisting of variety cells in diverse maturity stages.

In the present invention, the SVZ tissue and brain tumor tissue separated from the target individual can be, but not limited to, positioned at a distance of 1 to 40 mm, 3 to 35 mm, or 5 to 30 mm from one another.

In addition, the SVZ separated from the target individual in the present invention, can be separated from arbitrary regions of SVZ, preferably from astrocytic ribbon of SVZ, and more preferably comprising the astrocyte-like NSCs in the astrocyte ribbon, to improve accuracy of estimating tissue origin.

In the present invention, after the SVZ and brain tumor tissues were prepared, the allele frequency can be measured for at least one of TERT C228T and TERT C250T mutations, preferably TERT C228T as the tumor-inducing TERT promoter mutant in each tissue.

In the present invention, the "TERT 1,295,228 C>T (C228T)" and "TERT 1,295,250 C>T(C250T)" refer to the mutations occurred on the promoter region of TERT (telomerase reverse transcriptase) gene in melanoma-prone family, especially C228T and C250T which are observed somatic cell mutation of TERT gene promoter frequently (Science 339(6122): 959-9). Specifically, the TERT C228T in the present invention, is the mutation that a nucleotide C located 124 bp upstream of the ATG start site of TERT is mutated to T, and can be also represented by 'c.-124C>T'. Additionally, the TERT C250T is the mutation that a nucleotide C located 146 bp upstream of the ATG start site of TERT is mutated to T, and can be also represented by 'c.-146>T'.

In the present invention, measuring allele frequency of the TERT C228T and/or TERT C250T mutants can be a process to identify the existence and expression levels of the mutations, preferably a variant allele frequency (VAF) can be measured.

In the present invention, the term "variant allele frequency (VAF)" as used herein refers to variants in the target site of tissue, for example, allele frequency of mutations. The term "allele frequency" as used herein refers to a relative frequency of the allele in a target site, and it can be represented by %.

In the present invention, VAF of the TERT C228T and/or TERT C250T mutants can be carried out by DNA-sequencing analysis. More specifically, target site of 200 to 350 bp are amplified by PCR using primers specific to the mutants, followed by measuring relative frequency (%) of the allele of TERT C228T and/or TERT C250T mutants. The PCR can be carried out, for example, but not limited to, by using a forward primer represented by SEQ. ID. No. 1 and a reverse primer represented by SEQ. ID. NO. 2.

Preferably, in the present invention, it can be predicted whether the disease arise or not through whether the product produced by PCR amplification using sense and antisense primers of micro RNA polynucleotide. The PCR conditions, length of sense and antisense primers can be modified on the basis of those known in the art.

In the present invention, after measuring the variant allele frequency for at least one of TERT C228T and TERT C250T mutants in SVZ and brain tumor tissues respectively, if the result shows the SVZ and brain tumor tissues share same mutant at least one of TERT C228T and TERT C250T, and the variant allele frequencies of the at least one of mutants are lower in SVZ than brain tumor tissue, it can be predicted the brain tumor is originated from the SVZ, preferably from the astrocytic ribbon of SVZ, and more preferably from the astrocyte-like NSCs in the astrocyte ribbon.

For example, in the present invention, the variant allele frequencies of at least one of TERT C228T and TERT C250T of the SVZ (VAF1) can be, but not limited to, 0 to 50%, 0 to 40%, 0 to 30%, 0 to 25%, 0 to 20%, 0 to 15%, or 0 to 10%.

In the present invention, the variant allele frequencies of at least one of TERT C228T and TERT C250T of the brain tumor tissue (VAF2) can be, but not limited to, 10 to 100%, 20 to 100%, 20 to 95%, 25 to 95%, or 25 to 90%.

In the present invention, the brain tumor tissue can be predicted that the origin is SVZ, preferably astrocytic ribbon of SVZ, and more preferably the astrocyte-like NSCs in the astrocyte ribbon, when the VAF2 which is measured variant allele frequencies of at least one of the TERT C228T or TERT C250T mutants from brain tumor, is 1 to 45 times, or 1.5 to 45 times (VAF2/VAF1 ratio is 1 to 50, 1 to 45, or 1.5 to 45) of VAF1 which is measured variant allele frequencies of at least one of the TERT C228T and TERT C250T mutants from SVZ.

Additionally, in the present invention, besides the TERT C228T and TERT C250T, the expression levels of at least one of mutants selected from the group consisting of EGFR (Epidermal growth factor receptor) mutants, TP53 (Tumor protein p53) mutants, PTEN (Phosphatase and tensin homolog) mutants, and Rb1 (retinoblastoma 1) mutants, can be measured additionally.

In the present invention, the term "p53" as used herein is one of tumor suppressor factors known to inhibit abnormal proliferation of cells and induce the death of cancer cells. The "p53" is represented as TP53 or expressed Trp53 in case of mouse gene.

In the present invention, measuring expression levels of mutations of EGFR, TP53, PTEN and Rb1 could be a process to identify whether the mutants are exist and expression levels, preferably VAF or CNV can be measured. In the present invention, the VAF of at least one of mutations of EGFR, TP53, PTEN and Rb1, and the CNV of the EGFR mutations can be measured.

In the present invention, the term "copy number variation (CNV)" as used herein refers to a type of structural variants in a genome that is amplification or deletion of DNA fragments over 1 Kb.

In the present invention, the mutations of EGFR, TP53, PTEN and Rb1 could be, but not limited to, represented as Table 1 below.

patient. The variants are shown in Table 1 above. The common mutations were identified in EGFR, TP53, PTEN and Rb1, particularly PTEN and Rb1 showed frameshift (fs).

Specifically, in the present invention, the VAF or CNV of EGFR mutants TP53 mutants, PTEN mutants and Rb1 mutants can be performed by DNA-sequencing analyze. More specifically, it can be performed by measuring relative frequency of variant alleles (%) of the mutations of EGFR, TP53, PTEN or Rb1 after PCR amplification of target site of 200 to 350 bp using the mutants-specific primers. The primer sets could be, but not limited to, SEQ. ID. No. 3 as a forward primer, and SEQ. ID. No. 4 as a reverse primer for amplifying the EGFR mutant gene-specific primers, SEQ. ID. No. 5 as a forward primer, and SEQ. ID. No. 6 as a reverse primer for the PTEN mutant gene-specific primers, SEQ. ID. No. 7 as a forward primer, and SEQ. ID. No. 8 as a reverse primer for the TP53 mutant gene-specific primers, and SEQ. ID. No. 9 as a forward primer, and SEQ. ID. No. 10 as a reverse primer for the Rb1 mutant gene-specific primers.

In the present invention, after measuring the VAFs or CNVs of at least one of mutants of EGFR, TP53, PTEN and Rb1 in the SVZ and brain tumor tissues respectively, if the result shows the SVZ and brain tumor tissues share same mutant at least one of mutants of EGFR, TP53, PTEN and Rb1 in the SVZ, and the variant allele frequencies of the at least one of mutants are lower in SVZ than brain tumor tissue, it can be predicted the brain tumor is originated from the SVZ, preferably from the astrocytic ribbon of SVZ, and more preferably from the astrocyte-like NSCs in the astrocyte ribbon.

In the present invention, the variant allele frequencies at least one selected from the group consisting of mutations of EGFR, TP53, PTEN and Rb1 (VAF3) in the SVZ can be, but not limited to, 0 to 40%, 0 to 30%, 0 to 25%, 0 to 100%, 0 to 15%, or 25 to 95%.

TABLE 1

| Gene | Reference No. | Mutation of amino acid | Mutation of nucleotides(CDS) | Chromosone | Start site | Termination site |
|---|---|---|---|---|---|---|
| EGFR | NM_005228.4 | Ala289Val (Substitution-Missense, position 289, A->V) (SEQ ID NO: 11) | C866T (Substitution, position 866, C->T) (SEQ ID NO: 12) | Chr7 | 55154129 (on Assembly GRCh38) 55221822 (on Assembly GRCh37) | 55154129 (on Assembly GRCh38) 55221822 (on Assembly GRCh37) |
| TP53 | NM_000546.5 | Cys176Tyr (Substitution-Missense, position 176, C->Y) (SEQ ID NO: 13) | G527A (Substitution, position 527, G->A) (SEQ ID NO: 14) | Chr17 | 7675085 (on Assembly GRCh38) 7578403 (on Assembly GRCh37) | 7675085 (on Assembly GRCh38) 7578403 (on Assembly GRCh37) |
| TP53 | NM_000546 | Glu285Lys (Substitution-Missense, position 285, E->K) (SEQ ID NO: 15) | G853A (Substitution, position 853, G->A) (SEQ ID NO: 16) | Chr17 | 7673767 (on Assembly GRCh38) 7577085 (on Assembly GRCh37) | 7673767 (on Assembly GRCh38) 7577085 (on Assembly GRCh37) |
| PTEN | COSM4943 | Val317fs*6 (SEQ ID NO: 17) | 950_954del (SEQ ID NO: 18) | Chr10 | 89720798 | 89720798 |
| PTEN | COSM4899 | Val317fs*3 (SEQ ID NO: 19) | 951_954del (SEQ ID NO: 20) | Chr10 | 89720799 | 89720799 |
| Rb1 | — | Lys202fs (SEQ ID NO: 21) | 606_607AG>A (SEQ ID NO: 22) | Chr13 | 48923158 | 48923159 |

In one embodiment of the present invention, gene variants common in normal SVZ cells and tumor tissue at a sufficient distance were identified in a human IDH-wildtype GBM In the present invention, the variant allele frequencies at least one selected from the group consisting of mutations of EGFR, TP53, PTEN and Rb1 (VAF4) in the brain tumor tissue can be, but not limited to, 10 to 100%, 20 to 30%, 0 to 25%, 0 to 20%, 0 to 15%, or 0 to 10%.

In the present invention, the brain tumor tissue can be predicted that the origin is SVZ, preferably astrocytic ribbon of SVZ, and more preferably the astrocyte-like NSCs in the astrocyte ribbon, when the VAF4 which is measured variant allele frequencies of at least one selected from the group consisting of mutations of EGFR, TP53, PTEN and Rb1 in brain tumor, are 1 to 50 times, 1 to 40 times, 1.5 to 40 times, 1.5 to 30 times, 1.5 to 25 times, 2 to 25 times, or 2 to 20 times (VAF4/VAF3 ratio is 1 to 50, 1 to 40, 1.5 to 40, 1.5 to 30, 1.5 to 25, 2 to 25 or 2 to 20) of VAF3 which is measured variant allele frequencies of at least one selected from the group consisting of mutations of EGFR, TP53, PTEN and Rb1 in SVZ.

In the present invention, the CNV1 of at least one mutant selected from the group consisting of mutations of EGFR, TP53, PTEN, and Rb1 in the SVZ can be, but not limited to, 0 to 30, 0 to 25, 0 to 20, 0 to 15 or 0 to 10.

In the present invention, the CNV1 of at least one mutant selected from the group consisting of mutations of EGFR, TP53, PTEN, and Rb1 in the brain tumor tissue can be, but not limited to, 10 to 200, 0 to 25, 10 to 180, 10 to 170, 10 to 160, or 10 to 150.

In the present invention, the brain tumor tissue can be predicted that the origin is SVZ, preferably astrocytic ribbon of SVZ, and more preferably the astrocyte-like NSCs in the astrocyte ribbon, when the CNV2 which is measured copy number variants of at least one selected from the group consisting of mutations of EGFR, TP53, PTEN and Rb1 in brain tumor, are 1 to 50 times, 1 to 40 times, 1.5 to 40 times, 1.5 to 30 times, or 2 to 30 times (CNV2/CNV1 ratio is 1 to 50, 1 to 40, 1.5 to 40, 1.5 to 30, or 2 to 30) of CNV1 which is measured variant allele frequencies of at least one selected from the group consisting of mutations of EGFR, TP53, PTEN and Rb1 in SVZ.

In another embodiment of the present invention is related to a pharmaceutical agent preventing recurrence of brain tumor comprising antibodies specific to proteins expressed by at least one mutations selected from the group consisting of TERT C228T, TERT C250T, EGFR Ala289Val, TP53 Cys176Tyr, TP53 E285K, PTEN Val317fs*6, PTEN Val317fs*3 and Rb1 Lys202fs.

In the present invention, if the brain tumor originated from SVZ, the possibility of recurrence of the brain tumor is very high. Accordingly, the present invention can prevent recurrence of the brain tumor effectively by treating, for example, antibodies specific to proteins expressed by at least one mutations selected from the group consisting of TERT C228T, TERT C250T, EGFR Ala289Val, TP53 Cys176Tyr, TP53 E285K, PTEN Val317fs*6, PTEN Val317fs*3 and Rb1 Lys202fs to the SVZ, preferably astrocytic ribbon of the SVZ, and more preferably the astrocyte-like NSCs in the astrocyte ribbon.

The therapeutic agents of the present invention preferably comprising at least one of antibodies specific to proteins expressed by TERT C228T and TERT C250T. Antibodies specific to proteins expressed by at least one mutations selected from the group consisting of EGFR Ala289Val, TP53 Cys176Tyr, TP53 E285K, PTEN Val317fs*6, PTEN Val317fs*3 and Rb1 Lys202fs can be included additionally.

In the present invention the antibody as used herein refers to antibodies showing specific binding with the proteins expressed by the mutations of the present invention. The antibodies can be prepared by conventional methods from proteins obtained by conventional cloning method that each marker genes are inserted to the expression vector. Partial peptides that can be produced by the proteins are also included, and the partial peptides of the present inventions comprise at least 7 amino acids, preferably at least 9 amino acids, more preferably at least 12 amino acids. The forms of antibodies of the present invention are not particularly limited, and includes polyclonal antibody, monoclonal antibody, or part of those while they have antigen binding activities. Furthermore, the antibodies of the present invention can include special antibodies such as humanized antibodies. The antibodies used to detect cancer diagnosis marker of the present invention include functional fragment of an antibody molecule as well as a complete form having full-length of heavy chain and full-length of 2 light chains. The functional fragment of an antibody refers to a fragment having at least antigen binding activity, such as Fab, F(ab'), F(ab')2 and Fv.

The antibodies of the present invention, a person skilled in the art can design the protein-specific antibody based on the amino acid sequence of the protein expressed from the mutant genes of the present invention. A monoclonal antibodies to the proteins can be used the one produced by conventional monoclonal antibody producing method in the art, or commercially available one. Additionally, polyclonal antibodies recognizing the proteins, instead of monoclonal antibodies can be used and produced by antiserum preparation method which is conventional in the art.

In the present invention, the term "prevention" as used herein refers to, but not limited to, actions inhibiting recurrence of symptoms of brain tumors using the therapeutic agents of the present invention, or every action as long as inhibiting or delaying recurrence of symptoms of brain tumors.

The therapeutic agents of the present invention can be administrated together with other anticancer drugs that allow enhancing the effect of recurrence inhibition and inhibition of brain tumor.

The anticancer drugs can be, but not limited to, at least one selected from the group consisting of nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate-chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temozolomide, busulfan, ifosfamide, cyclophosphamide, melphalan, altretamine, dacarbazine, thiotepa, nimustine, chlorambucil, mitolactol, leucovorin, tretinoin, exemestane, aminoglutethimide, anagrelide, navelbine, fadrozole, tamoxifen, toremifene, testolactone, anastrozole, letrozole, vorozole, bicalutamide, lomustine and carmustine.

In the present invention, the pharmaceutical agents can be formulated in a capsule, a tablet, a granule, an injection, an ointment, a powder, or a drink, and the pharmaceutical agents can be applied to humans.

The pharmaceutical agents of the present invention can be, but not limited to, formulated in the form of oral dosage forms such as powders, granules, capsules, tablets, aqueous suspensions, external preparations, suppositories, and sterilized injection solutions according to conventional methods. The pharmaceutical agents of the present invention can include a pharmaceutically acceptable carrier. For oral administration, the pharmaceutically acceptable carrier can include one or more of binders, lubricants, disintegrants, excipients, solubilizing agents, dispersing agents, stabilizers, suspending agents, pigments, fragrances, and the like. For injection, the pharmaceutically acceptable carrier can include one or more of buffers, preservatives, pain-relieving agents, solubilizing agents, isotonic agents, stabilizers, and the like. For local administration, the pharmaceutically acceptable carrier can include one or more of bases, excipients, lubricants, preservatives, and the like. The pharmaceutical composition according to the present invention can be mixed with the pharmaceutically acceptable carriers as described above to provide various formulations. For example, for oral administration, the pharmaceutical composition of the present invention can be prepared in the form of tablet, troche, capsule, elixir, suspension, syrup, wafer or the like, and for injection, the pharmaceutical composition can be prepared in the form of unit dosage ampoules or multiple dosage containers. In addition, the pharmaceutical composition of the present invention may be prepared as solutions, suspensions, tablets, capsules, sustained-release formulations, or the like.

Meanwhile, examples of carriers, excipients and diluents, which are suitable for formulation, include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil, or the like. In addition, the pharmaceutical composition of the present invention can further contain one or more of fillers, anticoagulants, lubricants, wetting agents, fragrances, emulsifiers, preservatives, and the like.

Routes for administration of the pharmaceutical composition according to the present invention include, but are not limited to, oral, intravenous, intramuscular, intra-arterial, intra-marrow, intrathecal, intracardiac, transdermal, subcutaneous, intraperitoneal, intranasal, intestinal intrarectal, local, sublingual and intrarectal routes. Oral or parenteral administration is preferred.

In the present invention, the term "parenteral" as used herein includes subcutaneous, intradermal, intravenous, intramuscular, intra-articular, intrabursal, intestinal, intrathecal, intralesional and intracranial injection or infusion techniques. The pharmaceutical agents of the present invention can also be administered in form of suppositories for rectal administration.

The dose of the pharmaceutical agents of the present invention can vary depending on the activity of a particular compound used, the patient's age, body weight, general health, sex, diet, administration time, administration route, excretion rate, drug combination, and the severity of a particular disease to be prevented or treated. The pharmaceutical agents can be administered at a dose of 0.0001-50 mg/kg/day or 0.001-50 mg/kg/day, depending on the patient's condition, body weight, severity of the disease, the form of drug, administration route and period. The pharmaceutical agents of the present invention may be administered once or several times a day. The dose does not limit the scope of the present invention in any way. The pharmaceutical agents according to the present invention can be formulated as pills, sugar-coated tablets, capsules, liquids, gels, syrups, slurries, or suspensions.

The present invention provides a method of preparing an animal model of brain tumor by inducing p53, Pten and EGFR mutations in SVZ of an animal, preferably a non-human animal.

In the present invention, the term "animal" as used herein refers to any mammals except humans preferably rodents such as mice, rats, guinea pigs, hamsters, more preferably mice. The animals include every age of animals including embryos, fetuses, neonates, and adults. The animals for use in the present invention can be provided by, for example, commercial sources.

In the present invention, the term "animal model" as used herein refers to a non-human animal having a disease whose form is very similar to the disease of human. By the physiological or genetic similarities between human and animals, the biomedical disease model animals provide materials for research of the various causes of diseases, the pathogenesis, and the diagnosis in the disease research. By studying the disease model animals, basic materials of finding the disease-related genes out, understanding interactions among genes, and determining the possibility of practical use can be provided.

The animal model of the present invention has a somatic cancer including brain tumor, for example, glioma or glioblastoma. Specifically, glioma or glioblastoma is occurred in the cortex region separated from SVZ having mutations. The SVZ region shows normal cell structures, and the NSCs having oncogenic mutations migrate from SVZ and induce glioma by abnormal growth of oligodendrocyte-precursor cells (OPCs). The glioma of the animal model was determined high grade glioma according to the hematoxylin and eosin staining (H&E staining) result of the tumor tissue that representing the characteristics such as microvascular proliferation and mitosis. The glioma of the animal model showed immunoreactivity to GFAP, Nestin, Olig2, and PDGFRα, and was developed by migration of neural stem cells (NSCs) having self-renewal and proliferative capacities in SVZ to dorsolateral side. The somatic oncogenic mutations, for example, Trp53, Pten, and EGFR mutants, are able to develop malignant glioma from NSCs in SVZ. Accordingly, the animal model using Trp53, Pten, and EGFR mutants have glioblastoma that reflects the phenomenons of human patients that the glioblastoma arose from GFAP-positive NCSs.

The method of preparing the animal model of brain tumor can comprise following steps: (a) preparing an epidermal growth factor receptor (EGFR) mutant animal; (b) preparing a vector knocking out p53 and Pten; and (c) injecting the vector prepared in step (b) into the subventricular zone (SVZ) of the animal prepared in step (a) by electroporation.

The brain tumor can be malignant glioma, preferably glioblastoma (GBM). The SVZ can comprise a neural stem cell in SVZ, preferably refers to NSCs in the SVZ. In one embodiment of the present invention, the brain tumor was arisen in 90% of mice, and their median survival was 20 weeks when the method of preparing the animal model of brain tumor was applied (FIG. 25e).

The step of preparing the EGFR mutant animal prepared in the step (a) may include a method to commercially purchase an animal having the target mutant. The EGFR mutant can be, for example, an EGFR knockout, preferably an EGFRviii mutant (FEBS J. 2013 November; 280 (21): 5350-70).

In one embodiment of the present invention, LoxP-Stop-LoxP EGFRvii f/+;LoxP-Stop-LoxP tdTomato f/+ were prepared by mating a LoxP-Stop-LoxP EGFRviii mouse (FVB strain) purchased from NCI mouse repository and a LoxP-Stop-LoxP-tdTomato mouse (C57BL/6) purchased from The Jackson Laboratory.

The vector knocking out p53 and Pten prepared in the step (b) described above may be a vector used in gene editing. For example, but not limited to, vectors for homologous recombination, TALEN, zinc finger nuclease (ZFN), or CRISPR-Cas9 can be used. A person skilled in the art can select any appropriate vector by needs regardless of types of vectors as long as the vector can knock out p53 and Pten.

In one embodiment of the present invention, the vectors knocking out p53 and Pten were CRISPR-Cas9 vectors comprising sgRNA targeting p53 or Pten respectively that had been prepared by recombining genome-editing tested sgRNA and a CRISPR-Cas9 vector (FIG. 25a).

The CRISPR-Cas9 vector can be used by synthesizing using methods well known in the art or by purchasing commercially.

The genome-editing test of sgRNA can be carried out by methods well known in the art. Preferably, the genome-editing efficiency may be calculated by T7 Endonuclease I assay (T7E1 assay; NEB) after transduction.

The genome-editing test of sgRNA can additionally include a process to calculate mutation frequency.

The sgRNA targeting p53 may comprise SEQ ID NO: 29, and the sgRNA targeting Pten may comprise SEQ ID NO: 30.

The genome-editing frequency of the sgRNAs can be, but not limited to, the mutation frequency of 30 to 99.9%, 40 to 99.9%, 45 to 99.9%, 50 to 99.9%, 55 to 99.9%, 60 to 99.9%, 65 to 99.9%, 70 to 99.9%, 75 to 99.9%, 80 to 99.9%, 85 to 99.9%, 30 to 95%, 40 to 95%, 45 to 95%, 50 to 95%, 55 to 95%, 60 to 95%, 65 to 95%, 70 to 95%, 75 to 95%, 80 to 95%, 85 to 95%, or 50 to 90%.

In the step (C) described above, genes are transferred specific to the SVZ, the NSCs region, by inserting the vector by electroporation. The electroporation method can overcome the risk that genes were transferred to the other regions besides the SVZ.

In the step (C) described above, dose of the vector can be, but not limited to, 0.1 to 10 ng, 0.1 to 8 ng, 0.1 to 6 ng, 0.1 to 5 ng, 0.1 to 4 ng, 0.1 to 3 ng, 0.1 to 2.7 ng, 0.1 to 2.5 ng, 0.5 to 10 ng, 0.5 to 8 ng, 0.5 to 6 ng, 0.5 to 5 ng, 0.5 to 4 ng, 0.5 to 3 ng, 0.5 to 2.7 ng, 0.5 to 2.5 ng, 1 to 10 ng, 1 to 8 ng, 1 to 6 ng, 1 to 5 ng, 1 to 4 ng, 1 to 3 ng, 1 to 2.7 ng, 1 to 2.5 ng, 1.5 to 10 ng, 1.5 to 8 ng, 1.5 to 6 ng, 1.5 to 5 ng, 1.5 to 4 ng, 1.5 to 3 ng, 1.5 to 2.7 ng, or 1.5 to 2.5 ng, preferably 2 ng. The amount of vector inserted can be appropriately modified according to the technical knowledge in the art as required.

In one embodiment of the present invention, the brain tumor arose in 90% of mice as the result of a pU6-sgP53-pU6-sgPTEN_CBh-Cas9-P2A-Cre plasmid injection to a LoxP-Stop-LoxP EGFRvii f/+;LoxP-Stop-LoxP tdTomato f/+ mouse. On the other hand, the brain tumor did not arise in mice simply electroporated a sgLacz-targeting CRISPR-CAS9 vector (control). Accordingly, the result suggests that the brain tumor was induced by the mutations inserted, not by the shock of electroporation.

The present invention provides an animal model of brain tumor that p53 Pten and EGFR mutations are induced to an animal, preferably any mammals except humans. More specifically, an animal model that the p53 and Pten knockout mutants are induced specific to the SVZ of EGFR knockout animal is provided.

The p53, Pten and EGFR mutations may correspond to mutations in human patient group. Preferably, the p53, Pten and EGFR mutations can be p53, Pten, and EGFR knockout mutations, for example, but not limited to, indels of few nucleotides or frameshift. The mutations can be freely selected within the range of objectives to lose the function of proteins encoded by p53, Pten and EGFR genes.

The loss of protein functions may include every following case: when the proteins do not expressed, when the proteins expressed but not active, and when the protein activities are significantly inhibited compared to the wild type proteins.

The animal model of the present invention may have the incidence of brain tumor with more than 50%, more than 60%, more than 70%, or more than 80%, for example, 50 to 100%, 60 to 100%, 70 to 100%, 75 to 100%, 80 to 100%, 80 to 100%, 85 to 100%, 50 to 99%, 60 to 99%, 70 to 99%, 75 to 99%, 80 to 99%, 85 to 99%, 50 to 95%, 60 to 95%, 70 to 95%, 75 to 95%, 80 to 95%, or 85 to 95%.

In one embodiment of the present invention, the brain tumor arose in 90% of mice that the CRISPR/Cas9 vector comprising sgRNA targeting Trp53, or Pten had been injected. On the other hand, the control group that sgRNA targeting LacZ had been introduced did not form the brain tumors. Accordingly, it is certified that the animal model provided by the present invention is suitable as a brain tumor model.

In one embodiment of the present invention, variants in sgRNA analyzed by amplicon sequencing represented the result that the frequency of Trp53 genes comprising one of SEQ ID NO: 38 to 40 were about 80%, and the frequency of Pten genes comprising one of SEQ ID NO: 41 to 43 were about 80%.

The average life span of the mouse models in the present invention may be 10 to 50 weeks, 10 to 40 weeks, 10 to 35 weeks, 10 to 30 weeks, 10 to 28 weeks, 10 to 25 weeks, 12 to 50 weeks, 12 to 40 weeks, 12 to 35 weeks, 12 to 30 weeks, 12 to 28 weeks, or 12 to 25 weeks.

The animal model of the present invention has a characteristic that the mutation insertion region and the tumor developing region are separated. Preferably, the tumor may be developed on the region migrated to dorsolateral from the region the mutation inserted, and the separation distance can be, but not limited to, 1 to 40 mm, 3 to 35 mm, or 5 to 30 mm.

The animal model of the present invention has a characteristic that the SVZ having the Trp53, Pten, and EGFR mutants shows mutant genotypes but their phenotype remains normal tissue. Accordingly, the mutation injected region may not develop tumors.

In the animal model of the present invention, the Trp53, Pten, and EGFR mutations can be present on the electroporation region, for example, specific to NSCs in SVZ.

In one embodiment of the present invention, high-grade glioma having characteristics such as necrosis, microvascular proliferation, and mitosis was observed by analyzing brain tumor of a mouse model (FIG. 20). Additionally the characteristics of human glioma having immunoreactivity to GFAP, Nestin, Olig2 and PDGFRα, more specifically characteristics that glioblastoma is developed from GFAP-positive NSCs in the SVZ was observed, and the high proliferation ability was identified by Ki67.

Specifically, the animal model of brain tumor provided by the present invention directly reflect phenomenon in a human patient that glioblastoma is developed from GFAP-positive NSCs in the human SVZ.

More specifically, the animal model of the present invention has a characteristic that the mutant cell of frontal SVZ the mutation injected migrates to dorsolateral direction and forms tumor, while the frontal SVZ the mutation injected remains normal tissue.

In one embodiment of the present invention, it was determined by using tdTomato marker that the SVZ that mutations were first injected keeps normal structure and still it comprises NSCs having the mutations at the same time. In other words, the NSCs-specific mutations in SVZ were remained after occurrence of glioma. The mutations were identified in the tdTomato-positive NSCs as the result of gene analysis after separating using laser microdissection. Consequently, because the genetic mutations in primary region were kept even after tumor development, this characteristic can be used for further researches such as a study about the function of the mutant stem cells left in primary region, molecular mechanisms, and screening a novel agent for treating or preventing brain tumor.

The animal model of brain tumor of the present invention can be effectively used for researches about the function of genes, molecular mechanisms of brain tumor, screening novel anti-brain tumor agents for preventing or treating.

Accordingly, as another embodiment, the present invention relates to a method of screening a therapeutic agent for brain tumor comprising the step of administering a candidate agent for brain tumor treatment to a glioma-induced animal, followed by confirming whether or not the brain tumor is alleviated or treated.

Specifically, the animal that induced brain tumor can be usefully used for screening a therapeutic agent of brain tumor by confirming whether or not the brain tumor is alleviated or treated under conditions with or without a candidate agent for brain tumor treatment. Any substances reducing brain tumor symptoms directly or indirectly can be selected as a brain tumor treating agent. In other words, a result of observing symptoms of brain tumor without a candidate agent of brain tumor, and a result of observing symptoms of brain tumor with a candidate agent of brain tumor are compared and the substance that brain tumor symptoms were reduced in the presence of the candidate agent compare to absence of the candidate agent can be predicted as the brain tumor treating agent.

The step confirming whether or not the brain tumor is alleviated or treated can comprise measuring the gene expression level or protein activity level of markers of brain tumor. The markers of brain tumor can be, but not limited to, at least one marker selected from the group consisting of NeuN, nestin, GFAP, OliG2, S100b, MBP and Ki67. A person skilled in the art can freely select any brain tumor marker known in the art.

The expression or activity levels of proteins can be measured at least one method selected from the group consisting of Western blotting, radioimmunoassay (RIA), radioimmunodiffusion, enzyme-linked immunosorbent assay (ELISA), immunoprecipitation (IP), flow cytometry, immunofluorescence, ouchterlony, complement fixation assay, and protein chip.

The step that measuring the expression or activity levels of proteins can be carried out by measuring mRNA transcription level. The mRNA may be mRNA transcribed from a gene encoding the protein, or mRNA transcribed from a gene targeted by the protein.

The mRNA level can be measured, but not limited to, by at least one method selected from the group consisting of polymerase chain reaction (PCR), reverse transcriptase PCR (RT-PCR), real-time PCR, RNase protection assay (RPA), microarray, and Northern blotting.

The administrating method of the candidate agent can be administrate by any routes selected by common knowledge in the art such as subcutaneous injection, intramuscular injection, ophthalmic ointment, eye drop, ear drop, inhalation, rectal administration, oral administration, sublingual administration, and transdermal administration.

In the present invention, the term "candidate agent" as used herein refers to a substance subjected to test as a therapeutic agent for brain tumor, preferably glioblastoma. The candidate agent may comprise any molecules such as an extract, a protein, an oligopeptide, a small organic molecule, a polysaccharide, a polynucleotide and a compound in broad range. The candidate agent can also comprise a synthetic substance as well as a natural substance.

Effect of the Invention

The present invention provides an animal model of brain tumor and a preparation method thereof. More specifically, an animal model that directly reflects the phenomenon in a human patient that glioblastoma is occurred from GFAP-positive neural stem cells in human SVZ, and a method of preparing the same are provided. The animal model and the preparation method can be usefully applied in a diagnosis method of human brain tumor, screening a therapeutic agent and developing a novel drug.

Additionally, the present invention can predict the tissue origin of brain tumor of unknown primary. Accordingly, the present invention allows establishment of an appropriate treatment strategy by determining a target region of treatment that maximize treating effect of the brain tumor.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 1 is a schematic presentation for deep sequencing analysis using samples separated from IDH-wildtype BGM patients in one embodiment of the present invention.

FIG. 2 is a picture of the sampling sites of GBM tumor samples and tumor-free SVZ tissue samples in IDH-wildtype GBM patients (left) and a 3D-reconstructed MRI image showing the distance between the tumor-margin and the sampling site of SVZ tissue (right) in one embodiment of the present invention.

FIG. 3 shows VAFs scatterplots of mutations in SVZ tissues without tumor and GBM tumor tissues of 2 patients of IDH-wildtype GBM (GBM187, GBM26) in one embodiment of the present invention.

FIG. 4 shows VAFs scatterplots of mutations in SVZ tissues without tumor and GBM tumor tissues of 4 patients of IDH-wildtype GBM (GBM245, GBM276, GBM499, GBM520) in one embodiment of the present invention.

FIG. 5 is a table showing VAFs of mutations measured in SVZ tissues without tumor and GBM tumor tissues of IDH-wildtype GBM patients in one embodiment of the present invention.

FIG. 6 is a VAFs scatterplot of mutations in SVZ tissue without tumor and GBM tumor tissue of a patient of IDH-mutant GBM (GBM160) in one embodiment of the present invention.

FIG. 7 is a VAFs scatterplot of mutations in SVZ tissue without tumor and meningioma tissue of a patient of meningioma (MEN246) in one embodiment of the present invention.

FIG. 8 is a table shing VAFs of mutations measured in SVZ tissues without tumor and GBM tumor tissues of tumor patients except GBM, or patients GBM is invaded to SVZ (GBM146) and a IDH-mutant GBM patient (GBM261) in one embodiment of the present invention.

FIG. 9 is a bar graph representing VAFs of mutations shared in SVZ tissues presence or absence of GBM tumor in IDH-mutant GBM patients in one embodiment of the present invention.

FIG. 10 is a VAFs scatterplot of mutations in SVZ tissue without tumor and GBM tumor tissue of a patient of IDH-wildtype GBM that GBM is invade to SVZ (GBM146) in one embodiment of the present invention.

FIG. 11 is a bar graph representing VAFs of mutations shared in SVZ tissue without tumor and GBM tumor tissue of a patient of IDH-wildtype GBM that GBM is invade to SVZ (GBM160) in one embodiment of the present invention.

FIG. 12 is a graph showing CNVs results of EGFR mutants measured in GBM tumor tissue and tumor-free SVZ tissue of IDH-wildtype GBM patient in one embodiment of the present invention.

FIG. 13 represents a result of single cell Sanger sequencing for passenger mutation only in tumor and shared mutation in GBM tumor tissue and SVZ in an IDH-wildtype GBM patient (GBM185) in one embodiment of the present invention.

FIG. 14 represents a result of single cell Sanger sequencing for passenger mutation only in tumor and shared mutation in GBM tumor tissue and SVZ in an IDH-wildtype GBM patient (GBM520) in one embodiment of the present invention.

FIG. 15 shows the result of CNVs in tumor tissues and SNV tissues based on the deep WES data in one embodiment of the present invention. (a) The CNVs result in IDH-wildtype GBM patient having mutations in GBM tumor tissues shared with SVZ. (b) The CNVs result in IDH-mutant GBM patients and meningioma patients. (c) The CNVs result of a IDH-wildtype GBM patient that the GBM is invaded to SVZ.

FIG. 16 is a result of the laser capture microdissection (LCM) after deep amplicon sequencing in an IDH-wildtype GBM patient in one embodiment of the present invention.

FIG. 17 is the results of site-specific amplicon sequencing analysis relate to TERT C228T mutant in the microdissected astrocytic ribbon in one embodiment of the present invention.

FIG. 18 shows the mutation spectra incorporating the substitution type of mutations in GBM tumor tissue and tumor-free SVZ, and SVZ of IDH-wildtype GBM patient that GBM is invaded to SVZ in one embodiment of the present invention.

FIG. 19 is a graph showing contributions of signature 1, signature 5 and other signatures in GBM tumor tissue and tumor-free SVZ of IDH-wildtype GBM patients and GBM invaded SVZ of IDH-wildtype GBM patient GBM invaded in one embodiment of the present invention.

FIG. 20 shows the glioma progression in the mouse model carrying low-level driver mutations in NSCs from the SVZ in one embodiment of the present invention. (a) Experimental scheme showing the procedure for electroporation of a plasmid containing sgRNAs. (b) Representative images of serial sections from mice at 13 and 16 weeks after electroporation. (c)-(e) Representative images of immunostaining or H&E staining in P53/PTEN/EGFR mutant mice with high-grade glioma in the caudal cortex in one embodiment of the present invention.

FIG. 21 is a schematic showing the imaging analysis of tdTomato-positive cells in the caudal cortical region, and a graph representing quantification of the relative intensities of tdTomato signals in the caudal cortical regions at each time point in one embodiment of the present invention.

FIG. 22 is representative images of histology and MRI and the proportion of the location of the tumor in one embodiment of the present invention.

FIG. 23 is the representative immunostaining images of OLIG2-, PDGFRα-, GFAP- and tdTomato-positive cell regions at the caudal cortex, and the graph of propositions of the cells positive to neuron, oligodendrocyte, astrocyte, OPCs respectively in one embodiment of the present invention.

FIG. 24 is an illustration of the progress of migration and tumor development via the aberrant growth of OPCs in one embodiment of the present invention.

FIGS. 25a to j show development of high-grade glioma in genome-edited mice harboring P53/PTEB/EGFR mutations in the SVZ in one embodiment of the present invention. (a) The map of a single vector expressing Cas9 and Cre recombinase with the sgRNAs targeting p53/Pten. (b) In vitro screen of sgRNAs targeted to p53 and Pten in the Neuro-2a cell line. (c) Immunostaining image of neural stem cells at 3 days after electroporation. Scale bars, 50 um. (d) A scatter dot graph showing the percentage of tdTomato-positive cells co-stained with nestin or GFAP. (e) A Kaplan-Meier survival graph of mice (10 mice in each group, P=0.000063, log-rank test). (f) Representative H&E-stained images reflect the classical features of high-grade glioma, such as necrosis microvascular proliferation (M), and mitoses (arrow). (g) Representative MRI images of the 3 mice 16 weeks after the electroporation. (h) Immunostaining of various high-grade glioma-related markers, including nestin, GFAP, OLIG2, 100β, MBP and Ki67, as well as the neuronal maker NeuN, in tumors. (i) The bar graph shows the percentage of sequencing reads with indels in one high-grade glioma from mutant mice, using site-specific amplicon sequencing. (j) Detection of EGFRviii (360 bp) in tumors from mutant mice using qRT-PCR. Actb was used as an internal control.

MODES FOR INVENTION

Hereinafter, the present invention will be described in more detail through the Examples. The Examples are only for describing the present invention in more specifically. Based on the gist of the present invention, it will be obvious to those skilled in the art that the scope of the present invention is not limited by these Examples.

[Preparation Examples 1] Sample Preparation

To examine the somatic mutations in normal SVZ tissue away from the tumor mass, 55 specimens including i) pathologically and radiographically normal SVZ tissue with a safe distance from the tumor, ii) tumor tissue, and iii) unaffected normal cortical tissue or blood were obtained from 17 patients having isocitrate dehydrogenase (IDH)-wildtype GBM (primary GBM), IDH-mutant GBM (secondary GBM), or meningioma, oligodendroglioma, and mestatic cancer (FIG. 1).

The patients enrolled in our study underwent supra-total resection or other surgical resection of tumors located primarily in the temporal lobe, providing access to normal SVZ tissue away from the tumor mass, under the assistance of a magnetic resonance imaging (MRI)-based navigation system (FIG. 2). Tumor-free SVZ tissue was resected at a safe distance from the tumor margin on reconstructed three-dimensional MRI images, ranging from 5.3 to 33.3 mm. The collected SVZ samples were confirmed for tumor-free conditions by histological examination. In addition, the i) and iii) specimens described above were collected from two patients in whom GBM had invaded SVZs as a positive control.

[Preparation Examples 2] Gene Expression Microarray Datasets and Subtype Classification Total RNA was extracted from GBM tumour samples using a Qiagen RNeasy kit (Qiagen) according to the manufacturer's protocol. Expression profiles were obtained using an Illumina HumanHT-12 v4 Expression BeadChip. Raw data were variance stabilizing transformed normalized with the quantile normalization method using R/Bioconductor lumi package, and then standardized into [0, 1] by (values-MIN)/(MAX-MIN). The four gene signatures of GBM (Verhaak, R. G. W. et al. An integrated genomic analysis identifies clinically relevant subtypes of glioblastoma characterized by abnormalities in PDGFRA, IDH1, EGFR and NF1. Cancer cell 17, 98, (2010)) were projected onto the gene expression data. To determine the subtypes of samples, enrichment scores for each subtype were generated using single sample gene set enrichment analysis (ssGSEA).

[Preparation Examples 3] Deep Whole-Exome Sequencing (WES) in Patient's Tissues

Genomic DNA was extracted with either the Qiamp mini DNA kit (Qiagen) for freshly frozen brain tissues or the Wizard Genomic DNA Purification Kit (Promega) for blood following the manufacturers' instructions. Each sequenced sample was prepared according to Agilent library preparation protocols (Agilent Human All Exon 50 Mb kit). Libraries underwent paired-end sequencing on an Illumina HiSeq 2000 and 2500 instrument (average read depth of 392×) according to the manufacturer's protocol. The analysis-ready bam files from Fastq files were generated according to the 'best practices' workflow designed by the Broad Institute. In brief, raw sequences were aligned from the fastq file to reference genome using BWA (http://bio-bwa.sourceforge.net) to generate sam files. The sam files were converted to bam files and conducted the marked duplicate using Picard (http://broadinstitute.github.io/picard). Then, indel artefacts in these bam files were cleaned up using RealignerTargetCreator and IndelRealigner in GATK analysis tools (http://www.broadinstitute.org/gatk/download). Next, the present inventors performed base quality score recalibration using BaseRecalibrator in GATK analysis tools for the accurate variant calling.

[Preparation Examples 4] Deep Sequencing of Glioma-Related Genes

Hybrid capture probes for 79 glioma-related genes were designed using SureDesign online tools (Agilent Technologies). Glioma-related genes included TCGA GBM exome sequencing results of significantly mutated genes (allele frequency (AF)>2%) and meaningful genomic data (driver genes and functional pathways involved in grade II or III glioma) from large cohorts of grade II and III gliomas from Japan (JPN) and The Cancer Genome Atlas Research Network (TCGA) Consortium (Brennan, C. W. et al. The somatic genomic landscape of glioblastoma. Cell 155, 462-477, (2013); Suzuki, H. et al. Mutational landscape and clonal architecture in grade II and III gliomas. Nat Genet 47, 458-468, (2015)). Genomic DNA (>200 ng) was sheared, and the DNA fragments were end-repaired, extended with an 'A' on the 3' end, ligated with paired-end adaptors, and amplified (6 cycles). Adaptor-ligated libraries were hybridized for 24 h with biotinylated oligonucleotide RNA baits and enriched with streptavidin-conjugated magnetic beads. The final libraries were further amplified for 16 cycles with PCR and sequenced on an Illumina HiSeq 2500 sequencer (median read depth of 655×). Then, the present inventors generated an analysis-ready bam file using GATK best practice data cleanup pipeline. These bam files were converted to pileup files using Samtools (http://samtools.sourceforge.net).

[Preparation Examples 5] Site-Specific Amplicon Sequencing of Mutations in TERT Promoter A target region is designed to flank C228T and C250T mutations in TERT promoter, corresponding to c.-124C>T and c.-146C>T of TERT. This region was amplified by PCR using the primers (a forward primer: AGCACCTCGCGGTAGTGG; and a reverse primer: GTCCTGCCCCTTCACCTT (SEQ ID NO: 2)). This region was amplified by PCR using targeted primers, including six base-pair index sequences. PCR was performed using PrimeSTAR GXL (Takara, Japan) high-fidelity DNA polymerase under optimized thermal conditions. Then, DNA library was prepared according to the TruSeq DNA sample preparation guide. In brief, end repair and addition of 3'A overhangs were performed using the TruSeq DNA kit (Illumina, USA). Indexed TruSeq adaptors were ligated according to the manufacturer's protocol and purified with AMPure beads (Agencourt Bioscience, USA). DNA fragments of 386 bp (274 bp of DNA plus 55 bp of adaptors with 57 bp of index) were excised from agarose gel and purified using the Mini elute gel extraction kit (Qiagen, USA). Then, the present inventors performed enrichment of DNA fragments that had adaptor molecules on both ends to amplify the amount of DNA in the library using PCR primer cocktail and master mix (Illumina, USA). Libraries were pooled and sequenced on a Hiseq sequencer (IlluminaSA) (median read depth of 917,384×). Then, the present inventors sorted raw sequences from the Hiseq sequencer by index to generate patient-specific fastq files using in-house transcripts. The sorted sequences were aligned by Bowtie2 (http://bowtie-bio.sourceforge.net/bowtie2/index.shtml) and a bam file was generated. The bam file was converted to pileup files using Samtools (http://samtools.sourceforge.net).

[Preparation Examples 6] Validation Sequencing of Candidate Variants

To validate the candidate variants, the present inventors used Sanger sequencing of PCR-amplified DNA for variants. Primers for PCR amplification were designed with Primer3 (http://bioinfo.ut.ee/primer3-0.4.0/) (Untergasser, A. et al. Primer3Plus, an enhanced web interface to Primer3. Nucleic Acids Res 35, W71-74, (2007)). PCR was performed using PrimeSTAR GXL (Takara, Japan) high-fidelity DNA polymerase under optimized thermal conditions. PCR products were evaluated on agarose gels. Sanger sequencing was performed using Big Dye Terminator reactions and subsequent loading on an Applied Biosystems 3730 El DNA analyser (Applied Biosystems, USA). For the candidate variants with low variant frequency <10% or undetermined in Sanger sequencing, site-specific amplicon sequencing described above was used. The present inventors validated 104 (11.0%) out of 946 GBM-related mutations and randomly selected mutations, of which mutational burdens ranged from 1.9% to 99.1%. Of validated targets, the present inventors confirmed 96 out of 104 mutations. VAF calculated by site-specific amplicon sequencing replaced VAF of WES to analyse the clonal relationship between SVZs and tumors.

[Preparation Examples 7] Real-Time Quantitative PCR

Real-time qPCR was performed using iQ™ SYBR® Green Supermix (Biorad, USA) in the thermal cycler system (CFX-96, Biorad, USA) following the manufacturer's protocol. The presence of CNVs was confirmed using specific primers for the EGFR sequence, RNase P, and LDHA (Table 2) designed using Primer3 (http://frodo.wi.mit.edu). Thermal cycling consisted of one cycle with initial denaturation and enzyme activation at 95° C. for 3 min, followed by 40 cycles at 95° C. for 10 s and annealing and extension at 55-60° C. for 30 s. The relative fold changes, compared to blood or normal brain tissue, were determined using the relative normalized expression method calculated by CFX Manager™ Software.

The slides were deparaffinized with xylene and rehydrated. Heat-induced antigen retrieval was performed with 90° C. for 20 min in Tris-EDTA buffer. The slides were blocked in PBS-GT for 1 h at room temperature and stained with mouse antibody to GFAP (1:500; G3893, Sigma) and rabbit antibody to S100β (1:500; ab52642, abcam). Samples were then washed in PBS and stained with the secondary antibodies Alexa Fluor 488-conjugated to rabbit (1:500 dilution; Invitrogen) and Alexa Fluor 555-conjugated to mouse (1:500 dilution; Invitrogen). Samples were washed in PBS again and incubated in PBS with 300 nM DAPI. After performing immunofluorescence staining with GFAP, S100β antibodies, and DAPI, the ependymal layer, hypocellular gap, and dense ribbon of cell bodies in SVZs were identified microdissected with the PALM laser capture system (Carl Zeiss, Germany). Genomic DNA was extracted from collected cells using a QiAamp micro kit (Qiagen, USA). The target region flanking C228T mutation of TERT promoter was amplified by PCR using targeted primers and high-fidelity PrimeSTAR GXL DNA polymerase (Takara, Japan). Amplified PCR product was purified and then site-specific amplicon sequencing described in Preparation Examples 5 was performed.

[Preparation Examples 10] Analysis of Mutation Signature

To determine the contributions of mutational process, a multiple regression approach, deconstructSigs (Rosenthal,

TABLE 2

| Gene | Locus | Forward | Reverse | Product size |
|---|---|---|---|---|
| EGFR | Ch7: 55229262-55229347 | CGTCTCTTGCCGGAATGT (SEQ ID NO: 23) | GGATTAAAGAAATAACCTCCTACCC (SEQ ID NO: 24) | 86 |
| RNaseP | Chr15: 75246734-75246832 | GGGAGATGCGGAAGAATGT (SEQ ID NO: 25) | CCTCCAGTCAGCCACAGAA (SEQ ID NO: 26) | 99 |
| LDHA | Chr11: 18408413-18408534 | ACTGTGACCCTTATCCAGGC (SEQ ID NO: 27) | CTTCCCTTAACTAGCTCTCAGGA (SEQ ID NO: 28) | 122 |

[Preparation Examples 8] Single-Cell Cloning Preparation with Subsequent Sanger Sequencing Single nuclei were isolated from fresh frozen tumor samples. More specifically, tissue samples were placed in NST-DAPI buffer and teased apart and homogenized with scalpels. After free nuclei were confirmed visually using fluorescence microscopy, nuclei stained with DAPI were analysed by FACS. Single nuclei were sorted from the DAPI-positive population. For subsequent Sanger sequencing, the present inventors selected representative shared driver and tumor-private mutations with a high variant allele frequency in tumor samples. Two primer sets to flank the sites of tumor-private and shared mutations were designed using MPprimer (http://biocompute.bmi.ac.cn/MPprimer/). These mutation regions were amplified by multiplex PCR using the two primer sets. The single nuclei PCR was performed using HotStarTaq DNA polymerase (Qiagen, USA) under optimized thermal conditions.

[Preparation Examples 9] Laser Capture Microdissection (LCM)

Formalin-fixed, paraffin-embedded tissue sections from tumor-free SVZ were collected and placed on glass slides.

R., McGranahan, N., Herrero, J., Taylor, B. S. & Swanton, C. DeconstructSigs: delineating mutational processes in single tumors distinguishes DNA repair deficiencies and patterns of carcinoma evolution. Genome Biol 17, 31, (2016)) was performed to extract signatures based on the COSMIC signature framework (http://cancer.sanger.ac.uk/cosmic/signatures). Final inputs of mutations were 261 from 11 tumor-free SVZs, 812 from 9 GBMs, 60 from 1 GBM-invaded SVZ.

[Examples 1] Identification of Mutations in Tumor-Free SVZ and Tumor

The following experiments were performed based on a hypothesis that if the normal SVZ samples away from tumor obtained by the method of the Preparation Example 1, mutation burden or variant allele frequency (VAF) would be lower than tumor. Specifically, deep sequencing analysis were performed for the specimens of i) and iii) to identify low-level somatic mutations in the tumor-free SVZ. In briefly, deep whole exome sequencing (average read depth of 392X) in 34 samples, 2 telomerase reverse transcriptase (TERT) promoter site in 61 samples (average read depth or 948,608X), deep targeted sequencing in 79 glioma-related genes known by Cancer Genome Atlas Brennan, C. W. et al. The somatic genomic landscape of glioblastoma. Cell 155, 462-477, (2013); Suzuki, H. et al. Mutational landscape and clonal architecture in grade II and III gliomas. Nat Genet 47, 458-468, (2015))(Table 3) of 18 samples (average read depth of 601X) were performed. Recently, the mutations on upstream of 124 bp (C228T) and 146 bp (C250T) from TERT ATG start site are reported as oncogenes in 83% of GBM patients. And somatic mutations of all exons and TERT promoter sites were investigated using Strelka algorithm (https://sites.google.com/site/strelkasomaticvariantcaller/) and Integrative Genomic Viewer of aligned bam files, and VAFs were measured in SVZ and tumor tissue. Somatic mutations were not identified only in the samples from unaffected brain or blood tissue among specimens obtained from patients. Among tissues analyzed with deep WES, the present inventors identified an average of 25.2 somatic mutations in each tumor-free SVZ specimen and 86.3 in each tumor specimen. To validate somatic mutations, the present inventors performed Sanger sequencing or site-specific amplicon sequencing using primers described in Table 3 above, and 92.3% of selected somatic mutations (96 of 104) were identified as authentic somatic mutations. It is discovered that 47% of the patients (8 of 17) had at least one somatic mutation in the coding or TERT promoter region of tumor-free SVZs that was shared with the matched tumor by deep sequencing analysis (FIGS. 3, 4 and 5). Deep WES in the eight patients revealed that an average of 13.3 somatic mutations per individual was shared between matched tumor and tumor-free SVZ tissue. The shared somatic mutations in the tumor-free SVZ and the matched tumor tissue were only found in patients with IDH-wild-type GBM and not with other types of brain tumor (FIGS. 6, 7 and 8). More surprisingly, 75% (6 of 8) of the patients with IDH wild-type GBM who had somatic mutations shared between SVZ and tumor tissue contained low-level driver mutations in TERT promoter or cancer-driving genes, such as EGFR, PTEN and TP53 in their tumor-free SVZ tissue. VAFs of these mutations in SVZ were measured with 1% to 22%. Interestingly, the TERT promoter mutations were found in all of the IDH-wild-type GBM patients with driver mutations in tumor-free SVZ tissue. The VAFs of the driver mutations were measured much higher, about 29% to 92%, in tumor tissue than SVZ (FIG. 9). Meanwhile, deep WES in the patients with GBM-invaded SVZ showed that 93% of somatic mutations in tumor were appeared in somatic mutations in the GBM-invaded SVZs, and the VAFs of the mutations were higher in the SVZ than in tumor tissue (FIGS. 8, 10 and 11). Furthermore, the present inventors performed real-time quantitative PCR to analyze EGFR copy number variations (CNVs) often found in GBM and CNVs were found in the tumor-free SVZ tissue. The EGFR amplification was found in 4 of 6 patients of IDH-wild-type GBM patients having driver mutations in tumor-free SVZ tissue (Table 4). Similar to the results of deep WES, the relative EGFR copy numbers were measured significantly higher in tumor tissue than tumor-free SVZ tissue (FIG. 12).

Together, the results indicates that patients with IDH-wildtype GBM share somatic mutations in SVZ and tumor tissue, but the expression level in SVZ is significantly low than tumor tissue.

TABLE 3

| Glioma-related genes |
| --- |
| NOTCH1, NOTCH2, PDGFRA, EGFR, PIK3CA, PIK3R1, PTEN, NF1, CIC, ATRX, IDH1, FUBP1, ARID1A, ARID1B, SMARCA4, CDKN2A, TP53, SETD2, MLL2, IDH2, ABCB1, ABCC9, ADAM29, AFM, ANKRD36, BRAF, C1orf150, CALCR, CARD6, CD3EAP, CDH18, CDH9, CDHR3, CDX4, COL1A2, CXorf22, DCAF12L2, DRD5, DYNC1I1, FGA, FOXR2, FRMD7, GABRA1, GABRA6, GABRB2, GPX5, HEATR7B2, IL18RAP, KEL, KRTAP20-2, LCE4A, LRRC55, LUM, LZTR1, MMP13, NLRP5, ODF4, PARD6B, PLCH2, PODNL1, QKI, RB1, RFX6, RPL5, SCN9A, SEMA3C, SEMA3E, SEMG1, SIGLEC8, NRAS, KRAS, CDK4, CDKN2B, FGFR, MDM2, MDM4, MET, CDKN2C, CDK6 |

TABLE 4

| Patient no. | Distance between SVZ and tumor (mm) | Shared mutations | | |
| --- | --- | --- | --- | --- |
| | | SNV. Indel (VAF. SVZ → tumor) | TERT promoter (VAF. SVZ → tumor) | CNV (fold change, SVZ → tumor) |
| GBM 26 | 13.4 | EGFR:p.Ala289Val (3% → 48%) PTEN:p.Val317fs (2% → 35%) | c226 (1% → 37%) | EGFR (5 → 137) |
| GBM 187 | 18.8 | TP63:p.Cys176Tyr (7% → 92%) | c228 (2% → 42%) | * |
| GBM 245 | 7.2 | TP63:p.Glu285Lys (13% → 82%) | c228 (6% → 52%) | * |
| GBM 276 | 5.3 | * | c228 (2% → 33%) | EGFR (3 → 18) |
| GBM 499 | 7.6 | EGF:p.Ala289Val (4% → 28%) | c228 (1% → 38%) | EGFR (7 → 83) |
| GBM 520 | 26.6 | RB1:p.Lys202fs (18% → 39%) | c228 (1% → 36%) | EGFR (10 → 21) |

[Examples 2] Identification of Origin Region of GBM Tumor

About the result of Examples 1 that somatic mutations are shared in SVZ and tumor tissue of IDH-wild-type GBM patients, but the expression level in SVZ is much lower than in tumor tissue, it can be assumed that clones found in the SVZ gained tumor-private passenger mutations in a tumor development process after driver mutations had gained. The single cell sequencing of tumor sharing driver mutations with SVZ of IDH-wild-type GBM patients were performed, because tumors have to include not only mutations sharing with SVZ private passenger mutations in a single cell level, according to the assumption. More specifically, single nuclei were separated from a patient having a TP53, c.527G>A driver mutation in both of GBM tumor and SVZ and a TCERG1L, c.1127G>A passenger mutation only in GBM (GBM187) using fluorescence-activated cell sorting (FACS).

The VAFs of TP53, c.527G>A and TCERG1L, c.1127G>A were calculated in 91.8% and 87.2% which are similar to mutation level in tumor. And single cell sequencing was carried out for TP53, c.527G>A and TCERG1L, c.1127G>A regions. The result showed 42 of 47 sequenced clones had had both TP53, c.527G>A and TCERG1L, c.1127G>A mutations, 2 other clones had shown normal alleles in both regions (FIG. 13). Clones having either TP53, c.527G>A or TCERG1L, c.1127G>A mutants were not observed. Similarly, for tumors obtained from other IDH-wild-type GBM patient (GBM520), the VAFs of TERT promoter mutation C228T shared with SVZ and a RPS13, c.*3T>G private mutant of tumor were calculated as 36.0% and 40.8% respectively, 12 of 25 sequenced clones had had both of the mutations. Other clones had normal alleles in both regions (FIG. 14), and no clone had either one of 2 mutations. To investigate more the direction of clonal evolution, CNVs pattern were analyzed for all chromosomes in tumor-free SVZ and GBM-invaded SVZ using deep WES data. As a result, tumor-free SVZ did not show the structural abnormalities found in tumor, however, GBM-invaded SVZ showed SNV pattern identical with tumor tissue. Through, it was determined that tumor cells were not the origins of CNVs in tumor-free SVZ likewise single cell sequencing data (FIG. 15).

Accordingly, it is found that cells having driver mutations in tumor-free SVZ away from tumor were transformed and developed GBM.

[Examples 3] Determining Tumor-Driving Region and Cells in Tumor-Free SVZ

Next, the present inventors sought to determine which cell types in tumor-free SVZs harbor the mutations driving GBM. The human SVZ is known to comprise three anatomically distinct layers: the ependymal layer, hypocellular gap, and astrocytic ribbon. Of these three layers, the glial fibrillary acidic protein GFAP-positive, astrocytic ribbon in the SVZ contains astrocyte-like stem cells and the following experiments were carried out to determine whether astrocyte-like stem cells develop driver mutations in SVZ. First, S100β, GFAP, and DAPI immunostaining were performed in order to isolate separately the three layers of SVZ (FIG. 16). 2 patients of GBM499 and GBM198 were both represented low-level TERT promoter C228T mutation in tumor-free SVZ. Next, laser capture microdissection were performed to isolate separately GFAP-positive astrocyte-like stem cells from astrocytic ribbon, S100β-positive ependymal cells from ependymal layer, DAPI-positive cells from hypocellular gap or other regions (FIG. 16). To identify which cells have driver mutations in SVZ, the present inventors performed deep-site specific amplicon sequencing of the TERT promoter in enriched cells of each layer. The TERT promoter C228T mutation was noted only in GFAP-positive, astrocyte-like stem cells from the astrocytic ribbon layer (FIGS. 16 and 17).

Together, these results suggested that astrocyte-like stem cells from the astrocytic ribbon of the SVZ harbor driver mutations and clonally evolve to tumors away from the SVZ.

[Examples 4] Determining the Aetiology of Somatic Mutations in Tumor-Free SVZs

To examine the aetiology of somatic mutations in tumor-free SVZs, the present inventors attempted to analyse genetic signatures of the somatic mutations such as intrinsic DNA replication errors, exogenous or endogenous mutagen exposure and defective DNA repair. Mutational characteristics of somatic mutations were analyzed in coding regions of 11 tumor-free SVZs (271 somatic mutations), 9 tumors (845 somatic mutations), and 1 GBM-invaded SVZ (64 somatic mutations) discovered by each deep WES sequencing using DeconstructSigs (FIG. 18). Signatures 1 (33.9%) and 5 (45.4%) were found as major causes in mutation spectrum for tumor-free SVZ. Meanwhile, the Signature 1 was the only dominant signature in tumor (86.2%) and GBM-invaded SVZ (81.5%) (FIG. 19). High proportions of Signature 5 refers to accumulation of somatic mutations, not clearly discovered yet, it had been found that is caused by general genetic aging mechanisms recently. On the other hand, it had been found that high proportions of the Signature 1 refer to mutations based on rapid proliferation.

Together, it was found that somatic mutations in SVZ causing GBM affects natural aging of NSCs having limited self-renewal capacities rather than rapid proliferation of abnormal cells, by the result of high Signature 5 mutation level in tumor-free SVZ

[Examples 5] Preparing Mouse Model of GBM Tumor

To test whether low-level somatic mutations in the NSCs of the SVZ could indeed lead to the formation of GBM away from the SVZ in vivo, a mouse model of Trp53 (also known as p53 or TP53), Pten and EGFR mutations in NSCs from the SVZ through genome editing was prepared: these mutations were recurrent driver mutations found in the tumor-free SVZ tissues from the GBM patients.

5-1. Mouse Experiment Information and Preparation of LoxP-Stop-LoxP EGFRvii f/+;LoxP-Stop-LoxP tdTomato f/+ Mouse All mouse experiments were approved by and performed according to the guidelines of the Institutional Animal Care and Use Committee (IACUC) of the KAIST.

The mice were housed in isolator cages with free access to food and water. The housing room was located in a specific-pathogen-free condition maintained at a constant temperature of 23° C. on a 12-h light-dark cycle with lights off at 19:00. The health status of mouse was examined regularly by the veterinarians and investigators.

Disease Specific Survival (DSS) endpoint was met when the mice died or met the criteria for euthanasia under the IACUC protocol. The criteria for euthanasia were: (i) severe weight loss of more than 20%, (ii) severe neurological impairment including paralysis, seizure and hunched posture with impaired motor power, or (iii) head bulging sign.

A LoxP-Stop-LoxP EGFRvii f/+;LoxP-Stop-LoxP tdTomato f/+ mouse was prepared by mating a LoxP-Stop-LoxP EGFRviii mouse (FVB strain) purchased from NCI mouse repository and a LoxP-Stop-LoxP-tdTomato mouse (C57BL/6) purchased from The Jackson Laboratory 5-2. Construction of the Cre-Expressing CRISPR-Cas9 Vector In order to insert Trp53, Pten, and EGFR mutations to NSCs of mouse SVZ, a single vector containing sgRNAs targeting p53/Pten, Cas9, and Cre recombinase was generated.

Specifically, the pU6-(BbsI)_CBh-Cas9-T2A-BFP plasmid was obtained as a gift from R. Kuehn (Addgene plasmid 64323). sgRNAs targeting p53 (sgP53) and Pten (sgPTEN) were designed using CRISPRtool (http://crispr.mit.edu) to minimize potential off-target effects. sgRNA candidates for p53 and Lacz were designed by a method known in the art (Cancer Cell 28, 429-440 (2015)). sgRNA sequences are shown in Table 5.

TABLE 5

| SEQ ID NO: | Target gene | Sequence(5'->3') |
|---|---|---|
| 29 | Trp53 | GGTGTAATAGCTCCTGCATGG |
| 30 | PTEN | GGTTGGTCAAGATCTTCACAGA |
| 31 | LacZ | GGTGCGAATACGCCCACGCGAT |

Oligonucleotides containing each sgRNA sequence were synthesized by Cosmogenetech and annealed in vitro with a thermocycler. pU6-(BbsI)_CBhCas9-T2A-BFP plasmid was digested with BbsI and ligated with the annealed oligonucleotides.

The genome-editing test with plasmids containing sgRNAs was performed by a method known in the art (Nat. Protocols 8, 2281-2308 (2013)). In brief, Neuro-2a cells were transfected with the plasmids carrying sgRNAs candidates using jetPRIME transfection reagent (Polyplus). After 2 days, genomic DNA was extracted from the treated cells using the Qiamp mini DNA kit (Qiagen) and used as a template for PCR amplification of target regions. T7 Endonuclease I assay (T7E1 assay; NEB) was performed to test the genome-editing efficiency of sgRNA candidates. The T7E1 results shown in FIG. 25b. Mutation frequencies were calculated on the basis of the band intensities with ImageJ software and the following Formula.

$$\text{Mutation frequency (\%)} = 100 \times (1-(1-\text{fraction cleaved})^{1/2}) \quad \text{[Formula 1]}$$

To generate a single vector containing sgRNAs targeting p53/Pten, Cas9, and Cre recombinase, the present inventors amplified P2A-Cre with AAV:ITR-U6-sgRNA (backbone)-pEFS-Rluc-2A-Cre-WPRE-hGHpA-ITR (a gift from F. Zhang, Addgene plasmid 60226), and then switched T2A-BFP to P2A-Cre in the pU6-(BbsI)_CBh-Cas9-T2A-BFP plasmid. Next, the present inventors amplified pU6-sgP53, pU6-sgPTEN and switched pU6-(BbsI) to pU6-sgP53-pU6-sgPTEN in pU6-(BbsI)_CBh-Cas9-P2A-Cre plasmid to generate pU6-sgP53-pU6-sgPTEN_CBh-Cas9-P2A-Cre plasmid (sgTP-Cas9-Cre). In addition, the present inventors inserted sgLacz to pU6-(BbsI)_CBh-Cas9-P2A-Cre to generate sgLacz-Cas9-Cre. The final vector map was shown in FIG. 25a.

5-3. Insertion of Vectors to Mouse SVZ by Electroporation

The Cre-containing CRISPR-Cas9 vector generated by a method of Examples 5-2 was injected to front SVZ of one side of LoxP-Stop-LoxP EGFRviii f/+; LoxP-Stop-LoxP tdTomato mouse cerebral hemisphere by in vivo electroporation to induce oncogenic mutations to NSCs in specific regions of mouse SVZ and determine mutant cell migration from SVZ.

Specifically, neonate, 2-3-day-old pups (P2-P3) were anaesthetized by hypothermia (over 5 min) and fixed to a support using an adhesive plaster. As a general positional marker, a virtual line connecting the right eye with lambda was used and a capillary needle was inserted at about one-third the length of this line from the eye. The right lateral ventricle was injected at a depth of 2 mm from the skull with 1 μl of plasmid solution (2 ug/ul, containing 1% (v/v) FastGreen). Injection success was achieved with the Fast-Green staining visualizing the shape of the lateral ventricle. Only successfully injected animals were subjected to five electrical pulses (100 V, 50 ms, separated by 950 ms intervals) using the ECM830 electroportor (BTX-Harvard apparatus) and 1-mm tweezer electrodes (CUY650P1, Nepagene). The positive electrode was positioned ahead of the eye, and the negative was placed in the opposite position on the ventral side. After electroporation, mice were placed on a 37° C. heating plate until they fully recovered and were returned to their mother. The transfected cells expressing tdTomato were mainly located on the rostral-dorsolateral side in the anterior horn of the lateral ventricle at post-injection 2 days. However, the transfected cells decreased gradually to the caudal direction and disappeared at the coronal section of the rostral head of the hippocampus.

The immunostaining result of Trp53/Pten/EGFR mutant mice 3 days after electroporation is shown in FIG. 25c. White arrows pointing the regions tdTomato-positive reaction appeared with GFAP or nestin in SVZ. Therefore, it was confirmed that tdTomato-positive cells were localized in SVZ. A scatterplot of cells co-stained with tdTomato-positive and nestin or GFAP is shown in FIG. 25d.

5-4. Identifying Development of Brain Tumor in Mice Model

90% of the electroporated mice (9 of 10) developed brain tumors with a median survival of 20 weeks, whereas no brain tumors were found in control mice simply sgLacz-targeting CRISPR-Cas9 vectors were electroporated (FIG. 25e). The survival rate of electroporated mice compare to control mice is shown in FIG. 25e. 10 mice were used for each group.

Additionally, EGFRviii expression and Trp53 and Pten indels in brain tumor were examined Specifically, tumor mass separated with a scalpel and genomic DNA was extracted from tdTomato-positive cells in olfactory bulb which are microdissected using laser-microdissection. Trp53 and Pten region of mouse genome are amplified using primers listed in Table 6.

TABLE 6

| SEQ ID NO: | Primer Name | Sequence(5'->3') |
|---|---|---|
| 32 | Mouse_Trp53_forward | AGGTAGGGAGCGACTTCACC |
| 33 | Mouse_Trp53_reverse | TAAGGATAGGTCGGCGGTTC |
| 34 | Mouse_Pten_forward | AGACCATAACCCACCACAGC |
| 35 | Mouse_Pten_reverse | TACACCAGTCCGTCCCTTTC |

After amplification of target region, site-specific amplicon sequencing described in Preparation Examples 5 above was performed. To measure the frequencies of indels in the target regions, the Cas-Analyzer algorithm (http://www.rgenome.net/cas-analyzer/#!) was used. The indel frequency result is shown in FIG. 25i.

Specifically, indels were randomly generated near the sgRNAs targeting sites, and both Trp 53 and Pten showed high indel frequencies over 80%. More specifically, indels of Trp53 were randomly generated in range of 69402693 to 69402702 of chromosome 11, and indels of Pten were randomly generated in range of 32874403 to 32874412 of chromosome 19 (reference mouse genome: UCSC mouse standard genome).

The Table 7 below is showing the representative amplicon sequencing results of Trp53 and Pten which are sequences more than 1% of total reads. The read frequency of the Table 7 refers to the each read ratio having notated sequences to total reads.

TABLE 7

| SEQ ID NO: | Nucleotide sequence | Read frequency (%) |
|---|---|---|
| Trp53 | | |
| 38 | TGTGTCTTCCCCCAGGCCGGCTCTGAGTATACCACCATCCACTACAA GTACATGTGTAATAGCTCCTGCACTTGGGGGGCATGAACCGCCGACC TATCCTTA | 36.3 |
| 39 | TGTGTCTTCCCCCAGGCCGGCTCTGAGTATACCACCATCCACTACAA GTACATGTGTAATAGCTCCTGTGGGGGGCATGAACCGCCGACCTATC CTTA | 34.7 |
| 40 | TGTGTCTTCCCCCAGGCCGGCTCTGAGTATACCACCATCCACTACAA GTACATGTGTAATAGCTCCTGCAATGGGGGGCATGAACCGCCGACCT ATCCTTA | 8.0 |
| Pten | | |
| 41 | AGACCATAACCCACCACAGCTAGAACTTATCAAACCCTTCTTGAAGA TCTTGACCAATGGCTAAGTGAAGATGACAATCATGTTGCAGCAATTC ACTGTAAAGCTGGAAA | 38.9 |
| 42 | AGACCATAACCCACCACAGCTAGAACTTATCAAACCCTCTGAAGATC TTGACCAATGGCTAAGTGAAGATGACAATCATGTTGCAGCAATTCAC TGTAAAGCTGGAAA | 36.6 |
| 43 | AGACCATAACCCACCACAGCTAGAACTTATCAAACCCTTCGTGAAGA TCTTGACCAATGGCTAAGTGAAGATGACAATCATGTTGCAGCAATTC ACTGTAAAGCTGGAAA | 3.3 |

For the identification of EGFRviii expression in tumors, RNA was extracted from tumor and untreated brain tissue using RNeasy Mini Kit (Qiagen). Then, cDNA was generated from the extracted RNA using SuperScript II (Invitrogen). To amplify EGFRviii from the cDNA, the present inventors designed primers annealing to human EGFR exons 1 and 8. The sequences of the primers are as follows: forward, 5'-CCCAGGCACTTGATGATACTC-3'(SEQ. ID NO. 36) and reverse, 5'-CTTGCTTTGGGTGGAGAGTT-3' (SEQ ID NO: 37). The PCR conditions were as follows: 98° C. for 2 min; 35 times (98° C. for 10 s, 60° C. for 15 s, 68° C. for 30 s); hold at 4° C. Then, the amplicon was analysed by electrophoresis on 2% agarose gel. Actb was used as control. The electrophoresis result is shown in FIG. 25j. FIG. 25j is showing that EGFRviii was expressed only in tumors.

A gross mass of tumor was identified 16 weeks after electroporation. The MRI image is represented in FIG. 25g.

Specifically, MRI conditions are as follows. The mice were initially anaesthetized by inhalation of 5% isoflurane in an air/O2 mixture, and then placed in a cradle for MRI scans, with a respiratory mask connected to 1.5% isoflurane in an air/O2 mixture. MRI experiments were performed on an a 3T MRS 3000 scanner (MR Solutions) with a birdcage mouse head coil.

T1-weighted and T2-weighted images were respectively acquired with spin echo (SE) and fast spin echo (FSE) sequences for investigation of anatomical and pathological conditions. Scan parameters were as follows: time to repeat/ echo time=550/11 ms (SE) and 3,000/68 ms (FSE), field of view=22×22 mm2, matrix size=256×256 (SE) and 256×248 (FSE), slice thickness=1 mm, number of slices=19, and scan time=9 min 23 s (SE) and 9 min 18 s (FSE).

The tumor tissues were stained by H&E staining method, and the result is shown in FIG. 25f. The immunostaining results of glioma markers are shown in FIG. 25h. From the staining results, high-grade glioma having characteristics such as necrosis, microvascular proliferation, and mitosis were identified (FIG. 20 and FIG. 25h). The tumors had immunoreactivity to GFAP, Nestin, Olig2, and PDGFRα and showed characteristics of human glioma and high proliferation ability was observed.

Through, as somatic cancer driving mutants, for example, Trp53, Pten, and EGFR mutations have abilities to develop malignant glioma from NSCs in SVZ.

5-6. Similarities with Human Glioma (1) Over Time Analysis of Glioma Development To examine the time and spatial relationships between the occurrence of mutations in SVZs and the formation of glioma, the present inventors analysed the progress of glioma development over time.

Specifically, the present inventors obtained serial sections of mouse brain tissue from the olfactory bulb to caudal cortex, 2 days, 8 weeks and 13 to 15 weeks after electroporation. Then, tdTomato-positive cell migration was traced. It is discovered that tdTomato-positive cells migrated from the SVZ to the dorsolateral-caudal cortex and the olfactory bulb (FIG. 20).

In genome-edited mice (n=18), cells harboring driver mutations that migrated to the olfactory bulb properly differentiated to mature neurons and did not lead to glioma development, whereas cells that migrated to the dorsolateral-caudal cortex did (FIG. 20).

The tdTomato-positive cells proliferated throughout serial sections from p64, Pten and Egfr mutated mice. In particular, tdTomato-positive cells increased markedly in number over time in the distant cortical region away from the mutation arising SVZ (−2.5 and −3.5 mm from bregma) (FIG. 21).

Furthermore, the present inventors also noted that 67% of the gliomas developed in a distant region away from the mutation arising SVZ (FIG. 22) by measuring the location of glioma in serial sections or MRI images. In the mice having glioma in cortex (n=12), immunostaining result of H&E staining and nestin, S1000, and DAPI showed normal cytoarchitecture similar to the tumor-free SVZs from GBM patients (FIG. 20).

(2) Identification of Cell Line Developing Glioma

To examine whether cells from NSCs develop glioma, abnormal proliferations were analyzed for neuron, astrocyte, oligodendrocyte, and oligodendrocyteprecursor cells.

Specifically, before the formation of a visible tumor, tdTomato-positive cells in cortex region were immunostained as follows: NeuN for neuron, GFPA for astrocyte, MBP for oligodendrocyte, and Olig2 and PDGFRα for oligodendrocyteprecursor cells.

Majority of tdTomato-positive cells were co-expressing Olig2 or PDGFRα (FIG. 23). Accordingly, it is confirmed that NSCs having driver mutations migrate from SVZ and induce malignant glioma by abnormal proliferation of oligodendrocyteprecursor cells (FIG. 24).

The invention claimed is:

1. A transgenic mouse comprising, knock-out mutations of p53 and Pten genes specifically in nerve stem cells of subventricular zone (SVZ), and
   an activating mutation of epidermal growth factor receptor VIII (EGFRviii) gene in nerve stem cells of SVZ,
   wherein a glioblastoma occurs in the dorsolateral-caudal cortex region,
   wherein the glioblastoma develops from nerve stem cells that are positive for Glial fibrillary acidic protein (GFAP),
   wherein the GFAP positive nerve stem cells have normal cytoarchitecture.

2. The transgenic mouse of claim 1, wherein the glioblastoma is a high-grade glioblastoma having characteristics of necrosis, microvascular proliferation and mitosis, and has an immune response to GFAP, Nestin, Olig2, and PDGFRα.

3. The transgenic mouse of claim 1, wherein the mouse maintains the knockout mutation of p53 and Pten gene specific to nerve stem cells in SVZ even after glioblastoma occurrence.

4. The transgenic mouse of claim 1, wherein the p53 gene comprise at least a nucleotide sequence of SEQ. ID NOs. 38 to 40, and the Pten gene comprise at least a nucleotide sequence of SEQ. ID NOs. 41 to 43.

* * * * *

SEQUENCE LISTING

```
<160> NUMBER OF SEQ ID NOS: 43

<210> SEQ ID NO 1
<211> LENGTH: 17
<212> TYPE: DNA
<213> ORGANISM: Artificial Sequence
<220> FEATURE:
<223> OTHER INFORMATION: TERT_forward

<400> SEQUENCE: 1
gcacctcgcg gtagtgg                                                  17

<210> SEQ ID NO 2
<211> LENGTH: 18
<212> TYPE: DNA
<213> ORGANISM: Artificial Sequence
<220> FEATURE:
<223> OTHER INFORMATION: TERT_reverse

<400> SEQUENCE: 2
gtcctgcccc ttcacctt                                                 18

<210> SEQ ID NO 3
<211> LENGTH: 20
<212> TYPE: DNA
<213> ORGANISM: Artificial Sequence
<220> FEATURE:
<223> OTHER INFORMATION: EGFR_forward

<400> SEQUENCE: 3 ctacaaccccc accacgtacc                                              20

<210> SEQ ID NO 4
<211> LENGTH: 20
<212> TYPE: DNA
<213> ORGANISM: Artificial Sequence
<220> FEATURE:
<223> OTHER INFORMATION: EGFR_reverse

<400> SEQUENCE: 4
ccacccaaag actctccaag                                               20

<210> SEQ ID NO 5
<211> LENGTH: 20
<212> TYPE: DNA
<213> ORGANISM: Artificial Sequence
<220> FEATURE:
<223> OTHER INFORMATION: PTEN_forward

<400> SEQUENCE: 5
accaggacca gaggaaaacct                                              20

<210> SEQ ID NO 6
<211> LENGTH: 20
<212> TYPE: DNA
<213> ORGANISM: Artificial Sequence
<220> FEATURE:
<223> OTHER INFORMATION: PTEN_reverse
```

<400> SEQUENCE: 6
agtcaacaac ccccacaaaa                                              20

<210> SEQ ID NO 7
<211> LENGTH: 20
<212> TYPE: DNA
<213> ORGANISM: Artificial Sequence
<220> FEATURE:
<223> OTHER INFORMATION: TP53_forward

<400> SEQUENCE: 7
gggccagacc taagagcaat                                              20

<210> SEQ ID NO 8
<211> LENGTH: 20
<212> TYPE: DNA
<213> ORGANISM: Artificial Sequence
<220> FEATURE:
<223> OTHER INFORMATION: TP53_reverse

<400> SEQUENCE: 8
ctttgaggtg cgtgtttgtg                                              20

<210> SEQ ID NO 9
<211> LENGTH: 21
<212> TYPE: DNA
<213> ORGANISM: Artificial Sequence
<220> FEATURE:
<223> OTHER INFORMATION: Rb1_forward

<400> SEQUENCE: 9
gcacaaaaag aaacacccaa a                                            21

<210> SEQ ID NO 10
<211> LENGTH: 20
<212> TYPE: DNA
<213> ORGANISM: Artificial Sequence
<220> FEATURE:
<223> OTHER INFORMATION: Rb1_reverse

<400> SEQUENCE: 10
gtccaaagga atgccaattt                                              20

<210> SEQ ID NO 11
<211> LENGTH: 1136
<212> TYPE: PRT
<213> ORGANISM: Artificial Sequence
<220> FEATURE:
<223> OTHER INFORMATION: human EGFR A289V protein

<400> SEQUENCE: 11

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val

```
                      85                  90                  95
Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
                115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
                195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
    275                 280                 285

Val Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510
```

```
Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
            770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
            850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925
```

| | | | | | | | | | | | | |
|---|---|---|---|---|---|---|---|---|---|---|---|---|
|Lys|Gly|Glu|Arg|Leu|Pro|Gln|Pro|Pro|Ile|Cys|Thr|Ile|Asp|Val|Tyr|
| |930| | | |935| | | |940| | | |

Met Ile Met Val Lys Cys Trp Met Ile Asp Ala Asp Ser Arg Pro Lys
945              950                  955                  960

Phe Arg Glu Leu Ile Ile Glu Phe Ser Lys Met Ala Arg Asp Pro Gln
                965                  970                  975

Arg Tyr Leu Val Ile Gln Gly Asp Glu Arg Met His Leu Pro Ser Pro
            980                  985                  990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085

Val Pro Gly Glu Trp Leu Val Trp Lys Gln Ser Cys Ser Ser Thr Ser
    1090                1095                1100

Ser Thr His Ser Ala Ala Ala Ser Leu Gln Cys Pro Ser Gln Val Leu
1105                1110                1115                1120

Pro Pro Ala Ser Pro Glu Gly Glu Thr Val Ala Asp Leu Gln Thr Gln
                1125                1130                1135

<210> SEQ ID NO 12
<211> LENGTH: 3411
<212> TYPE: DNA
<213> ORGANISM: Artificial Sequence
<220> FEATURE:
<223> OTHER INFORMATION: human EGFR A289V cDNA

<400> SEQUENCE: 12

```
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgccaat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg agctgctgg    600 ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gccccccact catgctctac aaccccacca cgtaccagat ggatgtgaac    840
cccgagggca atacagcttt ggtgtcacc tgcgtgaaga agtgtcccg taattatgtg    900
```

```
gtgacagatc acggctcgtg cgtccgagcc tgtggggccg acagctatga gatggaggaa      960
gacggcgtcc gcaagtgtaa gaagtgcgaa gggccttgcc gcaaagtgtg taacggaata     1020
ggtattggtg aatttaaaga ctcactctcc ataaatgcta cgaatattaa acacttcaaa     1080
aactgcacct ccatcagtgg cgatctccac atcctgccgg tggcatttag ggtgactcc      1140 ttcacacata ctcctcctct ggatccacag gaactggata ttctgaaaac cgtaaggaa      1200 atcacagggt ttttgctgat tcaggcttgg cctgaaaaca ggacggacct ccatgccttt     1260
gagaacctag aaatcatacg cggcaggacc aagcaacatg gtcagttttc tcttgcagtc     1320
gtcagcctga acataacatc cttgggatta cgctccctca aggagataag tgatggagat     1380
gtgataattt caggaaacaa aaatttgtgc tatgcaaata caataaactg aaaaaactg      1440 tttgggacct ccggtcagaa aaccaaaatt ataagcaaca gaggtgaaaa cagctgcaag     1500
gccacaggcc aggtctgcca tgccttgtgc tcccccgagg gctgctgggg cccggagccc     1560
agggactgcg tctcttgccg gaatgtcagc cgaggcaggg aatgcgtgga caagtgcaac     1620
cttctggagg gtgagccaag ggagtttgtg gagaactctg agtgcataca gtgccaccca     1680
gagtgcctgc ctcaggccat gaacatcacc tgcacaggac ggggaccaga caactgtatc     1740
cagtgtgccc actacattga cggcccccac tgcgtcaaga cctgcccggc aggagtcatg     1800
ggagaaaaca cacccctggt ctggaagtac gcagacgccg gccatgtgtg ccacctgtgc     1860
catccaaact gcacctacgg atgcactggg ccaggtcttg aaggctgtcc aacgaatggg     1920
cctaagatcc cgtccatcgc cactgggatg gtgggggccc tcctcttgct gctggtggtg     1980
gccctgggga tcggcctctt catgcgaagg cgccacatcg ttcggaagcg cacgctgcgg     2040
aggctgctgc aggagaggga gcttgtggag cctcttacac ccagtggaga agctcccaac     2100
caagctctct tgaggatctt gaaggaaact gaattcaaaa agatcaaagt gctgggctcc     2160
ggtgcgttcg gcacggtgta aagggactc tggatcccag aaggtgagaa agttaaaatt     2220
cccgtcgcta tcaaggaatt aagagaagca acatctccga aagccaacaa ggaaatcctc     2280
gatgaagcct acgtgatggc cagcgtggac aaccccacg tgtgccgcct gctgggcatc     2340
tgcctcacct ccaccgtgca gctcatcacg cagctcatgc ccttcggctg cctcctggac     2400
tatgtccggg aacacaaaga caatattggc tcccagtacc tgctcaactg gtgtgtgcag     2460
atcgcaaagg gcatgaacta cttggaggac cgtcgcttgg tgcaccgcga cctggcagcc     2520
aggaacgtac tggtgaaaac accgcagcat gtcaagatca cagattttgg gctggccaaa     2580
ctgctgggtg cggaagagaa agaataccat gcagaaggag gcaaagtgcc tatcaagtgg     2640
atggcattgg aatcaatttt acacagaatc tatacccacc agagtgatgt ctggagctac     2700
ggggtgactg tttgggagtt gatgacctt ggatccaagc catatgacgg aatccctgcc      2760
agcgagatct cctccatcct ggagaaagga gaacgcctcc ctcagccacc catatgtacc     2820
atcgatgtct acatgatcat ggtcaagtgc tggatgatag acgcagatag tcgcccaaag     2880
ttccgtgagt tgatcatcga attctccaaa atggcccgag accccagcg ctaccttgtc      2940 attcaggggg atgaaagaat gcatttgcca agtcctacag actccaactt ctaccgtgcc     3000
ctgatggatg aagaagacat ggacgacgtg gtggatgccg acgagtacct catcccacag     3060
cagggcttct tcagcagccc ctccacgtca cggactcccc tcctgagctc tctgagtgca     3120
accagcaaca attccaccgt ggcttgcatt gatagaaatg gctgcaaag ctgtcccatc       3180 aaggaagaca gcttccttgca gcgatacagc tcagaccccca caggcgcctt gactgaggac     3240
agcatagacg acaccttcct cccagtgcct ggtgagtggc ttgtctggaa acagtcctgc     3300
```

```
tcctcaacct cctcgaccca ctcagcagca gccagtctcc agtgtccaag ccaggtgctc    3360
cctccagcat ctccagaggg ggaaacagtg gcagatttgc agacacagtg a             3411

<210> SEQ ID NO 13
<211> LENGTH: 341
<212> TYPE: PRT
<213> ORGANISM: Artificial Sequence
<220> FEATURE:
<223> OTHER INFORMATION: human TP53 C176Y protein

<400> SEQUENCE: 13

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Tyr
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Asp Gln Thr Ser Phe
                325                 330                 335

Gln Lys Glu Asn Cys
```

340

<210> SEQ ID NO 14
<211> LENGTH: 1026
<212> TYPE: DNA
<213> ORGANISM: Artificial Sequence
<220> FEATURE:
<223> OTHER INFORMATION: human TP53 C176Y cDNA

<400> SEQUENCE: 14

| | |
|---|---|
| atggaggagc cgcagtcaga tcctagcgtc gagccccctc tgagtcagga acatttca | 60 |
| gacctatgga aactacttcc tgaaaacaac gttctgtccc ccttgccgtc ccaagcaatg | 120 |
| gatgatttga tgctgtcccc ggacgatatt gaacaatggt tcactgaaga cccaggtcca | 180 |
| gatgaagctc ccagaatgcc agaggctgct ccccccgtgg ccctgcacc agcagctcct | 240 |
| acaccggcgg ccctgcacc agcccctcc tggcccctgt catcttctgt cccttcccag | 300 |
| aaaacctacc agggcagcta cggtttccgt ctgggcttct tgcattctgg gacagccaag | 360 |
| tctgtgactt gcacgtactc ccctgccctc aacaagatgt tttgccaact ggccaagacc | 420 |
| tgccctgtgc agctgtgggt tgattccaca ccccgcccg caccgcgt ccgcgccatg | 480 |
| gccatctaca gcagtcaca gcacatgacg gaggttgtga ggcgctaccc ccaccatgag | 540 |
| cgctgctcag atagcgatgg tctggccccct cctcagcatc ttatccgagt ggaaggaaat | 600 |
| ttgcgtgtgg agtatttgga tgacagaaac acttttcgac atagtgtggt ggtgccctat | 660 |
| gagccgcctg aggttggctc tgactgtacc accatccact acaactacat gtgtaacagt | 720 |
| tcctgcatgg gcggcatgaa ccggaggccc atcctcacca tcatcacact ggaagactcc | 780 |
| agtggtaatc tactgggacg aacagctttt gaggtgcgtg tttgtgcctg tcctgggaga | 840 |
| gaccggcgca cagaggaaga gaatctccgc aagaaagggg agcctcacca cgagctgccc | 900 |
| ccagggagca ctaagcgagc actgcccaac aacaccagct cctctcccca gccaaagaag | 960 |
| aaaccactgg atgagaata tttcacccctt caggaccaga ccagctttca aaagaaaat | 1020 |
| tgttaa | 1026 |

<210> SEQ ID NO 15
<211> LENGTH: 341
<212> TYPE: PRT
<213> ORGANISM: Artificial Sequence
<220> FEATURE:
<223> OTHER INFORMATION: human TP53 E285K protein

<400> SEQUENCE: 15

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

```
Phe Leu His Ser Gly Thr Ala Lys Ser Val Thr Cys Thr Tyr Ser Pro
            115                 120                 125
Ala Leu Asn Lys Met Phe Cys Gln Leu Ala Lys Thr Cys Pro Val Gln
        130                 135                 140
Leu Trp Val Asp Ser Thr Pro Pro Gly Thr Arg Val Arg Ala Met
145                 150                 155                 160
Ala Ile Tyr Lys Gln Ser Gln His Met Thr Glu Val Val Arg Cys
                165                 170                 175
Pro His His Glu Arg Cys Ser Asp Ser Asp Gly Leu Ala Pro Pro Gln
            180                 185                 190
His Leu Ile Arg Val Glu Gly Asn Leu Arg Val Glu Tyr Leu Asp Asp
            195                 200                 205
Arg Asn Thr Phe Arg His Ser Val Val Val Pro Tyr Glu Pro Pro Glu
        210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
                245                 250                 255
Leu Glu Asp Ser Ser Gly Asn Leu Leu Gly Arg Asn Ser Phe Glu Val
            260                 265                 270
Arg Val Cys Ala Cys Pro Gly Arg Asp Arg Arg Thr Lys Glu Glu Asn
        275                 280                 285
Leu Arg Lys Lys Gly Glu Pro His His Glu Leu Pro Pro Gly Ser Thr
            290                 295                 300
Lys Arg Ala Leu Pro Asn Asn Thr Ser Ser Ser Pro Gln Pro Lys Lys
305                 310                 315                 320
Lys Pro Leu Asp Gly Glu Tyr Phe Thr Leu Gln Asp Gln Thr Ser Phe
                325                 330                 335
Gln Lys Glu Asn Cys
            340

<210> SEQ ID NO 16
<211> LENGTH: 1026
<212> TYPE: DNA
<213> ORGANISM: Artificial Sequence
<220> FEATURE:
<223> OTHER INFORMATION: human TP53 E285K cDNA

<400> SEQUENCE: 16
atggaggagc cgcagtcaga tcctagcgtc gagccccctc tgagtcagga aacattttca    60
gacctatgga aactacttcc tgaaaacaac gttctgtccc ccttgccgtc caagcaatg   120 gatgatttga tgctgtcccc ggacgatatt gaacaatggt tcactgaaga cccaggtcca   180
gatgaagctc ccagaatgcc agaggctgct cccccgtgg ccctgcacc agcagctcct   240 acaccggcgg cccctgcacc agcccctcc tggccctgt catcttctgt cccttcccag   300
aaaacctacc agggcagcta cggtttccgt ctgggcttct tgcattctgg acagccaag   360 tctgtgactt gcacgtactc ccctgccctc aacaagatgt tttgccaact ggccaagacc   420
tgccctgtgc agctgtgggt tgattccaca ccccgcccg caccgcgt ccgcgccatg   480 gccatctaca gcagtcaca gcacatgacg gaggttgtga ggcgctgccc ccaccatgag   540
cgctgctcag atagcgatgg tctggcccct cctcagcatc ttatccgagt ggaaggaaat   600
ttgcgtgtgg agtatttgga tgacagaaac acttttcgac atagtgtggt ggtgccctat   660
gagccgcctg aggttggctc tgactgtacc accatccact acaactacat gtgtaacagt   720
```

```
tcctgcatgg gcggcatgaa ccggaggccc atcctcacca tcatcacact ggaagactcc    780
agtggtaatc tactgggacg gaacagcttt gaggtgcgtg tttgtgcctg tcctgggaga    840
gaccggcgca caaggaaga gaatctccgc aagaaggggg agcctcacca cgagctgccc     900
ccagggagca ctaagcgagc actgcccaac aacaccagct cctctcccca gccaaagaag    960
aaaccactgg atgagaata tttcacccct caggaccaga ccagctttca aaagaaaat     1020 tgttaa                                                              1026
```

```
<210> SEQ ID NO 17
<211> LENGTH: 321
<212> TYPE: PRT
<213> ORGANISM: Artificial Sequence
<220> FEATURE:
<223> OTHER INFORMATION: human PTEN V317fs6 protein

<400> SEQUENCE: 17

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300
```

Ser Ile Glu Arg Ala Asp Asn Asp Lys Glu Tyr Leu Asp Phe Asn Lys
305                 310                 315                 320

Lys

<210> SEQ ID NO 18
<211> LENGTH: 1207
<212> TYPE: DNA
<213> ORGANISM: Artificial Sequence
<220> FEATURE:
<223> OTHER INFORMATION: human PTEN V317fs6 DNA

<400> SEQUENCE: 18

| | | |
|---|---|---|
| atgacagcca tcatcaaaga gatcgttagc agaaacaaaa ggagatatca agaggatgga | 60 |
| ttcgacttag acttgaccta tatttatcca aacattattg ctatgggatt cctgcagaa | 120 |
| agacttgaag gcgtatacag gaacaatatt gatgatgtag taaggttttt ggattcaaag | 180 |
| cataaaaacc attacaagat atacaatctt tgtgctgaaa gacattatga caccgccaaa | 240 |
| tttaattgca gagttgcaca atatccttt gaagaccata acccaccaca gctagaactt | 300 |
| atcaaaccct tttgtgaaga tcttgaccaa tggctaagtg aagatgacaa tcatgttgca | 360 |
| gcaattcact gtaaagctgg aaagggacga actggtgtaa tgatatgtgc atatttatta | 420 |
| catcggggca aatttttaaa ggcacaagag gccctagatt tctatgggga agtaaggacc | 480 |
| agagacaaaa agggagtaac tattcccagt cagaggcgct atgtgtatta ttatagctac | 540 |
| ctgttaaaga atcatctgga ttatagacca gtggcactgt tgtttcacaa gatgatgttt | 600 |
| gaaactattc caatgttcag tggcggaact tgcaatcctc agtttgtggt ctgccagcta | 660 |
| aaggtgaaga tatattcctc caattcagga cccacacgac gggaagacaa gttcatgtac | 720 |
| tttgagttcc ctcagccgtt acctgtgtgt ggtgatatca agtagagtt cttccacaaa | 780 |
| cagaacaaga tgctaaaaaa ggacaaaatg ttttcacttt t gggtaaatac attcttcata | 840 |
| ccaggaccag aggaaacctc agaaaaagta gaaaatggaa gtctatgtga tcaagaaatc | 900 |
| gatagcattt gcagtataga gcgtgcagat aatgacaagg aatatctaga ctttaacaaa | 960 |
| aaatgatctt gacaaagcaa ataaagacaa agccaaccga tacttttctc caaattttaa | 1020 |
| ggtgaagctg tacttcacaa aaacagtaga ggagccgtca aatccagagg ctagcagttc | 1080 |
| aacttctgta acaccagatg ttagtgacaa tgaacctgat cattatagat attctgacac | 1140 |
| cactgactct gatccagaga tgaacctttt gatgaagat cagcatacac aaattacaaa | 1200 |
| agtctga | 1207 |

<210> SEQ ID NO 19
<211> LENGTH: 318
<212> TYPE: PRT
<213> ORGANISM: Artificial Sequence
<220> FEATURE:
<223> OTHER INFORMATION: human PTEN V317fs3 protein

<400> SEQUENCE: 19

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

| | | | | | | | | | | | | | | | |
|---|---|---|---|---|---|---|---|---|---|---|---|---|---|---|---|
|Tyr|Lys|Ile|Tyr|Asn|Leu|Cys|Ala|Glu|Arg|His|Tyr|Asp|Thr|Ala|Lys|
|65| | | |70| | | | |75| | | | |80| |

Phe Asn Cys Arg Val Ala Gln Tyr Pro Phe Glu Asp His Asn Pro Pro
              85                  90                  95

Gln Leu Glu Leu Ile Lys Pro Phe Cys Glu Asp Leu Asp Gln Trp Leu
             100                 105                 110

Ser Glu Asp Asp Asn His Val Ala Ala Ile His Cys Lys Ala Gly Lys
         115                 120                 125

Gly Arg Thr Gly Val Met Ile Cys Ala Tyr Leu Leu His Arg Gly Lys
         130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
             165                 170                 175

Tyr Tyr Ser Tyr Leu Leu Lys Asn His Leu Asp Tyr Arg Pro Val Ala
         180                 185                 190

Leu Leu Phe His Lys Met Met Phe Glu Thr Ile Pro Met Phe Ser Gly
         195                 200                 205

Gly Thr Cys Asn Pro Gln Phe Val Val Cys Gln Leu Lys Val Lys Ile
         210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                 245                 250                 255

Phe Phe His Lys Gln Asn Lys Met Leu Lys Lys Asp Lys Met Phe His
             260                 265                 270

Phe Trp Val Asn Thr Phe Phe Ile Pro Gly Pro Glu Glu Thr Ser Glu
             275                 280                 285

Lys Val Glu Asn Gly Ser Leu Cys Asp Gln Glu Ile Asp Ser Ile Cys
         290                 295                 300

Ser Ile Glu Arg Ala Asp Asn Asp Lys Glu Tyr Leu Val Leu
305                 310                 315

<210> SEQ ID NO 20
<211> LENGTH: 1208
<212> TYPE: DNA
<213> ORGANISM: Artificial Sequence
<220> FEATURE:
<223> OTHER INFORMATION: human PTEN V317fs3 DNA
<400> SEQUENCE: 20

| | |
|---|---|
|atgacagcca tcatcaaaga gatcgttagc agaaacaaaa ggagatatca agaggatgga|60|
|ttcgacttag acttgaccta tatttatcca acattattg ctatgggatt tcctgcagaa|120|
|agacttgaag gcgtatacag gaacaatatt gatgatgtag taaggttttt ggattcaaag|180|
|cataaaaacc attacaagat atacaatctt tgtgctgaaa gacattatga caccgccaaa|240|
|tttaattgca gagttgcaca atatcctttt gaagaccata cccaccaca gctagaactt|300|
|atcaaaccct tttgtgaaga tcttgaccaa tggctaagtg aagatgacaa tcatgttgca|360|
|gcaattcact gtaaagctgg aaagggacga actggtgtaa tgatatgtgc atatttatta|420|
|catcggggca aatttttaaa ggcacaagag gccctagatt tctatgggga agtaaggacc|480|
|agagacaaaa aggagtaac tattcccagt cagaggcgct atgtgtatta ttatagctac|540|
|ctgttaaaga atcatctgga ttatagacca gtggcactgt tgtttcacaa gatgatgttt|600|
|gaaactattc caatgttcag tggcggaact tgcaatcctc agtttgtggt ctgccagcta|660|

-continued

```
aaggtgaaga tatattcctc caattcagga cccacacgac gggaagacaa gttcatgtac      720
tttgagttcc ctcagccgtt acctgtgtgt ggtgatatca agtagagtt cttccacaaa       780 cagaacaaga tgctaaaaaa ggacaaaatg tttcactttt gggtaaatac attcttcata      840
ccaggaccag aggaaacctc agaaaagta gaaatggaa gtctatgtga tcaagaaatc        900
gatagcattt gcagtataga gcgtgcagat aatgacaagg aatatctagt actttaacaa      960
aaaatgatct tgacaaagca aataaagaca aagccaaccg atactttct ccaaatttta     1020 aggtgaagct gtacttcaca aaacagtag aggagccgtc aaatccagag gctagcagtt     1080
caacttctgt aacaccagat gttagtgaca atgaacctga tcattataga tattctgaca     1140
ccactgactc tgatccagag aatgaacctt ttgatgaaga tcagcataca caaattacaa     1200
aagtctga                                                              1208
```

<210> SEQ ID NO 21
<211> LENGTH: 212
<212> TYPE: PRT
<213> ORGANISM: Artificial Sequence
<220> FEATURE:
<223> OTHER INFORMATION: human Rb K202fs protein

<400> SEQUENCE: 21

```
Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Lys Tyr Tyr Lys Trp
        195                 200                 205

Lys Met Ile Trp
    210
```

<210> SEQ ID NO 22
<211> LENGTH: 2786
<212> TYPE: DNA
<213> ORGANISM: Artificial Sequence
<220> FEATURE:

<223> OTHER INFORMATION: human Rb K202fs DNA

<400> SEQUENCE: 22

```
atgccgccca aaccccccg aaaaacggcc gccaccgccg ccgctgccgc cgcggaaccc      60
ccggcaccgc cgccgccgcc ccctcctgag gaggacccag agcaggacag cggcccggag     120
gacctgcctc tcgtcaggct tgagtttgaa gaaacagaag aacctgattt tactgcatta     180
tgtcagaaat taaagatacc agatcatgtc agagagagag cttggttaac ttgggagaaa     240
gtttcatctg tggatggagt attgggaggt tatattcaaa agaaaaagga actgtgggga     300
atctgtatct ttattgcagc agttgaccta gatgagatgt cgttcacttt tactgagcta     360
cagaaaaaca tagaaatcag tgtccataaa ttctttaact tactaaaaga aattgatacc     420
agtaccaaag ttgataatgc tatgtcaaga ctgttgaaga gtatgatgt attgtttgca      480
ctcttcagca aattggaaag gacatgtgaa cttatatatt tgacacaacc cagcagttcg     540
atatctactg aaataaattc tgcattggtg ctaaaagttt cttggatcac atttttatta     600
gctaaaggga agtattacaa atggaagatg atctggtgat tcatttcag ttaatgctat      660
gtgtccttga ctattttatt aaactctcac ctcccatgtt gctcaaagaa ccatataaaa     720
cagctgttat acccattaat ggttcacctc gaacacccag gcgaggtcag aacaggagtg     780
cacggatagc aaaacaacta gaaaatgata caagaattat tgaagttctc tgtaaagaac     840
atgaatgtaa tatagatgag gtgaaaaatg tttatttcaa aaattttata ccttttatga     900
attctcttgg acttgtaaca tctaatggac ttccagaggt tgaaaatctt tctaaacgat     960
acgaagaaat ttatcttaaa aataaagatc tagatgcaag attattttg gatcatgata      1020
aaactcttca gactgattct atagacagtt ttgaaacaca gagaacacca cgaaaaagta    1080
accttgatga gagggtgaat gtaattcctc cacacactcc agttaggact gttatgaaca    1140
ctatccaaca attaatgatg attttaaatt cagcaagtga tcaaccttca gaaaatctga    1200
tttcctattt taacaactgc acagtgaatc aaaagaaag tatactgaaa agagtgaagg     1260
atataggata catctttaaa gagaaatttg ctaaagctgt gggacagggt tgtgtcgaaa    1320
ttggatcaca gcgatacaaa cttggagttc gcttgtatta ccgagtaatg gaatccatgc    1380
ttaaatcaga agaagaacga ttatccattc aaaattttag caaacttctg aatgacaaca    1440
tttttcatat gtctttattg gcgtgcgctc ttgaggttgt aatggccaca tatagcagaa    1500
gtacatctca gaatcttgat tctggaacag atttgtcttt cccatggatt ctgaatgtgc    1560
ttaatttaaa agcctttgat ttttacaaag tgatcgaaag ttttatcaaa gcagaaggca    1620
acttgacaag agaaatgata aaacatttag aacgatgtga acatcgaatc atggaatccc    1680
ttgcatggct ctcagattca cctttatttg atcttattaa acaatcaaag gaccgagaag    1740
gaccaactga tcaccttgaa tctgcttgtc ctcttaatct tcctctccag aataatcaca    1800
ctgcagcaga tatgtatctt tctcctgtaa gatctccaaa gaaaaaaggt tcaactacgc    1860
gtgtaaattc tactgcaaat gcagagacac aagcaacctc agccttccag acccagaagc    1920
cattgaaatc tacctctctt tcactgtttt ataaaaaagt gtatcggcta gcctatctcc    1980
ggctaaatac actttgtgaa cgccttctgt ctgagcaccc agaattagaa catatcatct    2040
ggaccctttt ccagcacacc ctgcagaatg agtatgaact catgagagac aggcatttgg    2100
accaaattat gatgtgttcc atgtatggca tatgcaaagt gaagaatata gaccttaaat    2160
tcaaaatcat tgtaacagca tacaaggatc ttcctcatgc tgttcaggag acattcaaac    2220
gtgtttttga tcaaagaaga gagtatgatt ctattatagt attctataac tcggtcttca    2280
```

```
tgcagagact gaaaacaaat attttgcagt atgcttccac caggccccct accttgtcac    2340
caatacctca cattcctcga agcccttaca agtttcctag ttcaccctta cggattcctg    2400
gagggaacat ctatatttca cccctgaaga gtccatataa aatttcagaa ggtctgccaa    2460
caccaacaaa aatgactcca agatcaagaa tcttagtatc aattggtgaa tcattcggga    2520
cttctgagaa gttccagaaa ataaatcaga tggtatgtaa cagcgaccgt gtgctcaaaa    2580
gaagtgctga aggaagcaac cctcctaaac cactgaaaaa actacgcttt gatattgaag    2640
gatcagatga agcagatgga agtaaacatc tcccaggaga gtccaaattt cagcagaaac    2700
tggcagaaat gacttctact cgaacacgaa tgcaaaagca gaaatgaat gatagcatgg     2760 atacctcaaa caaggaagag aaatga                                         2786
```

<210> SEQ ID NO 23
<211> LENGTH: 18
<212> TYPE: DNA
<213> ORGANISM: Artificial Sequence
<220> FEATURE:
<223> OTHER INFORMATION: EGFR_RTqPCR_Forward

<400> SEQUENCE: 23
cgtctcttgc cggaatgt                                                  18

<210> SEQ ID NO 24
<211> LENGTH: 25
<212> TYPE: DNA
<213> ORGANISM: Artificial Sequence
<220> FEATURE:
<223> OTHER INFORMATION: EGFR_RTqPCR_Reverse

<400> SEQUENCE: 24
ggattaaaga aataacctcc taccc                                          25

<210> SEQ ID NO 25
<211> LENGTH: 19
<212> TYPE: DNA
<213> ORGANISM: Artificial Sequence
<220> FEATURE:
<223> OTHER INFORMATION: RNAseP_RTqPCR_Forward

<400> SEQUENCE: 25
gggagatgcg gaagaatgt                                                 19

<210> SEQ ID NO 26
<211> LENGTH: 19
<212> TYPE: DNA
<213> ORGANISM: Artificial Sequence
<220> FEATURE:
<223> OTHER INFORMATION: RNAseP_RTqPCR_Reverse

<400> SEQUENCE: 26
cctccagtca gccacagaa                                                 19

<210> SEQ ID NO 27
<211> LENGTH: 20
<212> TYPE: DNA
<213> ORGANISM: Artificial Sequence
<220> FEATURE:
<223> OTHER INFORMATION: LDHA_RTqPCR_Forward

<400> SEQUENCE: 27
actgtgaccc ttatccaggc                                                20

```
<210> SEQ ID NO 28
<211> LENGTH: 23
<212> TYPE: DNA
<213> ORGANISM: Artificial Sequence
<220> FEATURE:
<223> OTHER INFORMATION: LDHA_RTqPCR_Reverse

<400> SEQUENCE: 28
cttcccttaa ctagctctca gga                                              23

<210> SEQ ID NO 29
<211> LENGTH: 21
<212> TYPE: RNA
<213> ORGANISM: Artificial Sequence
<220> FEATURE:
<223> OTHER INFORMATION: sgRNA_p53

<400> SEQUENCE: 29
ggtgtaatag ctcctgcatg g                                                21

<210> SEQ ID NO 30
<211> LENGTH: 22
<212> TYPE: RNA
<213> ORGANISM: Artificial Sequence
<220> FEATURE:
<223> OTHER INFORMATION: sgRNA_Pten

<400> SEQUENCE: 30
ggttggtcaa gatcttcaca ga                                               22

<210> SEQ ID NO 31
<211> LENGTH: 22
<212> TYPE: RNA
<213> ORGANISM: Artificial Sequence
<220> FEATURE:
<223> OTHER INFORMATION: sgRNA_lacz

<400> SEQUENCE: 31
ggtgcgaata cgcccacgcg at                                               22

<210> SEQ ID NO 32
<211> LENGTH: 20
<212> TYPE: DNA
<213> ORGANISM: Artificial Sequence
<220> FEATURE:
<223> OTHER INFORMATION: Mouse_Trp53_forward

<400> SEQUENCE: 32
aggtagggag cgacttcacc                                                  20

<210> SEQ ID NO 33
<211> LENGTH: 20
<212> TYPE: DNA
<213> ORGANISM: Artificial Sequence
<220> FEATURE:
<223> OTHER INFORMATION: Mouse_Trp53_reverse

<400> SEQUENCE: 33
taaggatagg tcggcggttc                                                  20

<210> SEQ ID NO 34
<211> LENGTH: 20
<212> TYPE: DNA
<213> ORGANISM: Artificial Sequence
<220> FEATURE:
<223> OTHER INFORMATION: Mouse_Pten_forward
```

<400> SEQUENCE: 34
agaccataac ccaccacagc                                              20

<210> SEQ ID NO 35
<211> LENGTH: 20
<212> TYPE: DNA
<213> ORGANISM: Artificial Sequence
<220> FEATURE:
<223> OTHER INFORMATION: Mouse_Pten_reverse

<400> SEQUENCE: 35
tacaccagtc cgtcccttc                                               20

<210> SEQ ID NO 36
<211> LENGTH: 21
<212> TYPE: DNA
<213> ORGANISM: Artificial Sequence
<220> FEATURE:
<223> OTHER INFORMATION: EGFR_seq_forward

<400> SEQUENCE: 36
cccaggcact tgatgatact c                                            21

<210> SEQ ID NO 37
<211> LENGTH: 20
<212> TYPE: DNA
<213> ORGANISM: Artificial Sequence
<220> FEATURE:
<223> OTHER INFORMATION: EGFR_seq_reverse

<400> SEQUENCE: 37
cttgctttgg gtggagagtt                                              20

<210> SEQ ID NO 38
<211> LENGTH: 102
<212> TYPE: DNA
<213> ORGANISM: Artificial Sequence
<220> FEATURE:
<223> OTHER INFORMATION: Trp53_indel1

<400> SEQUENCE: 38
tgtgtcttcc cccaggccgg ctctgagtat accaccatcc actacaagta catgtgtaat     60
agctcctgca cttgggggc atgaaccgcc gacctatcct ta                       102

<210> SEQ ID NO 39
<211> LENGTH: 98
<212> TYPE: DNA
<213> ORGANISM: Artificial Sequence
<220> FEATURE:
<223> OTHER INFORMATION: Trp53_indel2

<400> SEQUENCE: 39
tgtgtcttcc cccaggccgg ctctgagtat accaccatcc actacaagta catgtgtaat     60
agctcctgtg gggggcatga accgccgacc tatcctta                            98

<210> SEQ ID NO 40
<211> LENGTH: 101
<212> TYPE: DNA
<213> ORGANISM: Artificial Sequence
<220> FEATURE:
<223> OTHER INFORMATION: Trp53_indel3

<400> SEQUENCE: 40

```
tgtgtcttcc cccaggccgg ctctgagtat accaccatcc actacaagta catgtgtaat    60
agctcctgca atgggggca tgaaccgccg acctatcctt a                        101

<210> SEQ ID NO 41
<211> LENGTH: 110
<212> TYPE: DNA
<213> ORGANISM: Artificial Sequence
<220> FEATURE:
<223> OTHER INFORMATION: Pten_indel1

<400> SEQUENCE: 41
agaccataac ccaccacagc tagaacttat caaacccttc ttgaagatct tgaccaatgg    60
ctaagtgaag atgacaatca tgttgcagca attcactgta aagctggaaa              110

<210> SEQ ID NO 42
<211> LENGTH: 108
<212> TYPE: DNA
<213> ORGANISM: Artificial Sequence
<220> FEATURE:
<223> OTHER INFORMATION: Pten_indel2

<400> SEQUENCE: 42
agaccataac ccaccacagc tagaacttat caaaccctct gaagatcttg accaatggct    60
aagtgaagat gacaatcatg ttgcagcaat tcactgtaaa gctggaaa                108

<210> SEQ ID NO 43
<211> LENGTH: 110
<212> TYPE: DNA
<213> ORGANISM: Artificial Sequence
<220> FEATURE:
<223> OTHER INFORMATION: Pten_indel3

<400> SEQUENCE: 43
agaccataac ccaccacagc tagaacttat caaacccttc gtgaagatct tgaccaatgg    60
ctaagtgaag atgacaatca tgttgcagca attcactgta aagctggaaa              110
```